US007855190B2

(12) United States Patent
Bell et al.

(10) Patent No.: US 7,855,190 B2
(45) Date of Patent: *Dec. 21, 2010

(54) METHODS OF HORMONAL TREATMENT UTILIZING CONTRACEPTIVE REGIMENS WITH CONTINUOUS ESTROGEN ADMINISTRATION

(75) Inventors: Robert G. Bell, Palm Harbor, FL (US); Carole S. Ben-Maimon, Merion, PA (US); Beata Iskold, Livingston, NJ (US); Lance J. Bronnenkant, Snyder, NY (US); Howard Hait, Wilmington, DE (US); Kathleen Z. Reape, Bryn Mawr, PA (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1603 days.

This patent is subject to a terminal disclaimer.

(21) Appl. No.: 10/892,404

(22) Filed: Jul. 16, 2004

(65) Prior Publication Data

US 2005/0143359 A1 Jun. 30, 2005

Related U.S. Application Data

(60) Provisional application No. 60/487,257, filed on Jul. 16, 2003.

(51) Int. Cl.
*A01N 45/00* (2006.01)
*A61K 31/56* (2006.01)
(52) U.S. Cl. ......... 514/170; 514/171; 514/182
(58) Field of Classification Search ......... 514/170, 514/171, 182, 649
See application file for complete search history.

(56) References Cited

U.S. PATENT DOCUMENTS

| 3,568,828 A | 3/1971 | Lerner |
| 4,145,416 A | 3/1979 | Lachnit-Fixson et al. |
| 4,171,358 A | 10/1979 | Black |
| 4,215,691 A | 8/1980 | Wong |
| 4,291,014 A | 9/1981 | Keith et al. |
| 4,292,315 A | 9/1981 | Vorys |
| 4,390,531 A | 6/1983 | Edgren |
| 4,438,139 A | 3/1984 | Keith et al. |
| 4,530,839 A | 7/1985 | Pasquale |
| 4,534,468 A | 8/1985 | Nuckols et al. |
| 4,544,554 A | 10/1985 | Pasquale |
| 4,616,006 A | 10/1986 | Pasquale |
| 4,628,051 A | 12/1986 | Pasquale |
| 4,685,911 A | 8/1987 | Konno et al. |
| 4,736,849 A | 4/1988 | Leonard et al. |
| 4,752,478 A | 6/1988 | Bondi et al. |
| 4,762,717 A | 8/1988 | Crowley, Jr. |
| 4,962,098 A | 10/1990 | Boissonneault |
| 4,971,998 A | 11/1990 | Wurtman et al. |
| 4,994,449 A | 2/1991 | Leonard |
| 5,010,070 A | 4/1991 | Boissonneault |
| 5,043,331 A | 8/1991 | Hirvonen et al. |
| 5,098,714 A | 3/1992 | Wright et al. |
| 5,108,995 A | 4/1992 | Casper |
| 5,208,225 A | 5/1993 | Boissonneault et al. |
| 5,256,421 A | 10/1993 | Casper |
| 5,262,408 A | 11/1993 | Bergink |
| 5,276,022 A | 1/1994 | Casper |
| 5,280,023 A | 1/1994 | Ehrlich et al. |
| 5,296,230 A | 3/1994 | Chien et al. |
| 5,340,584 A | 8/1994 | Spicer et al. |
| 5,382,573 A | 1/1995 | Casper |
| 5,510,341 A | 4/1996 | Ehrlich et al. |
| 5,552,394 A | 9/1996 | Hodgen |
| 5,567,695 A | 10/1996 | Labrie |
| 5,585,370 A | 12/1996 | Casper |
| 5,633,242 A | 5/1997 | Oettel et al. |
| 5,662,927 A | 9/1997 | Ehrlich et al. |
| RE35,724 E | 2/1998 | Pasquale |
| 5,747,480 A | 5/1998 | Gast |
| 5,753,639 A | 5/1998 | Labrie |
| 5,756,490 A | 5/1998 | Lachnit et al. |
| 5,827,843 A | 10/1998 | Koninckx |
| 5,858,405 A | 1/1999 | Gast |
| 5,891,867 A | 4/1999 | Lanquetin et al. |
| 5,898,032 A | 4/1999 | Hodgen |
| RE36,247 E | 7/1999 | Plunkett et al. |
| 5,980,940 A | 11/1999 | Spona et al. |
| 6,027,749 A | 2/2000 | Schmidt-Gollwitzer et al. |

(Continued)

FOREIGN PATENT DOCUMENTS

CN 1189101 A 7/1998

(Continued)

OTHER PUBLICATIONS

British Medical Journal, Nov. 1969, pp. 380-381.*

(Continued)

*Primary Examiner*—Sreeni Padmanabhan
*Assistant Examiner*—Samira Jean-Louis
(74) *Attorney, Agent, or Firm*—Sterne, Kessler, Goldstein & Fox P.L.L.C.

(57) ABSTRACT

The present invention provides contraceptive regimens in which a female is administered a combined dosage form of estrogen and progestin followed by a period of administration of estrogen. The disclosed contraceptive regimens can be administered to a female as a method of providing non-contraceptive benefits.

42 Claims, 10 Drawing Sheets

U.S. PATENT DOCUMENTS

| | | | |
|---|---|---|---|
| 6,028,064 | A | 2/2000 | Rodriguez et al. |
| 6,139,873 | A | 10/2000 | Hughes, Jr. et al. |
| 6,214,815 | B1 | 4/2001 | Shangold et al. |
| 6,251,956 | B1 | 6/2001 | Kafrissen et al. |
| 6,265,393 | B1 | 7/2001 | Heinrichs |
| 6,306,914 | B1 | 10/2001 | de Ziegler et al. |
| 6,312,722 | B1 | 11/2001 | Schmidt-Gollwitzer et al. |
| 6,319,911 | B1 | 11/2001 | Rodriguez |
| RE37,838 | E | 9/2002 | Spona et al. |
| 6,451,779 | B1 | 9/2002 | Hesch |
| 6,479,475 | B1 | 11/2002 | Gast |
| 6,500,814 | B1 | 12/2002 | Hesch |
| 6,511,970 | B1 | 1/2003 | Rodriguez |
| 6,765,002 | B2 | 7/2004 | Rodriguez |
| 6,787,531 | B1 | 9/2004 | Hilman et al. |
| 7,150,355 | B2 | 12/2006 | Coe et al. |
| 7,320,969 | B2 * | 1/2008 | Bell et al. .................. 514/170 |
| 7,427,609 | B2 | 9/2008 | Leonard |
| 2001/0044431 | A1 | 11/2001 | Rodriguez |
| 2002/0132801 | A1 | 9/2002 | Heil et al. |
| 2003/0018018 | A1 | 1/2003 | Hodgen et al. |
| 2003/0114429 | A1 | 6/2003 | Hilman et al. |
| 2003/0119798 | A1 | 6/2003 | Heil et al. |
| 2003/0139381 | A1 | 7/2003 | Bell et al. |
| 2003/0144258 | A1 | 7/2003 | Heil et al. |
| 2003/0216366 | A1 | 11/2003 | Leonard et al. |
| 2003/0229057 | A1 | 12/2003 | Caubel et al. |
| 2004/0009960 | A1 | 1/2004 | Heil et al. |
| 2004/0142914 | A1 | 7/2004 | Friedman et al. |
| 2004/0222123 | A1 | 11/2004 | Niemann |
| 2004/0251301 | A1 | 12/2004 | Niemann et al. |
| 2005/0064031 | A1 | 3/2005 | Stockemann et al. |
| 2006/0135496 | A1 | 6/2006 | DiLiberti et al. |
| 2007/0111975 | A1 | 5/2007 | DiLiberti et al. |
| 2007/0158233 | A1 | 7/2007 | Coe et al. |
| 2008/0064670 | A1 | 3/2008 | Bell et al. |
| 2008/0125402 | A1 | 5/2008 | DiLiberti et al. |
| 2008/0132473 | A1 | 6/2008 | Bell et al. |

FOREIGN PATENT DOCUMENTS

| | | |
|---|---|---|
| EP | 0 253 607 A1 | 1/1988 |
| EP | 0 911 029 B1 | 4/2002 |
| WO | WO 93/17686 A1 | 9/1993 |
| WO | WO 98/04246 A2 | 2/1998 |
| WO | WO 98/04266 A1 | 2/1998 |
| WO | WO 98/04267 A1 | 2/1998 |
| WO | WO 00/38691 A1 | 7/2000 |
| WO | WO 01/93848 A2 | 12/2001 |
| WO | WO 02/03975 A2 | 1/2002 |
| WO | WO 03/049744 A1 | 6/2003 |
| WO | WO 2004/080442 A1 | 9/2004 |
| WO | WO 2005/032558 A1 | 4/2005 |

OTHER PUBLICATIONS

European Opposition Document D32, Facts About Seasonale®, 1 page, Barr Laboratories, Inc. (available after Sep. 5, 2003), cited in the Opposition to Patent No. 0 911 029 B1.

European Opposition Document D33, Seasonale® Product Brochure, 15 pages, Duramed Pharmaceuticals, Inc. (Jan. 2004), cited in the Opposition to Patent No. 0 911 029 B1.

Goldzieher, J.W., "Use and Misuse of the Term Potency with Respect to Oral Contraceptives," *J. Reprod. Med.* 31: 533-539, The Journal of Reproductive Medicine, Inc. (1986).

King, R.J.B. and Whitehead, M.I., "Assessment of the potency of orally administered progestins in women," *Fertility and Sterility* 46: 1062-1066, The American Fertility Society (1986).

Mashchak, C.A., et al., "Comparison of pharmacodynamic properties of various estrogen formulations," *Am. J. Obstet. Gynecol.* 144: 511-518, The C.V. Mosby Company (1982).

Miller, L. and Notter, K., "Menstrual Reduction With Extended Use of Combination Oral Contraceptive Pills: Randomized Controlled Trial," *Obstet. Gynecol.* 98: 771-778, Elsevier Science, Inc. (2001).

Phillips, A., et al., "A Comparison of the Potencies and Activities of Progestogens Used in Contraceptives," *Contraception* 36: 181-192, Geron-X, Inc. (1987).

Piper, J.M. and Kennedy, D.L., "Oral Contraceptives in the United States: Trends in Content and Potency," *Intl. J. of Epidemiol.* 16: 215-221, Oxford University Press (1987).

Shearman, R.P., "Oral contraceptive agents," *Med. J. Australia* 144: 201-205, Australasian Medical Publishing Company (1986).

"Headaches: OCs are 'guilty by association'," *Contraceptive Technology Update* 14:109-112, Thomson American Health Consultants (1993).

International Search Report for International Application No. PCT/US02/38602, European Patent Office, Netherlands, mailed on Apr. 4, 2003.

Co-pending U.S. Appl. No. 10/893,795, inventor Hodgen, G.D., filed Jul. 19, 2004, entitled "Methods of Extended Use Oral Contraception" (as amended) (Not Published).

Kistner, R.W., "The Treatment of Endometriosis by Inducing Pseudopregnancy with Ovarian Hormones," *Fertil. Steril.* 10:539-556, Paul B. Hoeber, Inc. Publishers (1959).

Kistner, R.W., "The Effects of New Synthetic Progestogens on Endometriosis in the Human Female," *Fertil. Steril.* 16:61-80, Harper & Row, Publishers, Inc. (1965).

Kistner, R.W., "Current Status of the Hormonal Treatment of Endometriosis," *Clin. Obstet. Gynecol.* 9:271-292, Harper & Row, Publishers, Inc. (1966).

Kistner, R.W., "Management of Endometriosis in the Infertile Patient," *Fertil. Steril.* 26:1151-1166, Harper & Row, Publishers, Inc. (1975).

Rumore, M.M., and Rumore, J.S., "Clinical Therapeutics of Endometriosis, Part 2," *Am. Pharm.* NS29:40-44, American Pharmaceutical Association (1989).

International Search Report for International Application No. PCT/US04/22829, United States Patent and Trademark Office, United States, mailed on Oct. 16, 2006.

American Psychiatric Association, "Premenstrual Dysphoric Disorder," in *DSM-IV™: Diagnostic and Statistical Manual of Mental Disorders*, 4th Ed., American Psychiatric Association, Washington, DC, pp. 715-718 (1994).

Anderson, F.D., "The Safety and Efficacy of Seasonale, a Novel 91-Day Extended Oral Contraceptive Regimen," *Obstet. Gynecol.* 99:26S, Lippincott Williams & Wilkins (2002).

Budavari, S., ed., "4112. Fluoxetine," in *Merck Index*, 11th Ed., Merck & Company, Inc., Whitehouse Station, NJ, p. 655 (Nov. 2006).

Cachrimanidou, A.C., et al., "Long-interval treatment regimen with a desogestrel-containing oral contraceptive," *Contraception* 48:205-216, Elsevier (1993).

Davies, G.C., et al., "Ovarian Activity and Bleeding Patterns During Extended Continuous Use of a Combined Contraceptive Vaginal Ring," *Contraception* 46:269-278, Elsevier (1992).

de Voogd, W.S., "Postponement of Withdrawal Bleeding With a Monophasic Oral Contraceptive Containing Desogestrel and Ethinylestradiol," *Contraception* 44:107-112, Elsevier (1991).

Freeman, E.W., et al., "Evaluation of a Unique Oral Contraceptive in the Treatment of Premenstrual Dysphoric Disorder," *J. Womens Health Gend. Based Med.* 10:561-569, Mary Ann Liebert, Inc. (2001).

Goldzieher, J.W., "Use and Misuse of the Term Potency with Respect to Oral Contraceptives," *J. Reprod. Med.* 31:533-539, Science Printers and Publishers, Inc. (1986).

Graham, C.A., and Sherwin, B.B., "A Prospective Treatment Study of Premenstrual Symptoms Using a Triphasic Oral Contraceptive," *J. Psychosom. Res.* 36:257-266, Pergamon Press (1992).

Hamerlynck, J.V., et al., "Postponement of Withdrawal Bleeding in Women Using Low-Dose Combined Oral Contraceptives," *Contraception* 35:199-205, Elsevier (1987).

Katzung, B.G., ed., "Hormonal Contraception," in *Basic & Clinical Pharmacology*, 6th Ed., Appleton & Lange, Norwalk, CT, pp. 619-623 (1995).

Kovacs, G.T., et al., "A trimonthly regimen for oral contraceptives," *Br. J. Fam. Plann.* 19:274-275, Faculty of Family Planning and Reproductive Health Care (1994).

Loudon, N.B., et al., "Acceptability of an oral contraceptive that reduces the frequency of menstruation: the tri-cycle pill regimen," Br. Med. J. 2:487-490, British Medical Association (1977).

Sulak, P.J., et al., "Extending the Duration of Active Oral Contraceptive Pills to Manage Hormone Withdrawal Symptoms," *Obstet. Gynecol.* 89:179-183, Lippincott Williams & Wilkins (1997).

Threlkeld, D.S., ed., "Oral Contraceptives," in *Drug Facts and Comparisons*, Facts and Comparisons, St. Louis, MO, pp. 257-268 (1985).

Walker, A., and Bancroft, J., "Relationship Between Premenstrual Symptoms and Oral Contraceptive Use: A Controlled Study," *Psychosom. Med.* 52:86-96, Lippincott Williams & Wilkins (1990).

World Health Organization Scientific Group, "8. Risks With Particular Reference to Neoplasia of Therapeutic Estrogens and Progestins Given to Peri- and Postmenopausal Women," in *Research on the Menopause*, World Health Organization, Geneva, Switzerland, pp. 52-69 (1981).

International Preliminary Examination Report for International Application No. PCT/US02/38602, completed on Jul. 9, 2004, European Patent Office, Munich, Germany.

International Search Report for International Application No. PCT/US04/013589, mailed on Mar. 9, 2006, U.S. Patent Office, Alexandria, Virginia.

Written Opinion for International Application No. PCT/US04/013589, completed on Nov. 11, 2005, Alexandria, Virginia.

Written Opinion for International Application No. PCT/US04/22829, completed on Sep. 18, 2006, U.S. Patent Office, Alexandria, Virginia.

Non-Final Office Action for U.S. Appl. No. 10/309,313, filed on Dec. 4, 2002, mailed on Nov. 4, 2005.

Final Office Action for U.S. Appl. No. 10/309,313, filed on Dec. 4, 2002, mailed on May 1, 2006.

Non-Final Office Action for U.S. Appl. No. 10/309,313, filed on Dec. 4, 2002, mailed on Sep. 11, 2006.

Final Office Action for U.S. Appl. No. 10/309,313, filed on Dec. 4, 2002, mailed on Mar. 19, 2007.

Co-pending U.S. Appl. No. 12/162,445, inventors DiLiberti and Reape, filed Jan. 29, 2007 (Not Yet Published).

Supplemental Partial European Search Report for European Application No. EP 04 77 8369, dated Aug. 19, 2009, The Hague, The Netherlands.

European Opposition Document, Appellant's Grounds of Appeal, with Main Request and First, Second, Third, Fourth, Fifth and Sixth Auxiliary Requests, 37 pages, submitted by Patentee in the Opposition to European Patent No. 0 911 029 B1 (Nov. 2004).

European Opposition Document D35, Declaration by Alan H. DeCherney, M.D., 6 pages submitted with Appellant's Grounds of Appeal in the Opposition to European Patent No. 0 911 029 B1 (Nov. 2004).

Exhibit A of Declaration by Alan H. DeCherney, M.D. (European Opposition Document D35), *Curriculum Vitae*, Alan Hersh DeCherney, M.D., 54 pages, Dec. 2003, submitted with Appellant's Grounds of Appeal in the Opposition to European Patent No. 0 911 029 B1.

European Opposition Document D36, "Coolest Inventions 2003," *Time Magazine*, issue of Nov. 17, 2003, 26 pages, submitted with Appellant's Grounds of Appeal in the Opposition to European Patent No. 0 911 029 B1.

Sulak, P.J., "Should your patient be on extended-use OCs?" *Contemporary OB/GYN* 48:35-46, Thomson Medical Economics (Sep. 2003).

Adams Hillard, P.J., "Oral contraception noncompliance: The extent of the problem," *Adv. Contracep.* 8(Suppl. 1):13-20, Kluwer Academic Publishers (1992).

Branigan, E.F. and Estes, M.A., "A randomized clinical trial of treatment of clomiphene citrate-resistant anovulation with the use of oral contraceptive pill suppression and repeat clomiphene citrate treatment," *Am. J. Obstet. Gynecol.* 188:1424-1430, Mosby, Inc. (Jun. 2003).

Case, A.M. and Reid, R.L., "Effects of the Menstrual Cycle on Medical Disorders," Arch. Intern. Med. 158:1405-1412, American Medical Association (1998).

Coffee, A., "Hormone-Based Contraception: The Extended Cycle Regimen," Supplement to *Drug Topics*, pp. 3-15, Advanstar Communications, Inc. (Jan. 2004).

Daugherty, J.E., "Treatment Strategies for Premenstrual Syndrome," *Am. Fam. Phys.* 58:183-192, American Academy of Family Physicians (1998).

Dickey, R.P., "Oral Contraception: Realizing the Promise by Overcoming the Pitfalls," *Individualizing Oral Contraceptive Therapy, OBG Management Supplement*, pp. 2-6, Watson Pharma, Inc. (2000).

European Opposition Document, Notice of Opposition (Article 99 and Rule 55 EPC) submitted by Akzo Nobel N. V. in the Opposition to European Patent No. 0 911 029 B1, 8 pages (Jan. 2002).

European Opposition Document, Notice and Statement of Opposition, submitted by Schering AG in the Opposition to European Patent No. 0 911 029 B1, 33 pages (Jan. 2003).

European Opposition Document, Response to Communication of Notices of Opposition, submitted by Patentee in the Opposition to European Patent No. 0 911 029 B1, 10 pages (Oct. 2003).

European Opposition Document, Summons to Attend Oral Proceedings Pursuant to Rule 71 (1) EPC, issued by European Patent Office, Netherlands, in the Opposition to European Patent No. 0 911 029 B1, 1 pages (Jan. 2004).

European Opposition Document, Written Submission, with new Main and Auxiliary Requests, submitted by Patentee in the Opposition to European Patent No. 0 911 029 B1, 23 pages (Apr. 2004).

European Opposition Document, Further Written Submissions, submitted by Schering AG in the Opposition to European Patent No. 0 911 029 B1, 17 pages (Apr. 2004).

European Opposition Document, Further Submission, "Urgent—Oral Proceedings Scheduled for Aug. 6, 2004," submitted by Patentee in the Opposition to European Patent No. 0 911 029 B1, 2 pages (May 2004).

European Opposition Document, Further Submission, "Urgent: Oral Proceedings on Jun. 8, 2004," submitted by Akzo Nobel N. V. in the Opposition to European Patent No. 0 911 029 B1, 1 page (May 2004).

European Opposition Document, Further Submission, "Urgent—Oral Proceedings Jun. 8, 2004," submitted by Schering AG in the Opposition to European Patent No. 0 911 029 B1, 2 pages (May 2004).

European Opposition Document, Decision revoking the European Patent No. EP 0 911 029 (Article 102(1), (3)EPC), issued by European Patent Office in the Opposition to European Patent No. 0 911 029 B1, Netherlands, 41 pages (Jul. 1, 2004).

European Opposition Document D1, Cachrimanidou, A.-C., et al., "Long-interval treatment regimen with a desogestrel-containing oral contraceptive," *Contraception* 48:205-216, Butterworth-Heinemann (1993), cited in the Opposition to European Patent No. 0 911 029 B1.

European Opposition Document D2, Kovacs, G.T., et al., "A trimonthly regimen for oral contraceptives," *Brit. J. Fam. Planning* 19:274-275, Faculty of Family Planning and Reproductive Health Care (1994), cited in the Opposition to European Patent No. 0 911 029 B1.

European Opposition Document D3, Davies, G.C., et al., "Ovarian Activity and Bleeding Patterns During Extended Continuous Use of a Combined Contraceptive Vaginal Ring," *Conception* 46:269-278, Elsevier (1992), cited in the Opposition to European Patent No. 0 911 029 B1.

European Opposition Document D4, "Vier keer per jaar ongesteld," *Intermediair*, 2 pages, Intermediair (May 2002), cited in the Opposition to European Patent No. 0 911 029 B1.

Partial English translation of European Opposition Document D4, "Having a period four times per year," *Intermediair*, 2 pages, Intermediair (May 2002), cited in the Opposition to European Patent No. 0 911 029 B1 (Document AR9).

European Opposition Document D5, Loudon, N.B., et al., "Acceptability of an oral contraceptive that reduces the frequency of menstruation: the tri-cycle pill regimen," *Brit. Med. J.* 2:487-490, British Medical Association (1977), cited in the Opposition to European Patent No. 0 911 029 B1.

European Opposition Document D6, Vollebregt, J.A., et al., "A Study on Postponement of Menses with Low-Dose Combined Oral Contraceptives—Outcome and Acceptability," *Adv. Contraception* 1:207, Abstract No. 19, Kluwer Academics (1985), cited in the Opposition to European Patent No. 0 911 029 B1.

European Opposition Document D7, Omtzigt, A.M. and Boerrigter, P.J., "The effect of 30 μg ethinylestradiol/75 μg gestodene and 20 μg ethinylestradiol/150 μg desogestrel on cycle control during normal and extended oral contraceptive intake," *Eur. J. Contracept. Reprod. Health Care* 1:155, Abstract No. FC70, Parthenon Publishing (1996), cited in the Opposition to European Patent No. 0 911 029 B1.

European Opposition Document D8, Szarewski, A. and Guillebaud, J., eds., *Contraception, A User's Handbook*, Oxford University Press, Oxford, UK, pp. 46, 53, 54, 84, 87 (1994), cited in the Opposition to European Patent No. 0 911 029 B1.

European Opposition Document D9, Schneider, H.P.G., et al., eds., "Empfängnis-verhütung," Urban & Schwarzenberg, Munich, Germany, pp. 7-8 (1996), cited in the Opposition to European Patent No. 0 911 029 B1.

European Opposition Document D10, Guillebaud, J., ed., "*Contraception. Your questions answered*," Churchill Livingstone, New York, NY, pp. 75, 131, 154-155, (1986), cited in the Opposition to European Patent No. 0 911 029 B1.

European Opposition Document D11, Mishell, D.R., Jr., "Oral Contraception: Past, Present, and Future Perspectives," *Int. J. Fertil.* 36: 7-18, MSP International (1991), cited in the Opposition to European Patent No. 0 911 029 B1.

European Opposition Document D12, de Voogd, W.S., "Postponement of Withdrawal Bleeding with a Monophasic Oral Contraceptive Containing Desogestrel and Ethinylestradiol," *Contraception* 44:107-112, Elsevier (1991), cited in the Opposition to European Patent No. 0 911 029 B1.

European Opposition Document D13, Rutter, W., et al., "Women's attitudes to withdrawal bleeding and their knowledge and beliefs about the oral contraceptive pill," *Med. J. Australia* 149:417-419, Australasian Medical Publishing Co. (1988), cited in the Opposition to European Patent No. 0 911 029 B1.

European Opposition Document D14, Sulak, P.J., et al., "Extending the Duration of Active Oral Contraceptive Pills to Manage Hormone Withdrawal Symptoms," *Obstet. & Gynecol.* 89:179-182, Lippincott, Williams & Wilkins (1997), cited in the Opposition to European Patent No. 0 911 029 B1.

European Opposition Document D15, U.S. Patent No. 5,552,394, Hodgen, G.D., issued Sep. 3, 1996, cited in the Opposition to European Patent No. 0 911 029 B1.

European Opposition Document D16, Speroff, L., et al., eds., "Chapter 2. Oral Contraception," in: *A Clinical Guide for Contraception*, Lippincott, Williams & Wilkins, pp. 25-117 (2000), cited in the Opposition to European Patent No. 0 911 029 B1.

European Opposition Document D17, Düsterberg, B., et al., "Terminal Half-lives in Plasma and Bioavailability of Norethisterone, Levonorgestrel, Cyproterone acetate and Gestodene in Rats, Beagles and Rhesus Monkeys," *Contraception* 24:673-383, Elsevier (1981), cited in the Opposition to European Patent No. 0 911 029 B1.

European Opposition Document D18, Düsterberg, B., et al., "Half-lives in Plasma and Bioavailability of Ethinylestradiol in Laboratory Animals," *Drug Res.* 36:1187-1190, Edititio Cantor (1986), cited in the Opposition to European Patent No. 0 911 029 B1.

European Opposition Document D19, WIPO International Publication No. 93/17686, published Sep. 16, 1993, cited in the Opposition to European Patent No. 0 911 029 B1.

European Opposition Document D20, Letter filed by Schering AG in Opposition to EP 0686037 B1, the Medical College of Hampton Roads, 5 pages (Aug. 2003), cited in the Opposition to European Patent No. 0 911 029 B1.

European Opposition Document D21, Hamerlynck, J.V.Th.H., et al., "Postponement of Withdrawal Bleeding in Women Using Low-Dose Combined Oral Contraceptives," *Contraception* 35:199-205, Elsevier (1987), cited in the Opposition to European Patent No. 0 911 029 B1.

European Opposition Document D22, Anderson, F.D. and Hait, H., "A multicenter, randomized study of an extended cycle oral contraceptive," *Contraception* 68:89-96, Elsevier (Aug. 2003), cited in the Opposition to European Patent No. 0 911 029 B1.

European Opposition Document D23, Report of Bleeding observed with Seasonale products as compared to conventional OC products, addendum to Anderson, F.D. and Hait, H., "A multicenter, randomized study of an extended cycle oral contraceptive," *Contraception* 68:89-96, Elsevier (Aug. 2003), 2 pages, cited in the Opposition to European Patent No. 0 911 029 B1.

European Opposition Document D24, Glaser, J., "Seasonale®, Market Research," carried out by Ziment Associates on behalf of Barr Laboratories, Inc. (Jan. 2003), 14 pages, cited in the Opposition to European Patent No. 0 911 029 B1.

European Opposition Document D25, "The 2003 Gallup Study of the Market for Oral Contraceptives," conducted by Multi-Sponsor Surveys, Inc., for Barr Laboratories, Inc., 17 pages (May 2003), cited in the Opposition to European Patent No. 0 911 029 B1.

European Opposition Document D26, Comparison of Seasonale with other birth control products, IMS Health, Market data from Jun. 2001-Jan. 2004, 4 pages, cited in the Opposition to European Patent No. 0 911 029 B1.

European Opposition Document D27, Declaration of Dr. Anne Szarewski, In the Matter of EP 0 911 029 B1, Medical College of Hampton Roads and Opposition Thereto by Schering AG, 8 pages, cited in the Opposition to European Patent No. 0 911 029 B1 (Apr. 2004).

Annex I of Declaration of Dr. Anne Szarewski (Document D27 in the Opposition to European Patent No. EP 0 911 029 B1), Szarewski, A.M., *Curriculum Vitae*, 14 pages, 2003.

Annex II of Declaration of Dr. Anne Szarewski (Document D27 in the Opposition to European Patent No. EP 0 911 029 B1), "Commercially Available Monophasic Combined Oral Contraceptive Pills," and "Ratio of equivalence given in patent EP 0 911 029 B1", 2002.

Annex III of Declaration of Dr. Anne Szarewski (Document D27 in the Opposition to European Patent No. EP 0 911 029 B1), Belsey, E.M., "The Association Between Vaginal Bleeding Patterns and Reasons for Discontinuation of Contraceptive Use," *Contraception* 38:207-225, Elsevier (1998).

Annex IV of Declaration of Dr. Anne Szarewski (Document D27 in Opposition to European Patent No. EP 0 911 029 B1), Benagiano, G. and Fraser, I., The Depo-Provera Debate, Commentary on the Article "Depo-Provera, A Critical Analysis," in: *Contraception* 24:493-528, Elsevier (1981).

Annex V of Declaration of Dr. Anne Szarewski (Document D27 in Opposition to European Patent No. EP 0 911 029 B1), "Is Cerazette the minipill of choice?," *Drug Ther. Bull.* 41:1-3, Consumers' Association (Sep. 2003).

Annex VI of Declaration of Dr. Anne Szarewski (Document D27 in Opposition to European Patent No. EP 0 911 029 B1), Committee for Proprietary Medicinal Products, "Clinical Investigation of Steroid Contraceptives in Women," *Note for Guidance on Clinical Investigation of Steroid Contraceptives in Women*, 5 pages, The European Agency for the Evaluation of Medicinal Products (2000).

Annex VII of Declaration of Dr. Anne Szarewski (Document D27 in Opposition to European Patent No. EP 0 911 029 B1), Goldzieher, J.W. and Fotherby, K., eds., *Pharmacology of the Contraceptive Steroids*, Raven Press, New York, NY, pp. 82-86 (1994).

Annex VIII of Declaration of Dr. Anne Szarewski (Document D27 in Opposition to European Patent No. EP 0 911 029 B1), Guillebaud, J., ed., "The pill: how do I take it?," in: *The Pill and Other Hormones for Contraception*, Oxford University Press, Great Britain, UK, pp. 52-53, 110-113, 182-183, 190-191 (1991).

Annex IX of Declaration of Dr. Anne Szarewski (Document D27 in Opposition to European Patent No. EP 0 911 029 B1), Adams Hillard, P.J., "The patient's reaction to side effects of oral contraceptives," *Am. J. Obstet. Gynecol.* 161:1412-1415, Mosby-Year Book (1989).

Annex X of Declaration of Dr. Anne Szarewski (Document D27 in Opposition to European Patent No. EP 0 911 029 B1), International Working Group, "A consensus statement: enhancing patient compliance and oral contraceptive efficacy," *Brit. J. Fam. Planning* 18:126-129, Faculty of Family Planning and Reproductive Health Care (1993).

Annex XI of Declaration of Dr. Anne Szarewski (Document D27 in Opposition to European Patent No. EP 0 911 029 B1), Korver, T., for the Collaborative Study Group, "A double-blind study comparing the contraceptive efficacy, acceptability and safety of two progestogen-only pills containing desogestrel 75 µg/day or levonorgestrel 30 µg/day," *Eur. J. Contra. Reprod. Health Care* 3:169-178, Parthenon Publishing (1998).

Annex XII of Declaration of Dr. Anne Szarewski (Document D27 in Opposition to European Patent No. EP 0 911 029 B1), Larsson, K.S. and Machin, D., "Predictability of the safety of hormone contraceptives from canine toxicological studies," in: *Safety requirements for contraceptive steroids*, Michael D., ed., Cambridge University Press, Oxford, UK, pp. 230-269 (1989).

Annex XIII of Declaration of Dr. Anne Szarewski (Document D27 in Opposition to European Patent No. EP 0 911 029 B1), Lumbiganon, P., "Depot-medroxyprogesterone acetate (DMPA) and cancer of the endometrium and ovary," *Contraception* 49:203-209, Butterworth-Heinemann (1994).

Annex XIV of Declaration of Dr. Anne Szarewski (Document D27 in Opposition to European Patent No. EP 0 911 029 B1), Rice, C.F., et al., "A comparison of the inhibition of ovulation achieved by desogestrel 75 µg and levnorgestrel 30 µg daily," *Human Reprod.* 14:982-985, Oxford University Press (1999).

Annex XV of Declaration of Dr. Anne Szarewski (Document D27 in Opposition to European Patent No. EP 0 911 029 B1), Rosenberg, M. and Waugh, M.S., "Causes and consequences of oral contraceptive noncompliance," *Am. J. Obstet. Gnyecol.* 180:S276-S279, Mosby, Inc. (1999).

Annex XVI of Declaration of Dr. Anne Szarewski (Document D27 in Opposition to European Patent No. EP 0 911 029 B1), Rosenberg, M.J., et al., "Use and Misuse of Oral Contraceptives: Risk Indicators for Poor Pill Taking and Discontinuation," *Contraception* 51: 283-288, Elsevier Science Inc. (1995).

Annex XVII of Declaration of Dr. Anne Szarewski (Document D27 in Opposition to European Patent No. EP 0 911 029 B1),Rosenfield, A., et al., "The Food and Drug Administration and Medroxyprogesterone Acetate," *JAMA* 249:2922-2928, American Medical Association (1983).

Annex XVIII of Declaration of Dr. Anne Szarewski (Document D27 in Opposition to European Patent No. EP 0 911 029 B1), Szarewski , A., ed., "Figure 3.5 Oestrogen-dominant and progestogen-dominant pills," in: *Hormonal Contraception: A Women's Guide*, Macdonald Optima, pp. 45 (1991).

Annex XIX of Declaration of Dr. Anne Szarewski (Document D27 in Opposition to European Patent No. EP 0 911 029 B1), Szarewski, A. and Guillebaud, J., eds., "Which Pill Suit me Best?," in: *Contraception, A User's Handbook*, Oxford University press, pp. 43-72 (1994).

Annex XX of Declaration of Dr. Anne Szarewski (Document D27 in Opposition to European Patent No. EP 0 911 029 B1), Wilkinson, C. and Szarewski, A., eds., "Management of Breakthrough Bleeding," in: *Contraceptive Dilemmas*, Altman Publishing, St. Albans, England, pp. 4-7 (2003).

Annex XXI of Declaration of Dr. Anne Szarewski, (Document D27 in Opposition to European Patent No. EP 0 911 029 B1), WHO Collaborative Study Group, "Depot-Medroxyprogesterone Acetate (DMPA) and Risk of Endometrial Cancer," *Int. J. Cancer* 49:186-190, Wiley-Liss, Inc. (1991).

Annex XXII of Declaration of Dr. Anne Szarewski (Document D27 in Opposition to European Patent No. EP 0 911 029 B1), WHO Collaborative Study Group, "Breast cancer and depot-medroxyprogesterone acetate: a multinational study," *Lancet* 338:833-838, Lancet Publishing Company (1991).

European Opposition Document D28, SEA-301, Summary Statistics: Observed Total Number of Days of Unscheduled Bleeding and/or Spotting by Cycle, cited in the Opposition for European Patent No. 0 911 029 B1 , 2003.

European Opposition Document D29, Letter from U.S. FDA to Barr Research, Inc., undated and redacted, cited in the Opposition to European Patent No. 0 911 029 B1 , 2001.

European Opposition Document D30, European Patent No. 0 253 607 A1, published Jan. 20, 1988, cited in the Opposition to European Patent No. 0 911 029 B1.

European Opposition Document D31, Publically available Food and Drug Administration papers relating to marketing authorization for Seasonale®, 347 pages, cited in the Oppostion to Patent No. 0 911 029 B1 (publicly available Mar. 2004).

European Opposition Document D32, Facts About Seasonale®, 1 page, Barr Laboratories, Inc., available online at www.seasonale. com, cited in the Opposition to Patent No. 0 911 029 B1, Sep. 2003.

European Opposition Document D33, Seasonale®, Product Brochure, 15 pages, available online at www.seasonale.com, cited in the Opposition to Patent No. 0 911 029 B1, Jan. 2004.

European Opposition Document D34, Seasonale®, Product Description and Information, Duramed Pharmaceuticals, Inc., 39 pages (Sep. 2003), cited in the Opposition to Patent No. 0 911 029 B1.

Notice of Paragraph IV Certification letter on behalf of Watson Laboratories, Inc., from Barry S. White of Frommer Lawrence & Haug LLP to Bruce L. Downey of Barr Laboratories, Inc., 17 pages (Jun. 2004).

Letter from Andreas Görlich to Barr Laboratories, Inc., entitled "Tablets against pregnancy 'Seasonale'," 3 pages (Jun. 2004).

Attachment 1, Letter from Andreas Görlich to Barr Laboratories, "Gynäkologische Sensation oder graue Theorie? Monatsblutung nur noch zweimal im Jahr—wie ist das möglich?," (Gesundheits-Magazin) Health Magazine, 1 page (1984).

English language translation of Attachment 1 to Letter from Andreas Görlich to Barr Laboratories, "Gynecological Sensation or Gray Theory? Menstruation only twice a year—how is that possible?," Health Magazine (1984).

Attachment 2, Letter from Andreas Görlich to Barr Laboratories, "Zwei "Monatsblutungen" pro Jahr sind genug. Gefordert ist die sog. Distanz-Pille," Medical Tribune/Gyne, 1 page (1983).

Attachment 3, Letter from Andreas Görlich to Barr Laboratories, "Zwei Monatsblutungen pro Jahr sind genug!" Medical Tribune, Austrian Edition, and Medical Tribune, Swiss Edition, 2 pages (1984).

English language translation of Attachments 2 and 3, Letter from Andreas Görlich to Barr Laboratories, "Two "Menstrual Periods" Per Year Are Enough," Medical Tribune/Gyne (1983).

Attachment 4, Letter from Andreas Görlich to Barr Laboratories, "Frauenarzt fordert: Schafft die sinniosen Monatsblutungen ab!" Cosmopolitan 9:177, 1 page (1984).

English language translation of Attachment 4 to Letter from Andreas Görlich to Barr Laboratories, "Gynecologist issues challenge: away with senseless menstrual bleeding!," Cosmopolitan 9:177 (1984).

Fernandez, E., et al., "Oral contraceptives and colorectal cancer risk: a meta-analysis," *Brit. J. Canc.* 84:722-727, Cancer Research Campaign (2001).

Frackiewicz, E.J. and Shiovitz, T.M., "Evaluation and Management of Premenstrual Syndrome and Premenstrual Dysphoric Disorder," *J. Am. Pharm. Assoc.* 41:437-447, American Pharmaceutical Association (2001).

Freeman, E.W., et al., "Concurrent Use of Oral Contraceptives With Antidepressants for Premenstrual Syndromes," *J. Clin. Psychopharmacol.* 21:540-542, Williams & Wilkins (2001).

Garraway, W.M., et al., "Limb Fractures in a Defined Population. I. Frequency and Distribution," *Mayo Clin. Proc.* 54:701-707, Mayo Clinic (1979).

Gusberg, S.B. and Hall, R.E., "Precursors of Corpus Cancer. III. The Appearance of Cancer of the Endometrium in Estrogenically Conditioned Patients," *J. Obstet. Gyneco.* 17:397-412, Paul B. Hoeber, Inc. (1961).

Hipkin, L., Col., "The Induction of Amenorrhoea," *J.R. Army Med. Corps* 138:15-18, Royal Army Medical Corps (1992).

Holt, V., et al., "Body Weight and Risk of Oral Contraceptive Failure," *Obstet. Gynecol.* 99:820-827, American College of Obstetricians and Gynecologists (May 2002).

Kay, C.R. and Wingrave, S.J., "Oral Contraceptives and Rheumatoid Arthritis," *Lancet I*:1437, Lancet Publishing Group (1983).

Koetsawang, S., et al., "A Randomized, Double-Blind Study of Six Combined Oral Contraceptives," *Contraception* 25:231-241, Elsevier (1982).

Kornaat, H., et al., "The Acceptance of a 7-Week Cycle With a Modern Low-Dose Oral Contraceptive (Minulet®), " *Contraception* 45:119-127, Butterworth-Heinemann (1992).

Kudrow, L., "The Relationship of Headache Frequency to Hormone Use in Migraine," *Headache* 15:36-40, Blackwell Science (1975).

Kuhl, H., "Comparative Pharmacology of Newer Progestogens," *Drugs* 51:189-215, ADIS International Ltd. (1996).

Küpper, C. and Loch, E.-G., "Prämenstruelles Syndrom," *Deutsche Apotheker Zeitung* 24:23-29, Deutscher Apotheker Verlag (1988).

Linos, A., et al., "Rheumatoid Arthritis and Oral Contraceptives," *Lancet* 1:871, The Lancet Publishing Group (1978).

Lundeen, S.G., et al., "Rat uterine complement C3 expression as a model for progesterone receptor modulators: characterization of the new progestin trimegestone," *J. Steroid Biochem. & Malec. Biol.* 78:137-143, Elsevier Science Ltd. (2001).

MacDonald, N. E. and Brunham, R., "The Effects of Undetected and Untreated Sexually Transmitted Diseases: Pelvic Inflammatory Disease and Ectopic Pregnancy in Canada," *Canadian J. Human Sexuality* 6:161-170, Sieccan (1997).

"Medical Management of Endometriosis," *ACOG Practice Bulletin*, No. 11, pp. 1-14, American College of Obstetricians and Gynecologists (1999).

Mortola, J.F., et al., "Diagnosis of Premenstrual Syndrome by a Simple, Prospective, and Reliable Instrument: The Calendar of Premenstrual Experiences," *Obstet. Gynecol.* 76:302-307, Elsevier Science Publishing Co., Inc. (1990).

Philibert D., et al., "The Pharmacological profile of a novel norpregnane progestin (trimegestone)," *Gynecol. Endocrinol.* 13:316-326, Parthenon Publishing (1999).

"Premenstrual Dysphoric Disorder," in: *Diagnostic and Statistical Manual of Mental Disorders*, American Psychiatric Association, Washington, DC, pp. 715-718 (1994).

Report of a WHO Scientific Group, "8. Risks, with Particular Reference to Neoplasia, of Therapeutic Estrogens and Progestins Given to Peri- and Postmenopausal Women," in: *Research on the menopause*, World Health Organization, Geneva, Switzerland, pp. 52-69 (1981).

Rittmaster, R.S., "Hirsutism," *Lancet* 349:191-195, Lancet Publishing Group (1997).

Romano, S., et al., "The Role of Fluoxetine in the Treatment of Premenstrual Dysphoric Disorder," *Clin. Ther.* 21:615-633, Excerpta Medica, Inc. (1999).

Rosenberg, M.J. and Waugh, M.S., "Oral contraceptive discontinuation: A prospective evaluation of frequency and reasons," *Am. J. Obstet. Gynecol.* 179:577-582, Mosby, Inc. (1998).

Sheth, A., et al., "A Randomized, Double-Blind Study of Two Combined and Two Progestogen-Only Oral Contraceptives," *Contraception* 25:243-252, Elsevier (1982).

Silberstein, S.D. and Merriam, G.R., "Physiology of the menstrual cycle," *Cephalalgia* 20:148-154, Blackwell Science Ltd. (2000).

Stearns, S., "PMS and PMDD in the Domain of Mental Health Nursing," *J. Psychosoc. Nurs.* 39:16-27, Slack Incorporated (2001).

Steiner, M., et al., "Fluoxetine in the Treatment of Premenstrual Dysphoria," *New. Engl. J. Med.* 332:1529-1534, Massachusetts Medical Society (1995).

Steiner, M., "Premenstrual Syndromes," *Annu. Rev. Med.* 48:447-455, Annual Reviews Inc. (1997).

Steiner, M. and Born, L., "Diagnosis and treatment of premenstrual dysphoric disorder: an update," *Int. Clin Psychopharmacol.* 15(Suppl. 3):S5-S17, Lippincott, Williams & Wilkins (2000).

Sulak, P.J., et al., "Hormone Withdrawal Symptoms in Oral Contraceptive Users," *Obstet. Gynecol.* 95:261-266, Lippincott, Williams & Wilkins (2000).

Sulak, P.J., et al., "Acceptance of altering the standard 21-day/7-day oral contraceptive regimen to delay menses and reduce hormone withdrawal symptoms," *Am. J. Obstet. Gynecol.* 186:1142-1148, Mosby, Inc. (Jun. 2002).

Weström, L. and Mårdh, P.-A., "Chap. 49. Acute pelvic inflammatory disease (PID)," in: *Sexually Transmitted Diseases*, 2$^{nd}$ Ed, Holmes, K.K., et al., eds., McGraw-Hill, Inc., New York, NY, pp. 593-613 (1990).

Whitty, C.W.M., et al., "The Effect of Oral Contraceptives on Migraine," *Lancet* 1:856-859, Lancet Publishing Company (1966).

Wysocki, S., et al., "Hormonal Contraceptives: Extending the Benefits," *Am. J. Nurse Practitioners* 6:19-29, American College of Nurse Practitioners (Nov./Dec. 2002).

Yonkers, K.A., "Antidepressants in the Treatment of Premenstrual Dysphoric Disorder," *J. Clin. Psychiatry* 58(Suppl. 14):4-13, Physicians Post Graduate Press (1997).

Yonkers, K.A., "Medical Management of Premenstrual Dysphoric Disorder," *J. Gend. Specif. Med.* 2:55-60, Multimedia Healthcare (1999).

Co-Pending U.S. Appl. No. 10/837,268, Ben-Maimon et al., filed May 3, 2004 (Not Published).

"First Amended Answer, Affirmative Defenses and Counterclaims of Defendants Watson Laboratories, Inc. and Watson Pharmaceuticals, Inc. To Teva Women's Health, Inc.'s Complaint" in *Teva Women's Health, Inc.* v. *Lupin, Ltd. et al.*, Civil Docket Case No. 2:10-CV-00080, U.S. District Court, District of New Jersey (Newark), filed May 28, 2010, 45 pages, including Exhibit A.

Docket Sheet for *Duramed Pharmaceuticals, Inc.* v. *Sandoz Inc.*, Civil Docket Case No. 3:07-CV-05940, U.S. District Court, District of New Jersey (Trenton), most recent entry date of Feb. 23, 2010, 24 pages.

Docket Sheet for *Teva Women's Health, Inc.* v. *Lupin, Ltd. et al*, Civil Docket Case No. 3:09-CV-05112, U.S. District Court, District of New Jersey (Trenton), most recent entry date of Mar. 22, 2010, 7 pages.

Docket Sheet for *Duramed Pharmaceuticals, Inc.* v. *Watson Laboratories, Inc. et al*, Civil Docket Case No. 3:08-CV-00116, U.S. District Court, District of Nevada (Reno), most recent entry date of Apr. 21, 2010, 60 pages.

"Order" in *Duramed Pharmaceuticals, Inc.* v. *Watson Laboratories, Inc. et al*, Civil Docket Case No. 3:08-CV-00116, U.S. District Court, District of Nevada (Reno), filed Mar. 31, 2010, 11 pages.

Docket Sheet for *Teva Women's Health, Inc.* v. *Lupin, Ltd. et al*, Civil Docket Case No. 2:10-CV-00603, U.S. District Court, District of New Jersey (Newark), most recent entry date of Apr. 12, 2010, 6 pages.

"Answer and Counterclaims of Lupin Pharmaceuticals, Inc. and Lupin, Ltd." in *Teva Women's Health, Inc.* v. *Lupin, Ltd. et al*, Civil Docket Case No. 2:10-CV-00603, U.S. District Court, District of New Jersey (Newark), filed Mar. 19, 2010, 13 pages.

Docket Sheet for *Teva Women's Health, Inc.* v. *Mylan Pharmaceuticals, Inc. et al*, Civil Docket Case No. 2:10-CV-01235, U.S. District Court, District of New Jersey (Newark), most recent entry date of Apr. 28, 2010, 4 pages.

Docket Sheet for *Teva Women's Health, Inc.* v. *Lupin, Ltd. et al*, Civil Docket Case No. 2:10-CV-00080, U.S. District Court, District of New Jersey (Newark), most recent entry date of Apr. 30, 2010, 11 pages.

Docket Sheet for *Watson Laboratories, Inc.* v. *Teva Women's Health, Inc.*, Civil Docket Case No. 3:10-CV-00115, U.S. District Court, District of Nevada (Reno) most recent entry date of Mar. 31, 2010, 3 pages.

"Complaint for Declaratory Judgment of Patent Invalidity and Non-Infringement" in *Watson Laboratories, Inc.* v. *Teva Women's Health, Inc.*, Civil Docket Case No. 3:10-CV-00115, U.S. District Court, District of Nevada (Reno), filed Feb. 25, 2010, 8 pages.

Docket Sheet for *Teva Women's Health, Inc.* v. *Mylan Pharmaceuticals, Inc. et al*, Civil Docket Case No. 2:10-CV-01234, U.S. District Court, District of New Jersey (Newark), most recent entry date of Mar. 15, 2010, 3 pages.

Docket Sheet for *Duramed Pharmaceuticals, Inc.* v. *Sandoz Inc.*, Civil Docket Case No.: 3:07-CV-05940, U.S. District Court, District of New Jersey (Trenton), most recent entry date of Jun. 30, 2010, 17 pages.

Docket Sheet for *Teva Women's Health, Inc.* v. *Lupin, Ltd.* et al, Civil Docket Case No.: 2:10-CV-00603, U.S. District Court, District of New Jersey (Newark), most recent entry date of Jul. 27, 2010, 6 pages.

Docket Sheet for *Teva Women's Health, Inc.* v. *Mylan Pharmaceuticals, Inc.* et al, Civil Docket Case No.: 2:10-CV-01235, U.S. District Court, District of New Jersey (Newark), most recent entry date of Jul. 30, 2010, 7 pages.

Docket Sheet for *Teva Women's Health, Inc.* v. *Lupin, Ltd.* et al, Civil Docket Case No.: 2:10-CV-00080, U.S. District Court, District of New Jersey (Newark), most recent entry date of Aug. 9, 2010, 15 pages.

"Exhibit B" (Deposition of Howard Hait) to "*Motion to Seal by Teva Women's Health, Inc.*" in *Teva Women's Health, Inc.* v. *Lupin, Ltd.* et al, Civil Docket Case No.: 2:10-CV-00080, U.S. District Court, District of New Jersey (Newark), filed Jul. 13, 2010, 92 pages.

"Exhibit D" (Deposition of Kathleen Z. Reape, M.D.) to *"Motion to Seal by Teva Women's Health, Inc."* in *Teva Women's Health, Inc.* v. *Lupin, Ltd.* et al, Civil Docket Case No.: 2:10-CV-00080, U.S. District Court, District of New Jersey (Newark), filed Jul. 13, 2010, 49 pages.

*"Defendants Watson Laboratories, Inc. And Watson Pharmaceuticals, Inc.'s Brief in Opposition to Plaintiff's Motion to Dismiss/Strike Watson's Inequitable Conduct Counterclaim and Defense"* in *Teva Women's Health, Inc.* v. *Lupin, Ltd.* et al, Consolidated Civil Docket Case Nos.: 2:10-CV-00080 and 2:10-cv-01234, filed Jul. 23, 2010, 44 pages.

Docket Sheet for *Teva Women's Health, Inc.* v. *Mylan Pharmaceuticals, Inc.* et al, Civil Docket Case No.: 2:10-CV-01234, U.S. District Court, District of New Jersey (Newark), most recent entry date of Aug. 9, 2010, 9 pages.

Docket Sheet for *Watson Laboratories, Inc.* v. *Teva Women's Health, Inc.*, Civil Docket Case No.: 3:10-CV-00115, U.S. District Court, District of Nevada (Reno) most recent entry date of May 19, 2010, 2 pages.

Docket Sheet for *Duramed Pharmaceuticals, Inc.* v. *Watson Laboratories, Inc.*, Case No.: Oct. 1331, U.S. Court of Appeals for the Federal Circuit, most recent entry date of Jul. 23, 2010, 5 pages.

*"Non-Confidential Brief for Defendant-Appellant"* in *Duramed Pharmaceuticals, Inc.* v. *Watson Laboratories, Inc.*, Case No.: 10-1331, U.S. Court of Appeals for the Federal Circuit, filed Jun. 28, 2010, 69 pages.

Docket Sheet for *Teva Women's Health, Inc.* v. *Mylan Pharmaceuticals, Inc.* et al, Civil Docket Case No.: 2:10-CV-01235, U.S. District Court, District of New Jersey (Newark), most recent entry date of Oct. 1, 2010, 9 pages.

Docket Sheet for *Teva Women's Health, Inc.* v. *Lupin, Ltd.* et al, Civil Docket Case No.: 2:10-CV-00080, U.S. District Court, District of New Jersey (Newark), most recent entry date of Oct. 15, 2010, 23 pages.

"Exhibit 9—Redacted" (Part 1 of Expert Report of Patricia J. Sulak, M.D.) to *"Redaction to Order on Motion to Seal by Teva Women's Health, Inc."* in *Teva Women's Health, Inc.* v. *Lupin, Ltd.* et al, Civil Docket Case No.: 2:10-CV-00080, U.S. District Court, District of New Jersey (Newark), filed Aug. 30, 2010, 50 pages.

"Exhibit 9—Redacted" (Part 2 of Expert Report of Patricia J. Sulak, M.D.) to *"Redaction to Order on Motion to Seal by Teva Women's Health, Inc."* in *Teva Women's Health, Inc.* v. *Lupin, Ltd.* et al, Civil Docket Case No.: 2:10-CV-00080, U.S. District Court, District of New Jersey (Newark), filed Aug. 30, 2010, 48 pages.

"Exhibit 10—Redacted" (Part 1 of Deposition of Patricia J. Sulak, M.D.) to *"Redaction to Order on Motion to Seal by Teva Women's Health, Inc."* in *Teva Women's Health, Inc.* v. *Lupin, Ltd.* et al, Civil Docket Case No.: 2:10-CV-00080, U.S. District Court, District of New Jersey (Newark), filed Aug. 30, 2010, 101 pages.

"Exhibit 10—Redacted" (Part 2 of Deposition of Patricia J. Sulak, M.D.) to *"Redaction to Order on Motion to Seal by Teva Women's Health, Inc."* in *Teva Women's Health, Inc.* v. *Lupin, Ltd.* et al, Civil Docket Case No.: 2:10-CV-00080, U.S. District Court, District of New Jersey (Newark), filed Aug. 30, 2010, 100 pages.

"Exhibit 10—Redacted" (Part 3 of Deposition of Patricia J. Sulak, M.D.) to *"Redaction to Order on Motion to Seal by Teva Women's Health, Inc."* in *Teva Women's Health, Inc.* v. *Lupin, Ltd.* et al, Civil Docket Case No. 2:10-CV-00080, U.S. District Court, District of New Jersey (Newark), filed Aug. 30, 2010, 83 pages.

*"Notice of Motion for Leave to File First Amended Answer and Counterclaims of Lupin Pharmaceuticals, Inc. And Lupin, Ltd."* in *Teva Women's Health, Inc.* v. *Lupin, Ltd.* et al, Civil Docket Case No.: 2:10-CV-00080, U.S. District Court, District of New Jersey (Newark), filed Oct. 8, 2010, 18 pages.

Docket Sheet for *Teva Women's Health, Inc.* v. *Mylan Pharmaceuticals, Inc.* et al, Civil Docket Case No.: 2:10-CV-01234, U.S. District Court, District of New Jersey (Newark), most recent entry date of Oct. 8, 2010, 13 pages.

Docket Sheet for *Duramed Pharmaceuticals, Inc.* v. *Sandoz Inc.*, Civil Docket Case No.: 3:07-CV-05940, U.S. District Court, District of New Jersey (Trenton), most recent entry date of Oct. 15, 2010, 25 pages.

Docket Sheet for *Duramed Pharmaceuticals, Inc.* v. *Watson Laboratories, Inc.*, Case No.: 10-1331, U.S. Court of Appeals for the Federal Circuit, most recent entry date of Sep. 2, 2010, 5 pages.

* cited by examiner

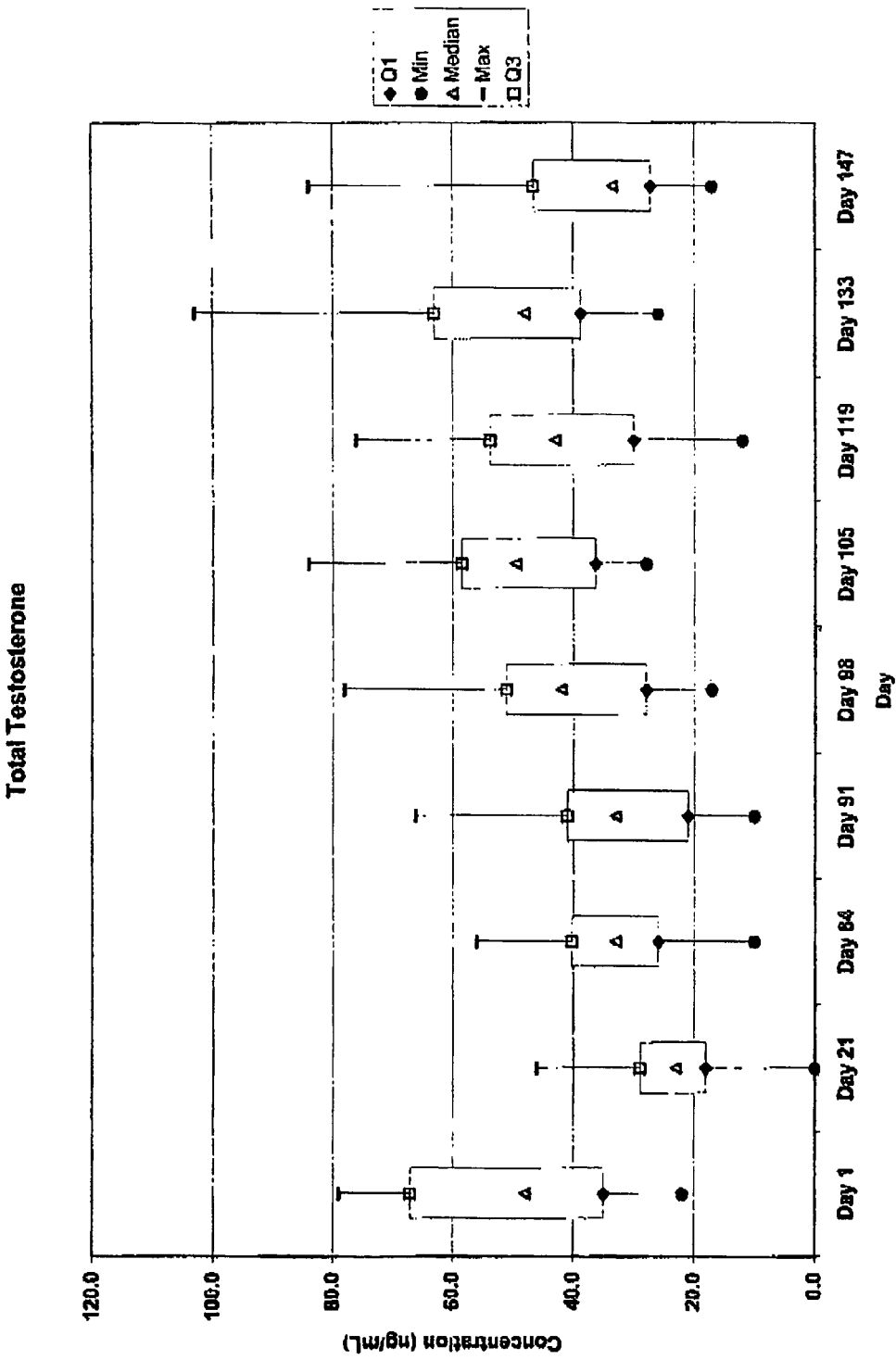

METHODS OF HORMONAL TREATMENT UTILIZING CONTRACEPTIVE REGIMENS WITH CONTINUOUS ESTROGEN ADMINISTRATION

CROSS-REFERENCE TO RELATED APPLICATIONS

This application claims the benefit, under 35 U.S.C. §119 (e), of the earlier filing date of U.S. Appl. No. 60/487,257, filed on Jul. 16, 2003. The entire contents of U.S. Appl. No. 60/487,257 is incorporated by reference herein in its entirety.

BACKGROUND OF THE INVENTION

1. Field of the Invention

The present invention relates to methods of hormonal treatment that utilize contraceptive regimens involving administration of estrogen and progestin, followed by administration of estrogen.

2. Related Art

The human menstrual cycle involves a repetitive sequence of hormonal changes that result in episodic uterine bleeding. Normally, each menstrual cycle has a mean interval of about 21 to about 35 days, conventionally beginning with the first day of menstrual flow and ending on the day before the next onset of bleeding. Duration of the menstrual flow is usually about 2 to about 6 days with loss of about 20 to about 60 ml of blood.

The menstrual cycle is divided into follicular and luteal phases, each corresponding to changes occurring in the ovary. These phases may also be described as proliferative or secretory, corresponding to changes observed in the uterine endometrium. Variations in the length of the cycle are usually due to alterations in the follicular phase, because the luteal phase length remains relatively constant at about 12 to about 16 days.

During the follicular phase, several primary follicles are recruited for further growth and development. Granulosa cells in primary follicles possess follicle stimulating hormone (FSH) and estradiol receptors. Upon FSH stimulation, granulosa cells produce aromatase. This enzyme converts the androgens androstenedione and testosterone, made in response to luteinizing hormone (LH) by thecal cells, to estrone and estradiol, respectively. Granulosa cells respond to estradiol by undergoing mitosis to increase the number of granulosa cells and estradiol production. By day 7 of the cycle, one enlarging primary follicle is selected by unknown processes to be the follicle that will release the oocyte at ovulation.

The midcycle rise in plasma estradiol stimulates the large midcycle LH surge. This midcycle LH surge triggers resumption of meiosis within the oocyte and luteinization of the granulosa cells within the preovulatory follicle. Immediately before ovulation, the outer follicular wall begins to dissolve and an oocyte is released approximately 24 to 36 hours from the onset of the LH surge.

After ovulation, granulosa cells and the surrounding theca cells enlarge, accumulate lipid, and become transformed into lutein cells. This begins the luteal phase of the menstrual cycle. These cells form a new vascularized structure called the corpus luteum, which secretes estradiol and progesterone. LH maintains the corpus luteum during the luteal phase and, acting via the adenyl cyclase system, stimulates progesterone production. If pregnancy does not occur, lutein cells degenerate, and diminished hormone secretion precedes menstruation. Menstruation is immediately followed by the onset of another menstrual cycle.

Because endometrial proliferation serves to prepare the uterus for an impending pregnancy, manipulation of hormones and of the uterine environment can provide contraception. For example, estrogens are known to decrease FSH secretion by feedback inhibition. Under certain circumstances, estrogens can also inhibit LH secretion, once again by negative feedback. Under normal circumstances, the spike of circulating estrogen found just prior to ovulation induces the surge of gonadotropic hormones that occurs just prior to and results in ovulation. High doses of estrogen immediately post-coitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits luteinizing hormone secretion and blocks ovulation in humans.

The most prevalent form of oral contraception is a pill that combines both an estrogen and a progestin, a so-called combined oral contraceptive preparation. Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et al., *Contraception* 25: 243 (1982)).

Whereas the conventional 21 day pill packs with a 7 day "pill free" or placebo interval worked well when oral contraceptives were of higher dosage, as the doses have come down, for both the estrogen and progestin components, bleeding problems have increased in frequency, especially in the early months of oral contraceptive use, but even persistently so in some patients.

There exists a need for contraceptives that reduce bleeding problems and/or have additional benefits for women.

SUMMARY OF THE INVENTION

The invention is directed to a method of reducing breakthrough bleeding in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of inducing regular, predictable withdrawal bleeding in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of reducing frequency of onset of a menstrual cycle or withdrawal bleed in a female in need of delayed or reduced menstruation, the method comprising administering to the female a combination of estrogen and progestin for a period of about 81 to about 110 consecutive days, followed by administration of estrogen for a period of about 2 to about 10 consecutive days.

The invention is directed to a method of inducing amenorrhea in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of minimizing uterine bleeding in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of treating an ovarian cyst, uterine leiomyoma (fibroid tumor), or treating Polycystic Ovarian Disease in a female in need thereof, the method comprising administering to the female a combination of estrogen and progestin for a period of more than 20 consecutive days, followed by administration of estrogen for a period of about 2 to about 10 consecutive days.

The invention is directed to a method of treating hirsutism in a female in need thereof, the method comprising administering to the female a combination of estrogen and progestin for a period of more than 20 consecutive days, followed by administration of estrogen for a period of about 2 to about 10 consecutive days.

The invention is directed to a method of decreasing risk of iron deficiency anemia in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of treating a menstrual disorder in a female in need thereof, the method comprising administering to the female a combination of estrogen and progestin for a period of about 81 to about 110 consecutive days, followed by administration of estrogen for a period of about 2 to about 10 consecutive days.

The invention is directed to a method of treating acne in a female in need thereof, the method comprising administering to the female a combination of estrogen and progestin for a period of more than 20 consecutive days, followed by administration of estrogen for a period of about 2 to about 10 consecutive days.

The invention is directed to a method of treating endometriosis in a female in need thereof, the method comprising administering to the female a combination of estrogen and progestin for a period of more than 20 consecutive days, followed by administration of estrogen for a period of about 2 to about 10 consecutive days.

The invention is directed to a method of reducing the risk of endometrial cancer in a female in need thereof, the method comprising administering to the female a combination of estrogen and progestin for a period of more than 20 consecutive days, followed by administration of estrogen for a period of about 2 to about 10 consecutive days.

The invention is directed to a method of reducing the risk of ovarian cancer in a female in need thereof, the method comprising administering to the female a combination of estrogen and progestin for a period more than 20 consecutive days, followed by administration of estrogen for a period of about 2 to about 10 consecutive days.

The invention is directed to a method of treating breast disease in a female in need thereof, the method comprising administering to the female a combination of estrogen and progestin for a period of more than 50 consecutive days, followed by administration of estrogen for a period of about 2 to about 10 consecutive days.

The invention is directed to a method of reducing the risk of colorectal cancer in a female in need thereof, the method comprising administering to the female a combination of estrogen and progestin for a period more than 20 consecutive days, followed by administration of estrogen for a period of about 2 to about 10 consecutive days.

The invention is directed to a method of treating an infection in a female in need thereof, the method comprising administering to the female a combination of estrogen and progestin for a period of more than 20 consecutive days, followed by administration of estrogen for a period of about 2 to about 10 consecutive days.

The invention is directed to a method of treating temporomandibular disorder in a female in need thereof, the method comprising administering to the female a combination of estrogen and progestin for a period of more than 20 consecutive days, followed by administration of estrogen for a period of about 2 to about 10 consecutive days.

The invention is directed to a method of treating a catamenial symptom in a female in need thereof, the method comprising administering to the female a combination of estrogen and progestin for a period of more than 20 consecutive days, followed by administration of estrogen for a period of about 2 to about 10 consecutive days.

The invention is directed to a method of treating non-menstrual related headache in a female in need thereof, the method comprising administering to the female a combination of estrogen and progestin for a period of more than 20 consecutive days, followed by administration of estrogen for a period of about 2 to about 10 consecutive days.

The invention is directed to a method of treating non-menstrual related nausea in a female in need thereof, the method comprising administering to the female a combination of estrogen and progestin for a period of more than 20 consecutive days, followed by administration of estrogen for a period of about 2 to about 10 consecutive days.

The invention is directed to a method of treating non-menstrual related depression in a female in need thereof, the method comprising administering to the female a combination of estrogen and progestin for a period of more than 20 consecutive days, followed by administration of estrogen for a period of about 2 to about 10 consecutive days.

The invention is directed to a method of increasing contraceptive effectiveness in a higher weight female in need thereof, the method comprising administering to the female a combination of estrogen and progestin for a period of more than 50 consecutive days, followed by administration of estrogen for a period of about 2 to about 10 consecutive days; wherein the higher weight female weighs about 70 kg or more.

The invention is directed to a method of increasing fertility in a female in need thereof, the method comprising (i) administration to the female of a combination of estrogen and progestin for a period of more than 20 consecutive days, followed by administration of estrogen for a period of about 2 to about 10 consecutive days; (ii) discontinuation of administration of the combination of estrogen and progestin for the period of more than 20 consecutive days and of estrogen for the period of about 2 to about 10 consecutive days; and (iii) optional administration to the female of an ovulation-inducing agent during the discontinuation of administration of the combination of estrogen and progestin for the period of more than 20 consecutive days and of estrogen for the period of about 2 to about 10 consecutive days.

The invention is directed to a method of treating or diminishing a perimenopausal symptom in a female in need thereof, the method comprising administering to the female a combination of estrogen and progestin for a period of more than 20 consecutive days, followed by administration of estrogen for a period of about 2 to about 10 consecutive days.

The invention is directed to a method for treating a condition resulting from menopausal estrogen decline in a menopausal female, the method comprising administering to the female a combination of estrogen and progestin for a period of more than 20 consecutive days, followed by administration of estrogen for a period of about 2 to about 10 consecutive days.

The invention is directed to a method of treating hypoestrogenism in a female in need thereof, the method comprising administering to the female a combination of estrogen and progestin for a period of more than 20 consecutive days, followed by administration of estrogen for a period of about 2 to about 10 consecutive days.

The invention is directed to a method of treating a menopausal disorder in a female in need thereof, the method comprising administering to the female a combination of estrogen and progestin for a period of more than 20 consecutive days, followed by administration of estrogen for a period of about 2 to about 10 consecutive days.

The invention is directed to a method of maintaining bone density or preventing loss of bone density in a female in need thereof, the method comprising administering to the female a combination of estrogen and progestin for a period of more than 20 consecutive days, followed by administration of estrogen for a period of about 2 to about 10 consecutive days.

The invention is directed to a method of treating a female in need of hormone replacement therapy, the method comprising administering to the female a combination of estrogen and progestin for a period of more than 20 consecutive days, followed by administration of estrogen for a period of about 2 to about 10 consecutive days.

The invention is further directed to each of the methods listed above, wherein an antidepressant is administered (i) in combination with the estrogen for the period of about 2 to about 10 consecutive days, (ii) continuously, (iii) intermittently, (iv) one time during the menstrual cycle, or (v) once weekly.

The invention is further directed to each of the methods listed above, wherein the estrogen that is administered in combination with progestin for a period of more than 20 consecutive days or for more than 50 consecutive days is administered in a daily amount equivalent to about 5 µg to about 50 µg of ethinyl estradiol, and the progestin that is administered in combination with estrogen for a period of more than 20 consecutive days or for more than 50 consecutive days is administered in a daily amount equivalent to about 0.05 mg to about 1.5 mg of levonorgestrel. The invention is also directed to each of the methods listed above, wherein the estrogen that is administered for a period of about 2 to about 10 days is administered in a daily amount equivalent to about 5 µg to about 50 µg of ethinyl estradiol.

The invention is further directed to each of the methods listed above, wherein the combination of estrogen and progestin is administered for a period of 60 to 110 consecutive days, for a period of 81 to 110 consecutive days, for a period of 81 to 89 consecutive days, or for a period 21 to 26 consecutive days.

The invention is also directed to each of the methods listed above, wherein the female is a perimenopausal female or a menopausal female.

BRIEF DESCRIPTION OF THE DRAWINGS

FIG. 6 also shows the plasma concentration of FSH up to about 56 days (Day 147) after completion of administration, during which no hormone was administered to the patients.

FIG. 7 also shows the plasma concentration of estradiol up to about 56 days (Day 147) after completion of administration, during which no hormone was administered to the patients.

FIG. 8 also shows the plasma concentration of LH up to about 56 days (Day 147) after completion of administration, during which no hormone was administered to the patients.

FIG. 9 also shows the plasma concentration of free testosterone up to about 56 days (Day 147) after completion of administration, during which no hormone was administered to the patients.

FIG. 10 shows the plasma concentration of total testosterone in patients during daily administration of levonorgestrel (0.150 mg)/ethinyl estradiol (0.030 mg) tablets for 84 consecutive days, followed by daily administration of ethinyl estradiol (0.030 mg) tablets for 7 days, as described in Example 10. FIG. 10 also shows the plasma concentration of total testosterone up to about 56 days (Day 147) after completion of administration, during which no hormone was administered to the patients.

DETAILED DESCRIPTION OF THE INVENTION

Figure 1:
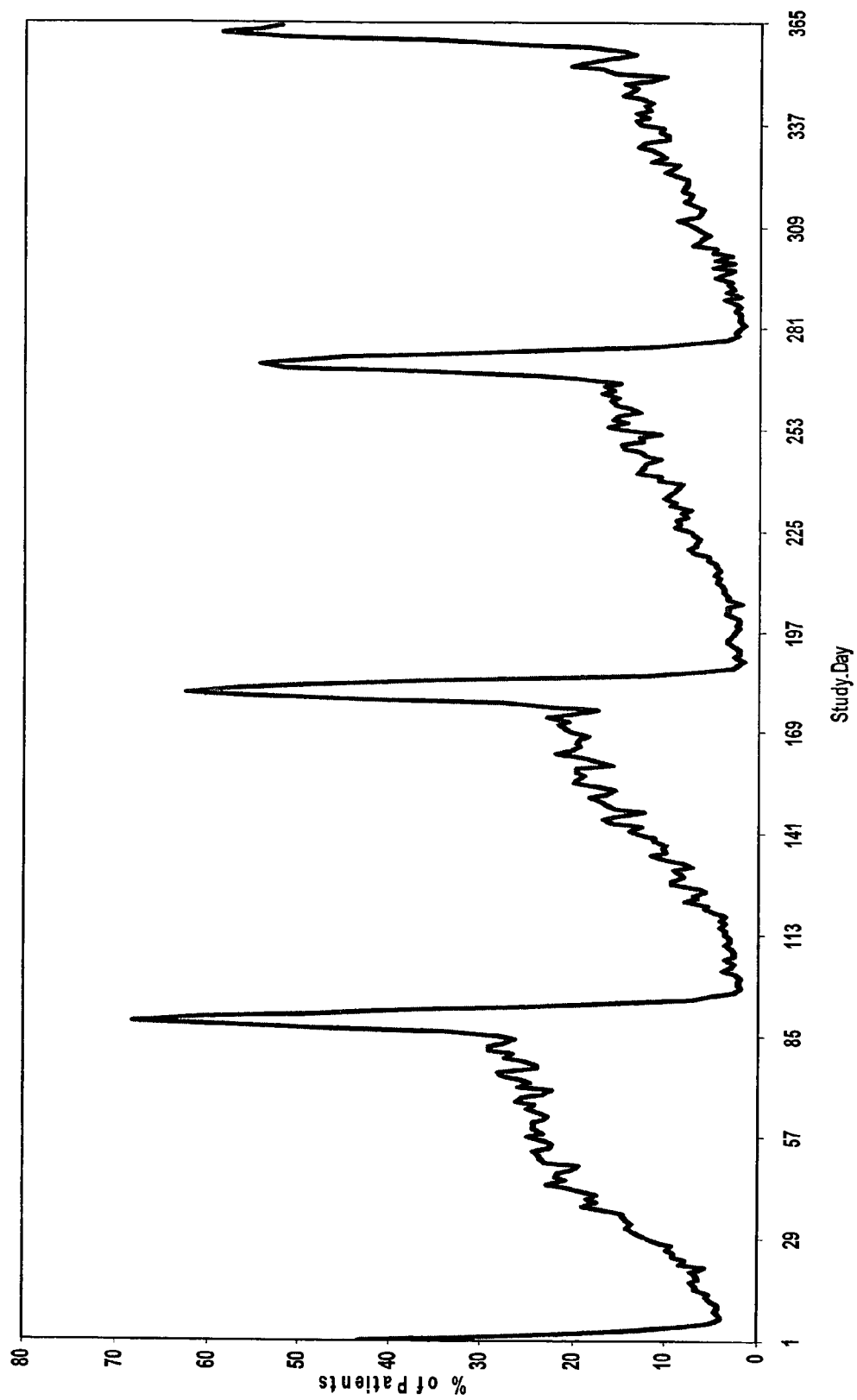
FIG. 1 shows the distribution of bleeding and spotting reported by patients administered the DP3-84/30 regimen during the first clinical study described in Example 7.

The present invention provides estrogen/progestin contraceptive regimens that are useful in the treatment of a variety of conditions and disorders occurring in females of child-bearing age, in peri-menopausal females, and/or in menopausal females.

In accordance with the present invention, a female is administered an estrogen/progestin contraceptive regimen of a combined dosage form of estrogen and progestin (or progestogen) for a period of more than 20 consecutive days, followed by administration of estrogen for a period of about 2 to about 10 days, in which the daily dosage amounts of estrogen and progestin are equivalent to about 5 µg to about 50 µg of ethinyl estradiol and equivalent to about 0.02 mg to about 1.5 mg of levonorgestrel, respectively ("bridged regimen").

In some aspects of the invention, the daily dosage amount of estrogen is equivalent to about 5 µg to about 25 µg of ethinyl estradiol. In other aspects of the invention, the daily dose of estrogen is equivalent to about 25 µg to about 40 µg of ethinyl estradiol. In yet other aspects of the invention, the daily dose of estrogen is equivalent to about 10 µg to about 30 µg of ethinyl estradiol. In some aspects of the invention, the daily dose of estrogen is equivalent to about 20 µg of ethinyl estradiol. In other aspects, it is equivalent to about 30 µg of ethinyl estradiol.

In some aspects of the invention, the daily dosage amount of progestin is equivalent to about 0.01 mg to about 0.25 mg of levonorgestrel. In other aspects of the invention, the daily dose of progestin is equivalent to about 0.05 mg to about 0.20 mg of levonorgestrel. In yet other aspects of the invention, the daily dose of progestin is equivalent to about 0.1 mg of levonorgestrel. In some aspects, it is equivalent to about 0.15 mg levonorgestrel.

In some aspects of the invention, the combined dosage form of estrogen and progestin is administered for more than 20 consecutive days, or is administered for more than 50 consecutive days. In other aspects of the invention, the combined dosage form is administered for about 21 to about 26 consecutive days, for about 22 to about 25 consecutive days, or is administered for about 25 to about 26 consecutive days. In some aspects of the invention, the combined dosage form is administered for about 25 consecutive days. In yet other aspects of the invention, the combined dosage form is administered for about 60 to about 110 consecutive days, or, alternatively, for about 81 to about 110 consecutive days, or for about 81 to about 89 consecutive days. In some aspects of the invention, the period of administration can be at least 81 consecutive days, or at least 84 consecutive days. In other aspects of the invention, the period of administration can be about one year, more than one year but less than two years, two years, or more than two years.

The extended estrogen/progestin contraceptive regimen of the invention refers to the bridged regimen disclosed herein in which a combined dosage form of estrogen and progestin (or progestogen) is administered to a female for a period of more than 50 consecutive days, followed by administration of estrogen for a period of about 2 to about 10 days, in which the daily dosage amounts of estrogen and progestin are equivalent to about 5 µg to about 50 µg of ethinyl estradiol and equivalent to about 0.02 mg to about 1.5 mg of levonorgestrel, respectively ("bridged extended cycle regimen").

In the disclosed bridged regimen, the combined dosage form of estrogen and progestin can be administered monophasically, biphasically, triphasically, or multiphasically. As used herein, "monophasic" refers to the continuous use of one particular dose of estrogen and progestin during the period of administration of the combined dosage form of estrogen and progestin. "Biphasic" refers to administration of a first continuous dose of estrogen and progestin during a first portion of the period of administration of the combined dosage form of estrogen and progestin, with administration of a second continuous dose of estrogen and progestin during the second portion of the period of administration of the combined dosage form. "Triphasic" refers to administration of first, second, and third continuous doses of estrogen and progestin during the first, second, and third portions, respectively, of the period of administration of the combined dosage form of estrogen and progestin. "Multiphasic" refers to administration of four or more continuous doses of estrogen and progestin during the first, second, third, and fourth or more portions, respectively, of the period of administration of the combined dosage form of estrogen and progestin.

The period of administration of the combined dosage form of estrogen and progestin is followed by administration of estrogen for a period of about 2 to about 10 consecutive days ("unopposed estrogen interval"). In other aspects of the invention, the unopposed estrogen interval is about 5 to about 8 consecutive days, about 2 to about 7 consecutive days, or about 3 to about 7 consecutive days. In yet other aspects, it is about 7 days. In some aspects of the invention, the unopposed estrogen interval is about 2 to about 5 consecutive days, or about 2 to about 3 consecutive days. In some aspects of the invention, the unopposed estrogen interval is about 3 days.

The daily dosage amount of estrogen administered during the unopposed estrogen interval is equivalent to about 5 µg to about 50 µg of ethinyl estradiol. In some aspects of the invention, the daily dosage amount of estrogen is equivalent to about 5 µg to about 25 µg of ethinyl estradiol. In other aspects of the invention, the daily dose of estrogen is equivalent to about 10 µg to about 40 µg of ethinyl estradiol, or is equivalent to about 20 µg to about 40 µg of ethinyl estradiol. In some aspects, it is equivalent to about 30 µg of ethinyl estradiol. In yet other aspects of the invention, the daily dose of estrogen is equivalent to about 5 µg to about 15 µg of ethinyl estradiol. In other aspects of the invention, the daily dose of estrogen is equivalent to about 10 µg of ethinyl estradiol.

For example, on a schedule of 84 consecutive days of administration of estrogen and progestin, followed by 7 consecutive days of administration of estrogen, there are only four treatments and menstrual cycles per year. As another example, on a schedule of 177 consecutive days of administration of estrogen and progestin, followed by 7 consecutive days of administration of estrogen, there are only two treatments and menstrual cycles per year. In yet another example, on a schedule of 25 consecutive days of administration of estrogen and progestin, followed by 3 consecutive days of administration of estrogen, there are thirteen treatments and menstrual cycles per year.

The bridged regimen is optionally administered with an antidepressant. In some aspects of the invention, the antidepressant is administered in combination with estrogen during the unopposed estrogen interval of the bridged regimen. In other aspects of the invention, the antidepressant is administered continuously throughout the regimen, or, in yet other aspects of the invention, the antidepressant is administered intermittently. For example, in one aspect of the invention, the antidepressant is administered intermittently during the late luteal phase, which is typically one to two weeks before menses. In yet other aspects of the invention, the antidepressant is administered one time during a menstrual cycle, or once weekly.

The bridged regimen, or the bridged extended cycle regimen, disclosed herein can be used as a method of female contraception. Thus, the invention is directed to a method of contraception in a female in need thereof by administering to the female the bridged regimen, or the bridged extended cycle regimen, disclosed herein. The female can be, for example, of childbearing age or peri-menopausal.

However, the bridged regimen, or the bridged extended cycle regimen, is also useful as a method of treating a variety of conditions and disorders in females. Thus, the bridged regimen, or the bridged extended cycle regimen, can be used as a method of providing contraception to a female for the treatment of a condition or disorder, or as a method of providing contraception and treating a condition or disorder in a female. Such conditions and disorders are described below and include, but are not limited to: breakthrough bleeding; irregular withdrawal bleeding; menstrual bleeding disorders; symptoms associated with an ovarian cyst, uterine leiomyoma (fibroid tumor), and/or Polycystic Ovarian Syndrome; hirsutism; iron deficiency anemia; menstrual disorders; acne; endometriosis; endometrial cancer; ovarian cancer; benign breast disease; infections; ectopic pregnancy; temporomandibular disorder; catamenial symptoms; non-menstrual related headache, nausea, and/or depression; peri-menopausal symptoms; hypoestrogenism; menopausal disorders; and loss of bone density.

The invention, therefore, is also directed to a method of providing contraception to a female for the treatment of a condition or disorder, wherein the female is in need of treatment for the condition or disorder, by administering to the female the bridged regimen, or the bridged extended cycle regimen, disclosed herein. The female can be, for example, of childbearing age, peri-menopausal, or menopausal.

The invention is also directed to a method of providing contraception and treating a condition or disorder in a female, wherein the female is in need of both contraception and treatment of the condition or disorder, by administering to the female the bridged regimen, or the bridged extended cycle regimen, disclosed herein. The female can be, for example, of childbearing age or peri-menopausal.

The bridged regimen or bridged extended cycle regimen disclosed herein includes administration to a female beginning at Day 1 of a menstrual cycle that is defined as beginning at the first day of menstrual flow. Alternatively, the bridged regimen or bridged extended cycle regimen disclosed herein can also include administration to a female beginning at Day 1 of a menstrual cycle that is defined as beginning with the day after the ending of the menstrual flow. Alternatively, the bridged regimen or bridged extended cycle regimen disclosed herein also can include administration to a female beginning at Day 1 of a menstrual cycle that is defined as beginning with any day within the menstrual cycle.

As used herein, "female" refers to any animal classified as a mammal, including humans and non-humans, such as, but not limited to, domestic and farm animals, zoo animals, sports animals, and pets.

"Peri-menopausal female" refers to a woman who has not yet definitely arrived at menopause but who is experiencing symptoms associated with menopause. "Peri-menopause" means "about or around the time of menopause." It encompasses the years preceding the last menstrual period during which ovarian function declines and ultimately ceases and can include the presence of symptoms and irregular cycles. "Menopausal female" refers to a woman who has definitely arrived at menopause and may be experiencing symptoms associated with menopause. Menopause or post-menopause is the permanent cessation of menstruation after the loss of ovarian activity and is generally defined clinically as the absence of menstruation for about one year. Menopause may occur naturally in a woman or it may be artificially induced, e.g., through surgical or chemical means. For example, removal of the ovaries, which can occur, e.g., through hysterectomy, frequently leads to symptoms associated with menopause.

The terms "treat" and "treatment" refer to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The term "continuous" or "consecutive" in reference to "administration" means that the frequency of administration is at least once daily. Note, however, that the frequency of administration can be greater than once daily and still be "continuous," e.g., twice or even three times daily, as long as the dosage levels as specified herein are not exceeded.

The term "dosage level," "daily dosage amount," or "daily dose" means the total amount of estrogen or progestin administered per day. Thus, for example, "continuous administration" of a progestin to a woman at a "dosage level" of 30 µg means that the woman receives a total of 30 µg of progestin on a daily basis, whether the progestin is administered as a single 30 µg dose or, e.g., three separate 10 µg doses. A conventional means of continuously administering an estrogen or progestin is as a single daily oral dose at the prescribed dosage level.

For each of the disclosed methods of the invention, the effect of administration of the bridged regimen, and/or bridged extended cycle regimen, with respect to the specified condition (e.g., inducing the specified condition in the female, reducing the occurrence of the condition, minimizing the condition, or treating the condition or disorder) can be evaluated in comparison to each other, to the condition or disorder exhibited by the female after administration of a standard 28-day contraceptive regimen other than the disclosed bridged regimen, after administration of an extended cycle contraceptive regimen other than the disclosed bridged extended cycle regimen, and/or after administration of no contraceptive regimen. For example, the effect of administering the bridged regimen to treat a menstrual bleeding disorder can be evaluated by comparing the occurrence and/or severity of the bleeding disorder in females suffering from the disorder who have been administered the bridged regimen with the occurrence and/or severity of the bleeding disorder in females suffering from the disorder who have not been treated with a contraceptive regimen, or with females suffering from the disorder who have been administered a contraceptive regimen not disclosed in the present invention. The effect of administering the bridged regimen and/or bridged extended cycle regimen of the invention can also be evaluated by comparing the occurrence and/or severity of a condition in a female before and after administration of the bridged regimen and/or bridged extended cycle regimen of the invention, or by evaluating the condition of the female during the course of one or more cycles.

When the period of continuous administration of estrogen and progestin, which in some aspects of the invention is more than 50 consecutive days, is followed by administration of estrogen for a period of about 2 to about 10 consecutive days, the bridged regimen is characterized by a reduced incidence of breakthrough or unscheduled bleeding. It has been observed that the incidence of breakthrough bleeding decreases with continued use of the disclosed bridged extended cycle regimen so that by the fourth cycle, it is comparable to that observed with the traditional 28-day regimen. Further continued use of the bridged extended cycle regimen can lead to even further reduction in the incidence of breakthrough bleeding. Thus, the present invention is directed to a method of reducing breakthrough bleeding in a female in need thereof by administering to the female the bridged regimen, or the bridged extended cycle regimen, disclosed herein. The female can be, for example, of childbearing age or peri-menopausal.

The invention is also directed to a method of providing contraception and reducing breakthrough bleeding in a female in need thereof by administering to the female the bridged regimen, or the bridged extended cycle regimen, disclosed herein. For example, the female can be of childbearing age or peri-menopausal.

The invention is directed to a method of inducing regular, predictable withdrawal bleeding in a female in need thereof by administering to the female the bridged regimen, or the bridged extended cycle regimen, disclosed herein. The female can be, for example, of childbearing age or peri-menopausal. Administration of the bridged regimen is useful in controlling menstrual cycles in a female by inducing regular, predictable withdrawal bleeding. By suppressing ovulation and delivering estrogen and progesterone in a programmed fashion, the bridged regimen can establish or restore synchrony to the endometrium. This is particularly useful in the treatment of heavy or intermenstrual bleeding. The resulting predictable timing and shorter duration of bleeding are especially advantageous to peri-menopausal women, who often experience irregular menstrual cycles.

The invention is also directed to a method of providing contraception and inducing regular, predictable withdrawal bleeding in a female in need thereof by administering to the female the bridged regimen, or the bridged extended cycle regimen, disclosed herein. The female can be, for example, a female of childbearing age or a peri-menopausal female.

The invention is directed to a method of reducing frequency or delaying onset of a menstrual cycle in a female in need of delayed or reduced menstruation by administering to the female the bridged regimen, or the bridged extended cycle regimen, disclosed herein. The female can be, for example, of childbearing age or peri-menopausal. For example, particular groups or subpopulations of women can benefit from reduced menstruation, such as women enlisted in the U.S. military and women athletes. Control of the menstrual cycle, or even induction of amenorrhea using the extended bridged cycle regimen, can be an advantage for women on active duty. The non-contraceptive benefits resulting from use of the bridged extended cycle regimen, such as reduction in dysmenorrhea, premenstrual syndrome, menorrhagia, iron deficiency anemia, and ability to control timing of withdrawal bleeding, can be desirable and advantageous to women athletes as well. The term "amenorrhea" refers to the absence of bleeding during one or more menstrual cycles of a female. The term encompasses the absence of bleeding and/or spotting during the unopposed estrogen interval of the bridged regimen of the present invention when administered to a female, as well as the absence of bleeding or spotting throughout an entire menstrual cycle during administration of the bridged regimen.

The invention is also directed to a method of providing contraception and reducing frequency or delaying onset of a menstrual cycle in a female in need thereof by administering to the female the bridged regimen, or the bridged extended cycle regimen, disclosed herein. The female can be, for example, a female of childbearing age or a peri-menopausal female.

The invention is directed to a method for minimizing uterine bleeding in a female in need thereof by administering to the female the bridged regimen, or the bridged extended cycle regimen, disclosed herein. The female can be, for example, of childbearing age or peri-menopausal. By diminishing endometrial proliferation, administration of estrogen and progestin in the bridged regimen can reduce the volume and duration of menstrual flow. A female on the disclosed bridged extended regimen experiences fewer total scheduled days of bleeding than a female on a traditional 28-day regimen, and experiences less blood loss, because the bridged extended cycle regimen involves fewer stop/start transitions per year. The female to be treated can exhibit abnormal uterine bleeding, including, for example, menorrhagia. As used herein, "abnormal uterine bleeding" refers to an abnormal duration of bleeding (i.e., greater than about 7 days of bleeding, or hypermenorrhea), abnormal amount of bleeding (i.e., greater than about 80 mL blood loss during menses, or menorrhagia), increased frequency of bleeding (i.e., less than about 22 days between menstrual cycles, or polymenorrhea), or any combinations thereof.

The invention is also directed to a method of providing contraception and minimizing uterine bleeding in a female in need thereof by administering to the female the bridged regimen, or the bridged extended cycle regimen, disclosed herein. The female can be, for example, a female of childbearing age or a peri-menopausal female.

The invention, moreover, is directed to a method of treating a menstrual bleeding disorder in a female in need thereof by administering to the female the bridged regimen, or the bridged extended cycle regimen, disclosed herein. The female can be, for example, of childbearing age or peri-menopausal.

The invention is also directed to a method of providing contraception and treating a menstrual bleeding disorder in a female in need thereof by administering to the female the bridged regimen, or the bridged extended cycle regimen, disclosed herein. The female can be, for example, a female of childbearing age, or a peri-menopausal female.

The invention is directed to a method of treating symptoms associated with ovarian cysts, uterine leiomyomas (fibroids), or Polycystic Ovarian Syndrome in a female in need thereof by administering to the female the bridged regimen, or the bridged extended cycle regimen, disclosed herein. The female can be, for example, of childbearing age, peri-menopausal, or menopausal. The invention is also directed to a method of providing contraception and treating symptoms associated with ovarian cysts, uterine leiomyomas (fibroids), or Polycystic Ovarian Syndrome in a female in need thereof by administering to the female the bridged regimen, or the bridged extended cycle regimen, disclosed herein. The female can be, for example, a female of childbearing age or peri-menopausal.

Ovarian cysts, uterine leiomyomas (fibroids), or Polycystic Ovarian Syndrome can cause symptoms including, but not limited to, pelvic pain, dysmenorrhea, abnormal uterine bleeding, acne, and hirsutism. In the invention, such symptoms can be treated by administration of the bridged regimen, or the bridged extended cycle regimen, described herein.

Ovarian cysts arise from functional cysts that commonly occur around mid-cycle, when a follicle destined to become an egg fails to mature. Instead of leaving the ovary in a process known as ovulation, it remains inside, floating in a tiny sac of fluid. It is that sac that eventually forms into a cyst. Although rarely malignant, ovarian cysts lead to 200,000 hospitalizations in the United States each year. For some women, some studies have shown that the cysts develop cycle after cycle. Though ovarian cysts can sometimes be asymptomatic, they can also cause pain (constant pelvic pain, pain during intercourse, pain during pelvic movement, and/or pain before or after menses), abnormal bleeding (lengthened, shortened, irregular and/or absent menses), and/or abdominal bloating or distension.

Uterine fibroids are benign growths of uterine muscle that sometimes exist singly, but most often are multiple and range in size from microscopic to filling most of the lower abdominal cavity. Many women with fibroids have no symptoms at all. For those that do, the most common complaints are pressure symptoms and heavy, prolonged periods. There may be pressure in the pelvic region from the enlarged uterus, and the resulting symptoms are often related to where the fibroid is exerting pressure (e.g., increased urinary frequency, constipation or difficulty with bowel movements). The pressure can also cause backache, lower abdominal discomfort, and pain during and after intercourse. Fibroids can cause very heavy and prolonged periods, leading to iron-deficiency anemia, as well as painful periods (secondary dysmenorrhea). The presence of fibroids can also cause reproductive problems such as infertility, multiple miscarriages, premature labor, or labor complications.

The term "ovarian cyst" as used above represents more singular occurrences caused by the failure of an egg to mature. Polycystic Ovarian Syndrome (PCOS), in contrast, is due to an abnormal production of LH (luteinizing hormone) and FSH (follicle stimulating hormone) by the pituitary gland. An imbalance of these hormones stops egg production and increases production of androgens, with the ovaries producing higher levels of testosterone and estrogens. This results in ovaries "peppered" with empty egg follicles that become inflamed cysts, irregular or stopped periods (which in turn causes infertility), excess body hair growth, and acne on the face and body. PCOS often leads to obesity, diabetes and hypertension.

Polycystic Ovarian Syndrome is the cause of most cases of androgen-dependent hirsutism. See Rittmaster, R. S., *Lancet* 349: 191-195 (1997). Hirsutism can be described as the growth of excessive hair in women on parts of the body where excessive hair is generally not present, e.g., on the back and chest. Most cases of hirsutism are androgen-dependent, i.e., result from a combination of increased androgen production by the body and increased skin sensitivity to androgens. Normally, small quantities of androgens are produced by the ovaries and the adrenal glands. However, in women suffering from Polycystic Ovarian Syndrome, androgen levels are elevated, which can lead to the development of androgen-dependent conditions such as, for example, pronounced forms of acne (e.g., acne papulopustulosa), androgenetic alopecia and mild forms of hirsutism. Oral contraceptives can suppress the ovarian production of androgens and are thus useful in the treatment of these androgen-dependent conditions.

Thus, the invention is also directed to a method of treating hirsutism in a female in need thereof, by administering to the female the bridged regimen, or the bridged extended cycle regimen, disclosed herein. The female can be, for example, of childbearing age, peri-menopausal, or menopausal.

The invention is also directed to a method of providing contraception and treating hirsutism in a female in need thereof, by administering to the female the bridged regimen, or the bridged extended cycle regimen, disclosed herein. The female can be, for example, a female of childbearing age or peri-menopausal.

The invention is directed to a method of treating alopecia in a female in need thereof, by administering to the female the bridged regimen, or the bridged extended cycle regimen, disclosed herein. The female can be, for example, of childbearing age, peri-menopausal, or menopausal. The invention is also directed to a method of providing contraception and treating alopecia in a female in need thereof, by administering to the female the bridged regimen, or the bridged extended cycle regimen, disclosed herein. The female can be, for example, a female of childbearing age or peri-menopausal.

The invention is further directed to a method of decreasing risk of iron deficiency anemia in a female in need thereof by administering to the female the bridged regimen, or the bridged extended cycle regimen, disclosed herein. The female can be, for example, of childbearing age or peri-menopausal. The reduction in the volume and duration of menstrual flow that results from administration of, e.g., the bridged extended cycle regimen can lead to a reduction in the total loss of blood, thus improving the body's iron stores and reducing the morbidity associated with menorrhagia. This effect is particularly desirable in women with coagulation disorders, for example, von Willebrand's disease. The female to be treated can be, but is not limited to, a peri-menopausal female.

The invention is also directed to a method of providing contraception and decreasing risk of iron deficiency anemia in a female in need thereof by administering to the female the bridged regimen, or the bridged extended cycle regimen, disclosed herein. The female can be, for example, a female of childbearing age or a peri-menopausal female.

The invention is directed to a method of treating a menstrual disorder in a female in need thereof by administering to the female the bridged regimen, or the bridged extended cycle regimen, disclosed herein. The female can be, for example, of childbearing age or peri-menopausal. Menstrual disorders include, but are not limited to, irregular menstrual cycles, dysmenorrhea (painful menstruation), mittelschmerz, and dysfunctional uterine bleeding, as well as premenstrual symptoms such as, but not limited to, those associated with premenstrual syndrome (PMS) or Premenstrual Dysphoric Disorder (PMDD).

The invention is also directed to a method of providing contraception and treating a menstrual disorder in a female in need thereof by administering to the female the bridged regimen, or the bridged extended cycle regimen, disclosed herein. The female can be, for example, a female of childbearing age or a peri-menopausal female.

During the luteal phase of the menstrual cycle, as many as 75% of women with regular menstrual cycles experience some symptoms of premenstrual syndrome (PMS), a recurring, cyclical disorder involving behavioral, emotional, social and physical symptoms (Steiner et al., *Annu. Rev. Med.* 48: 447-455 (1997)). Behavioral, emotional and social symptoms include, but are not limited to, irritability, mood swings, depression, hostility and social withdrawal. Physical symptoms include, but are not limited to, bloating, breast tenderness, myalgia, migraines or headaches, and fatigue. True PMS only occurs during the luteal phase of the menstrual cycle, with a symptom-free period during the follicular phase. The etiology of PMS is still unknown.

A subgroup of women with PMS, about 2-9%, exhibit symptoms that are primarily related to a severe mood disorder. In these women, the diagnosis of Premenstrual Dysphoric Disorder (PMDD), which is defined in the Fourth edition of the Diagnostic and Statistical Manual of Mental Disorders (DSM-IV) can be applied. According to the DSM-IV, a woman with PMDD must have at least five premenstrual symptoms during the luteal phase, with at least one of the symptoms being an emotional or "core" symptom. The core symptoms must be irritability, anger, mood swings, tension or depression (and interfere with daily activities), and must be confirmed by a prospective daily rating for at least two cycles. Three to five percent of women with PMS report to have PMDD. There is also a subgroup of women who experience severe PMS, which accounts for about 20% of the PMS population. These women experience severe emotional symptoms that do not fall under the strict criteria of PMDD as defined in DSM-IV but require medical attention. U.S. application Ser. No. 10/309,313 relates to the use of estrogen/progestin contraceptive regimens optionally combined with an antidepressant for the treatment of PMS, PMDD, and related conditions.

Suppression of ovulation that results from administration of the extended cycle regimen can also eliminate mid-cycle pain ("mittelschmerz") associated with rupture of the ovarian follicle. Additionally, suppression of ovulation and delivery of estrogen and progesterone in a regular, predictable schedule, which results from use of the bridged regimen can be beneficial in the treatment of other menstrual disorders such as heavy or intermenstrual bleeding. In some aspects of the invention, the female is, but not limited to, a peri-menopausal female.

The invention is directed to a method of treating acne in a female in need thereof by administering to the female the bridged regimen, or the bridged extended cycle regimen, disclosed herein. The female can be, for example, of childbearing age, peri-menopausal, or menopausal. The bridged regimen is believed to suppress gonadotropin and decrease ovarian and adrenal androgen production, resulting in an improvement in acne of, e.g., women of childbearing age and older.

The invention is also directed to a method of providing contraception and treating acne in a female in need thereof by administering to the female the bridged regimen, or the bridged extended cycle regimen, disclosed herein. The female can be, for example, a female of childbearing age or peri-menopausal.

The invention is directed to a method of treating endometriosis in a female in need thereof by administering to the female the bridged regimen, or the bridged extended cycle regimen, disclosed herein. The female can be, for example, of childbearing age or peri-menopausal. The invention is also directed to a method of providing contraception and treating endometriosis in a female in need thereof by administering to the female the bridged regimen, or the bridged extended cycle regimen, disclosed herein. The female can be, for example, a female of childbearing age or a peri-menopausal female.

In hormonal therapy of endometriosis, endometriotic tissue responds to adverse endocrine environments (low estrogen and/or high progestin concentration). Progestins produce marked atrophy of the endometrium and ectopic endometrial tissue and decrease intraperitoneal inflammation associated with endometriosis. The American College of Obstetrics and Gynecology stated that progestins, alone or in combination with estrogens as oral contraceptives, are an optimal choice for the management of endometriosis in women who desire contraception (American College of Obstetricians and Gynecologists, *ACOG Practice Bulletin No.* 11 (December 1999)). The use of the bridged regimen of the present invention is beneficial for treating or preventing endometriosis.

Chronic pelvic pain often precedes and is associated with the development of endometriosis. Thus, the invention is also directed to a method of treating chronic pelvic pain in a female in need thereof by administering to the female the bridged regimen, or the bridged extended cycle regimen, disclosed herein. The female can be, for example, of childbearing age or peri-menopausal. The invention is also directed to a method of providing contraception and treating chronic pelvic pain in a female in need thereof by administering to the female the bridged regimen, or the bridged extended cycle regimen, disclosed herein. The female can be, for example, a female of childbearing age or a peri-menopausal female.

The invention is further directed to a method of reducing the risk of endometrial cancer in a female in need thereof by administering to the female the bridged regimen, or the bridged extended cycle regimen, disclosed herein. The female can be, for example, of childbearing age, peri-menopausal, or menopausal. The invention is also directed to a method of providing contraception and reducing the risk of endometrial cancer in a female in need thereof by administering to the female the bridged regimen, or the bridged extended cycle regimen, disclosed herein. The female can be, for example, a female of childbearing age or peri-menopausal.

The invention is directed to a method of reducing the risk of ovarian cancer in a female in need thereof by administering to the female the bridged regimen, or the bridged extended cycle regimen, disclosed herein. The female can be, for example, of childbearing age, peri-menopausal, or menopausal. The frequency of ovulation and thereby the frequency of ovarian stimulation can be reduced, suppressed, or eliminated by use of the bridged regimen, in particular, the bridged extended cycle regimen. The female can be, for example, of childbearing age, peri-menopausal, or menopausal. The invention is also directed to a method of providing contraception and reducing the risk of ovarian cancer in a female in need thereof by administering to the female the bridged regimen, or the bridged extended cycle regimen, disclosed herein. The female can be, for example, a female of childbearing age, peri-menopausal, or menopausal.

The invention is further directed to a method of treating benign breast disease, including, but not limited to, fibrocystic breast disease, in a female in need thereof by administering to the female the bridged regimen, or the bridged extended cycle regimen, disclosed herein. The female can be, for example, of childbearing age, peri-menopausal, or menopausal. Roughly a third of all women between the ages of 30 and 50 will be diagnosed with fibrocystic breast disease or other benign breast condition. Other terms for this condition include chronic mastitis (inflammation) and mammary dysplasia.

The invention is also directed to a method of providing contraception and treating benign breast disease in a female in need thereof by administering to the female the bridged regimen, or the bridged extended cycle regimen, disclosed herein. The female can be, for example, a female of childbearing age or peri-menopausal.

The invention is also directed to a method of reducing the risk of colorectal cancer in a female in need thereof by administering to the female the bridged regimen, or the bridged extended cycle regimen, disclosed herein. The female can be, for example, of childbearing age, peri-menopausal, or menopausal. The bridged regimen of the present invention is thought to protect against colorectal cancer as a result of changes in bile synthesis and secretion due to the female hormones in the regimen, which is thought to lead to a reduced concentration of bile acids in the colon. It has also been observed that estrogen inhibits the growth of colon cancer cells in vitro, and estrogen receptors have been identified in normal and neoplastic colon epithelial cells. See Fernandez, E., et al., *British J. Cancer* 84: 722-727 (2001). Thus, the bridged regimen is beneficial in the prevention or reduction in the occurrence of colorectal cancer.

The invention is also directed to a method of providing contraception and reducing the risk of colorectal cancer in a female in need thereof by administering to the female the bridged regimen, or the bridged extended cycle regimen, disclosed herein. The female can be, for example, a female of childbearing age or peri-menopausal.

The invention is directed to a method of preventing or treating an infection in a female in need thereof by administering to the female the bridged regimen, or the bridged extended cycle regimen, disclosed herein. The female can be, for example, of childbearing age, peri-menopausal, or menopausal. For example, sexually transmitted diseases (STDs) are infections caused by a pathogen such as a virus, bacterium, parasite, or fungus, that is spread from person to person through sexual contact. STDs can be painful, irritating, and even life-threatening. The bridged regimen is believed to have a protective role against the development of some STDs because it stimulates the body to produce a thicker cervical mucous, which acts as a barrier to semen carrying bacteria that cause sexually transmitted diseases.

The invention is also directed to a method of providing contraception and treating an infection in a female in need thereof by administering to the female the bridged regimen, or the bridged extended cycle regimen, disclosed herein. The female can be, but is not limited to, a female of childbearing age or peri-menopausal.

Pelvic Inflammatory Disease (PID) is a complication that can result from STD infections. PID is a serious syndrome of the female reproductive tract that results from the spread of infections (most often sexually transmitted infections such as *Chlamydia trachomatis* and *Nisseris gonnorrheoea*) from the vagina and endocervix to the uterus, fallopian tubes and ovaries. PID is commonly manifested as endometritis (infection of the lining of the uterus) or salpingitis (infection of the fallopian tubes), and less commonly as pelvic peritonitis and/or inflammation of contiguous structures. (MacDonald, N. E., and Bowie, W. R., *Canadian Communicable Disease Report* 21S4: 25-33 (1995); Westrom, L. and Mardh, P-A., *Sexually Transmitted Diseases*, $2^{nd}$ Ed., pages 593-613, New York: McGraw-Hill, 1990).

PID is a major cause of infertility and ectopic pregnancy. Ectopic pregnancy results from the implantation of a fertilized ovum in the fallopian tube or in the abdominal cavity and is thought to be caused by ciliary dysfunction within the fallopian tube resulting from prior tubal infection with *N. gonorrhoea* and/or *C. trachomatis*, which often results in loss of ciliated epithelial cells from the fallopian tubes. It has been estimated that prior tubal infection with STD agents causes about 50% of the cases of ectopic pregnancy. (MacDonald, N. E., and Brunham, R., *Canadian Journal of Human Sexuality* 6(2): 161-170 (1997).)

The bridged regimen is believed to have a protective role against the development of PID because it stimulates the body to produce thicker cervical mucous, which helps prevent semen carrying STD-causing bacteria from gaining access to the uterus and eventually causing PID and PID-related complications, such as ectopic pregnancy.

Thus, the bridged regimen of the present invention is useful in the prevention or reduction in occurrence of sexually transmitted diseases, Pelvic Inflammatory Disease, and ectopic pregnancy. Accordingly, the invention is directed to a method of preventing or reducing the occurrence of a sexually transmitted disease or Pelvic Inflammatory Disease in a female in need thereof by administering to the female the bridged regimen, or the bridged extended cycle regimen, disclosed herein. The invention is also directed to a method of preventing ectopic pregnancy in a female in need thereof by administering to the female the bridged regimen, or the bridged extended cycle regimen, disclosed herein. The female can be, but is not limited to, a female of childbearing age or a peri-menopausal female.

The invention is also directed to a method of providing contraception and treating a sexually transmitted disease or Pelvic Inflammatory Disease in a female in need thereof by administering to the female the bridged regimen, or the bridged extended cycle regimen, disclosed herein. The invention, moreover, is directed to a method of providing contraception and preventing ectopic pregnancy in a female in need thereof by administering to the female the bridged regimen, or the bridged extended cycle regimen, disclosed herein. The female can be, but is not limited to, a female of childbearing age or a peri-menopausal female.

In addition, use of the bridged extended cycle regimen, in comparison to the use of a conventional 28-day contraceptive regimen, can lead to a reduction in the reported occurrences of infection such as urinary tract infections, pharyngitis, upper respiratory tract infections, and sinusitus. Thus, the invention is further directed to the prevention or reduction in occurrence of certain infections, such as urinary tract infections, pharyngitis, upper respiratory tract infections, and sinusitus, in a female in need thereof by administering to the female the bridged regimen, or the bridged extended cycle regimen, disclosed herein. The female can be, for example, of childbearing age, peri-menopausal, or menopausal. The invention is also directed to a method of providing contraception and treating certain infections, such as urinary tract infections, pharyngitis, upper respiratory tract infections, and sinusitus, in a female in need thereof by administering to the female the bridged regimen, or the bridged extended cycle regimen, disclosed herein. The female can be, for example, of childbearing age or peri-menopausal.

The invention is also directed to a method of treating temporomandibular disorder in a female in need thereof by administering to the female the bridged regimen, or the bridged extended cycle regimen, disclosed herein. The female can be, for example, of childbearing age, peri-menopausal, or menopausal. Temporomandibular disorders (TMD) are disorders of the jaw muscles, temporomandibular joints, and/or the nerves associated with chronic facial pain. The bridged regimen and the bridged extended cycle regimen of the present invention are useful in the treatment of TMD. The invention is also directed to a method of providing contraception and treating temporomandibular disorder in a female in need thereof by administering to the female the bridged regimen, or the bridged extended cycle regimen, disclosed herein. The female can be, for example, of childbearing age or peri-menopausal.

The invention is directed to a method of treating a catamenial symptom in a female in need thereof by administering to the female the bridged regimen, or the bridged extended cycle regimen, disclosed herein. The female can be, for example, of childbearing age or peri-menopausal. Catamenial symptoms are those associated with conditions, disorders, or diseases that can worsen around the time of menses. Such conditions, disorders, or diseases include, but are not limited to, asthma, rheumatoid arthritis, migraine headaches, seizure disorders or epilepsy, multiple sclerosis, and diabetes. The invention is also directed to a method of providing contraception and treating a catamenial symptom in a female in need thereof by administering to the female the bridged regimen, or the bridged extended cycle regimen, disclosed herein. The female can be, for example, of childbearing age or peri-menopausal.

Arthritis is a prevalent chronic condition in women. Hormonal factors can influence the frequency and severity of arthritis. In some women, arthritis symptoms such as joint stiffness, swelling and pain peak during the postovulatory phase of the menstrual cycle, and cyclic changes in local antibody release, white blood cell subpopulations and altered pain perception have been proposed as possible mechanisms (Case, A. M. and Reid, R. L., *Arch. Intern. Med.* 158: 1405-1412 (1998)). Estrogen administered as a single agent, and as part of a combined oral contraceptive has been reported to benefit some women (Kay, C. R. and Wingrave, S. J., *Lancet* 1: 1437 (1983); Linos, A., et al., *Lancet* 1: 1871 (1978)). Thus, use of the bridged regimen, or the bridged extended cycle regimen, is beneficial as a method of treating a catamenial symptom, such as, e.g., a symptom associated with rheumatoid arthritis, in a female in need thereof.

Approximately 60% of women with migraines report a relationship to menstruation (Case, A. M. and Reid, R. L., *Arch. Intern. Med.* 158: 1405-1412 (1998)). Decreasing levels of estrogen during the late luteal phase of the menstrual cycle or abrupt withdrawal of estrogen as during the non-administration period in women taking oral contraceptives are thought to trigger migraine attacks (Sulak P. J., et al., *Obstet. Gynecol* 95: 261-266 (2000); Kudrow, L., *Headache* 15: 36-49 (1975); Whitty, C. W. M., et al., *Lancet* 1: 856-859 (1966)). Thus, use of the bridged regimen, or the bridged extended cycle regimen, is beneficial as a method of treating a catamenial symptom in a female in need thereof, such as, e.g., a migraine headache in a female.

Catamenial epilepsy refers to seizure disorders that occur or worsen around menstruation. It is believed to result from cyclic alterations in both ovarian hormone levels and drug metabolism (Case, A. M. and Reid, R. L., *Arch. Intern. Med.* 158: 1405-1412 (1998)). Thus, use of the bridged regimen, or the bridged extended cycle regimen, is beneficial as a method of treating a catamenial symptom such as, e.g., a symptom associated with epilepsy, in a female in need thereof.

The invention is directed to a method of treating headache or nausea unrelated to the menstrual cycle in a female in need thereof by administering to the female the bridged regimen, or the bridged extended cycle regimen, disclosed herein. The female can be, for example, of childbearing age, peri-menopausal, or menopausal. Use of the bridged extended cycle regimen, in comparison to the use of a conventional 28-day contraceptive regimen, can lead to a reduction in the reported occurrences of non-menstrual-related headache and nausea. Thus, the disclosed bridged regimen, or the bridged extended cycle regimen, can be used as a method of preventing or treating non-menstrual-related headache and nausea. The invention is also directed to a method of providing contraception and treating headache or nausea unrelated to the menstrual cycle in a female in need thereof by administering to the female the bridged regimen, or the bridged extended cycle regimen, disclosed herein. The female can be, for example, of childbearing age or peri-menopausal.

The invention is directed further to a method of treating depression unrelated to the menstrual cycle in a female in need thereof by administering to the female the bridged regimen, or the bridged extended cycle regimen, disclosed herein. The female can be, for example, of childbearing age, peri-menopausal, or menopausal. "Depression" is a term that is often used to refer to different forms of depressive disorders and includes major depression, bipolar disorder (sometimes called manic-depressive illness), and dysthymia, a less severe form of depression. Major depression is manifested by a combination of symptoms that interfere with the ability to work, study, sleep, eat and enjoy once pleasurable activities. Bipolar disorder, which is not nearly as prevalent as other forms of depressive disorders, is characterized by cycling mood changes. Dysthymia, a less severe type of depression, involves long-term, chronic symptoms that do not disable, but keep one from functioning well or from feeling well. "Depression" also includes the less severe, temporary sadness and loneliness often felt from time to time. Use of the bridged extended cycle regimen, compared to use of a conventional 28-day contraceptive regimen, can lead to a reduction in the reported occurrences of non-menstrual-related depression. Thus, the disclosed bridged regimen, or the bridged extended cycle regimen, can be used as a method of preventing or treating non-menstrual-related depression.

The invention is also directed to a method of providing contraception and treating depression unrelated to the menstrual cycle in a female in need thereof by administering to the female the bridged regimen, or the bridged extended cycle regimen, disclosed herein. The female can be, for example, of childbearing age or peri-menopausal.

The invention is further directed to a method of increasing contraceptive effectiveness in a female in need thereof by administering to the female the bridged regimen, or the bridged extended cycle regimen, disclosed herein. The female can be, but is not limited to, a female of childbearing age or a peri-menopausal female. A female in need of contraceptive effectiveness can be, but is not limited to, a higher weight female. A "higher weight female" refers to a human female weighing about 70 kg or more or having a body mass index (BMI) of greater than about 25. In a recent study of body weight and oral contraceptive failure, women weighing about 70.5 kg or more were reported to have a 60% higher risk of oral contraceptive failure (Holt, V. L., et al., *Obstet. Gynecol.* 99: 820-827 (2002)). In a study utilizing the extended cycle regimen, women who weighed about 70 kg or more experienced the same contraceptive effectiveness as women on the same extended cycle regimen who weighed less than about 70 kg.

Thus, the invention is directed to a method of increasing contraceptive effectiveness in a higher-weight female in need thereof, by administering to the female the bridged regimen, or the bridged extended cycle regimen, disclosed herein. The invention is directed to a method of increasing the contraceptive effectiveness in a human female weighing about 70 kg or more, weighing about 80 kg or more, or weighing about 90 kg or more, by administering to the female the bridged regimen or the bridged extended cycle regimen.

The disclosed bridged regimen, or the bridged extended cycle regimen, can also be used as a method of increasing the contraceptive effectiveness in a human female with a body mass index of greater than about 25, greater than about 30, or greater than about 35. Thus, the invention is also directed to a method of increasing the contraceptive effectiveness in a human female with a body mass index of greater than about 25, greater than about 30, or greater than about 35, by administering to the female the bridged regimen or the bridged extended cycle regimen.

The invention is also directed to a method of increasing fertility in a female in need thereof, by administering to the female the bridged regimen, or the bridged extended cycle regimen, disclosed herein, followed by discontinuation of the regimen and optional administration of an agent to induce ovulation in the female. The female can be, but is not limited to, a female of childbearing age or a peri-menopausal female.

It has been observed clinically that women who are taking oral contraceptives for anovulation often conceive when pills are missed, or shortly after discontinuing oral contraceptive treatment, most likely due to a "rebound effect" occurring in the ovary at least for a short period of time. Suppression of ovarian activity using oral contraceptive pills for 2-6 months may result in decreases in early follicular ovarian androgen production and LH and estradiol levels. Increased androgen levels have been shown to have adverse effects on folliculogenesis. These endocrine changes in the early follicular phase may be responsible for improved ovarian response to clomiphene or other treatments for anovulatory infertility. See Brannigan, E. F., and Estes, M. A., *Am. J. Obstet. Gynecol.* 188: 1424-1430 (2003).

Examples of agents that induce ovulation, and that can be administered following discontinuation of the bridged regimen or the bridged extended cycle regimen of the present invention, include, but are not limited to, menotropins (Follicle Stimulating Hormone (FSH) and Luteinizing Hormone (LH), e.g., Pergonal®) and chlomiphene citrate (Clomid®). The ovulation-inducing agent can be administered during a suitable time as can be determined by one of skill in the art, e.g., a physician. In some aspects of the invention, the ovulation-inducing agent can be administered, e.g., within about one week to about one month, or within about one week to about two weeks, after discontinuation of the bridged regimen of the present invention. In some aspects of the invention, the ovulation-inducing agent is administered, e.g., about 2 to about 10 days, or about 5 to about 9 days after discontinuation of the bridged regimen or bridged extended cycle regimen.

Thus, the invention is directed to a method of increasing fertility in a female in need thereof, the method comprising (i) administration to the female of the bridged regimen, or the bridged extended cycle regimen, disclosed herein; (ii) discontinuation of administration of the bridged regimen, or the bridged extended cycle regimen; and (iii) optional administration to the female of an ovulation-inducing agent during the discontinuation of administration of the bridged regimen, or the bridged extended cycle regimen; wherein fertility in the female is increased.

In some aspects of the invention, the disclosed methods are particularly useful in peri-menopausal women and/or menopausal women. Peri-menopausal and menopausal women frequently experience a large variety of conditions and disorders that have been attributed to estrogen deprivation due to ovarian failure or hypoestrogenism. The duration of these disorders can be extremely variable and include hot flushes which can be devastating in some women and very mild in others. Dryness of the vagina associated with susceptibility to minor infections, and frequently associated with discomfort during intercourse, is another symptom that can be directly related to the decrease in estrogen availability.

In a long-term sense, one of the most health-threatening aspects of menopause is the loss of mineral from bone which can result in a decrease in bone mass (osteoporosis) and generates a serious risk of fractures. For example, evidence exists that there is a six-fold increase in fractures in postmenopausal women as opposed to men of the same age (Garraway et al., *Mayo Clinic Proceedings* 54: 701-707 (1979)). These fractures, of course, carry a high complication rate among older people, a marked increase in disability and general morbidity, and certainly an increased risk of mortality.

Another serious health-threatening aspect of menopause is the impressive loss of protection against heart attacks, which is enjoyed by younger women up to the age of 60, when compared to men of the same age. The steep increase in mean serum cholesterol concentration, which occurs around menopause (during the fourth and fifth decades), can contribute importantly to the progressive increase in death from ischemic heart disease in older women. In the eighth and ninth decades, the incidence of deaths from ischemic heart disease, approaches that of men (Havlik, R. J. and Manning-Feinleid, P. H., NIH Publication No. 79-1610, U.S. Department of HEW (1979)).

Accordingly, the invention is directed to a method for treating conditions, such as the physical conditions described above, resulting from menopausal estrogen decline in a menopausal female by administering the bridged regimen, or the bridged extended cycle regimen, disclosed herein to the female. The invention is also directed to a method for treating conditions, such as the physical conditions described above, resulting from hypoestrogenism in a female by administering the bridged regimen, or the bridged extended cycle regimen, disclosed herein to the female. The invention is further directed to a method for treating conditions, such as the physical conditions described above, resulting from ovarian failure in a female by administering the bridged regimen, or the bridged extended cycle regimen, disclosed herein to the female.

The invention is also directed to a method of providing contraception and treating conditions, such as the physical conditions described above, resulting from hypoestrogenism in a peri-menopausal female in need thereof by administering the bridged regimen, or the bridged extended cycle regimen, disclosed herein to the peri-menopausal female. The invention is further directed to a method of providing contraception and treating conditions, such as the physical conditions described above, resulting from ovarian failure in a peri-menopausal female in need thereof by administering the bridged regimen, or the bridged extended cycle regimen, disclosed herein to the peri-menopausal female.

In addition to the above-mentioned major physical problems, some menopausal and peri-menopausal women experience a large variety of other symptoms ranging from depression, insomnia, and nervousness, to symptoms of arthritis and so forth.

It is generally agreed that estrogen is the most effective agent for the control or prevention of menopausal flushes and vaginal atrophy. It is effective in retarding or preventing the appearance of clinical evidence of osteoporosis. In appropriate doses, when combined with progestin, a favorable effect upon blood lipids can also be seen. Problems with estrogen therapy do exist, however, and have been widely explored and documented in the medical literature. The means by which estrogen has been administered, generally speaking, involves either the use of estrogen alone or estrogen plus a progestin.

Estrogen alone, given in small doses on a continuous basis, is effective in most patients for the control of the above symptoms and problems associated therewith. However, although the vast majority of women taking continuous low-dose estrogen will not have bleeding for many months or even years, there is a distinct risk posed by this routine of silently (i.e., exhibiting no overt symptoms) developing "hyperplasia of the endometrium." This term refers, of course, to an overstimulation of the lining of the uterus which can become pre-malignant, coupled with the possibility that the patient will eventually develop cancer of the uterine lining even under such a low-dose regimen (Gusberg et al., *Obstetrics and Gynaecology* 17: 397-412 (1961)).

Estrogen alone can also be given in cycles, usually 21-25 days on treatment and 5-7 days off treatment. Again, if small doses of estrogen are required to control the symptoms and it is used to this fashion, only about 10% of women will experience withdrawal bleeding between the cycles of actual treatment. However, one must again be concerned by the risk of developing endometrial hyperplasia and by the increased relative risk of developing cancer of the uterus (Research on the Menopause: Report of a W.H.O. Scientific Group, 53-68 (1981)).

The addition of progestin with estrogen, however, as in the bridged regimen disclosed herein, will virtually eliminate the concern about developing endometrial hyperplasia and reduce the risk of developing endometrial carcinoma below that of the untreated general population.

Thus, the invention is directed to a method of treating a menopausal disorder or a peri-menopausal disorder or symptom in a female in need thereof by administering to the female the bridged regimen, or the bridged extended cycle regimen, disclosed herein. The invention is also directed to a method of providing contraception and treating a peri-menopausal disorder or symptom in a peri-menopausal female in need thereof by administering to the female the bridged regimen, or the bridged extended cycle regimen, disclosed herein.

The bridged regimen or the bridged extended cycle regimen can be used as a method of maintaining bone density or preventing loss of bone density in a female. The bridged regimen or bridged extended cycle regimen can also be used in this way by administering calcium and/or vitamin D, e.g., in combination with the administration of estrogen and progestin.

The bridged regimen is not limited to administration to peri-menopausal or menopausal females as a method of maintaining bone density or preventing bone loss. The bridged regimen can also be used in a method of maintaining bone density or preventing bone loss by administration to a female of childbearing age that is not peri-menopausal or menopausal. For example, the bridged regimen can be used with females 12-16 years of age who have not yet achieved peak bone density, but who, due to various conditions such as anorexia, are at risk of loss of bone density or at risk of not achieving a normal physiologic bone density for age and developmental maturity.

Thus, the bridged regimen, or the bridged extended cycle regimen, can also be used as a method of treating a condition resulting from menopausal or peri-menopausal estrogen decline, including osteoporosis. The bridged regimen, or the bridged extended cycle regimen, can also be used as a method of providing contraception and treating a condition in a peri-menopausal female in need thereof resulting from peri-menopausal estrogen decline, including osteoporosis.

The bridged regimen, or the bridged extended cycle regimen, can also be used as a method of treating a female in need of hormone replacement therapy.

In some aspects of the invention, the estrogen and progestin of the bridged regimen can be ethinyl estradiol and levonorgestrel, although other useful estrogens and progestins can be employed. The weight ratio of these two active ingredients can be about 1:0.2 to about 1:300. In some aspects of the invention, the weight ratio of estrogen and progestin is about 1:1 to about 1:50. In other aspects of the invention, the weight ratio of estrogen and progestin is about 1:1 to about 1:10. For example, the daily amount of ethinyl estradiol is about 10 μg to about 30 μg and the daily amount of levonorgestrel is about 0.05 mg to about 0.2 mg.

The values given above are for ethinyl estradiol and levonorgestrel, and if a different estrogen or progestin is employed, an adjustment in the amount based on the relative potency or activity can be made. Correlations in potency among the various estrogens and among the various progestins are known. See, for example, EP 0 253 607, which is hereby incorporated in its entirety by reference. For example, 30 μg of ethinyl estradiol is roughly equivalent to 60 μg of mestranol or 2,000 μg of 17β-estradiol. Similarly, 0.050 mg of levonorgestrel is equivalent to about 0.175 mg of norethindrone acetate, about 0.050 mg of desogestrel, about 0.050 mg 3-ketodesogestrel, about 0.035 mg of gestodene, or about 0.100 mg of norgestrel. It should be understood that when norgestrel is used in place of levonorgestrel, its concentration is twice that of levonorgestrel. Norgestrel (dl-norgestrel) is a racemic mixture of optically active isomers, while levonorgestrel is one of the optically active isomers present in norgestrel.

Equivalent concentrations of estrogens and of progestins can be determined using either in vitro or in vivo assay methods. See, for example, Kuhl, H., *Drugs* 51(2): 188-215 (1996); Philibert, D., et al., *Gynecol. Endocrinol.* 13: 316-326 (1999); and Lundeen, S., et al., *J. Steroid Biochem. Molec. Biol.* 78: 137-143 (2001), in which the relative potencies of various progestins are compared using both in vitro and in vivo test assays. See also, for example, Dickey, R. P., "Contraceptive Therapy," *OBG Management Supplement* (October 2000), pp. 2-6. Each of these documents is hereby incorporated by reference in its entirety.

For example, various combinations of progestin and estrogen that have been used in oral contraceptives are shown in Table 1.

TABLE 1

Combinations of Progestin and Estrogen

| Progestin | Dose (mg) | Norethindrone Equivalent Dose (mg) | Estrogen | Dose (mg) | EE Equivalent Dose (mg) | P/E Ratio |
|---|---|---|---|---|---|---|
| Norethynodrel | 9.85 | 9.85 | Mestranol | 0.150 | 0.105 | 93.810 |
|  | 5.00 | 5.00 |  | 0.075 | 0.053 | 95.238 |
|  | 2.50 | 2.50 |  | 0.036 | 0.025 | 99.206 |
|  | 2.50 | 2.50 |  | 0.100 | 0.070 | 35.714 |
| Norethindrone | 10.00 | 10.00 | Mestranol | 0.060 | 0.042 | 238.095 |
|  | 2.00 | 2.00 |  | 0.100 | 0.070 | 28.571 |
|  | 1.00 | 1.00 |  | 0.050 | 0.035 | 28.571 |
|  | 1.00 | 1.00 |  | 0.080 | 0.056 | 17.857 |
| Norethindrone | 1.00 | 1.00 | Ethinyl estradiol (EE) | 0.050 | 0.050 | 20.000 |
|  | 1.00 | 1.00 |  | 0.035 | 0.035 | 28.571 |
|  | 0.50 | 0.50 |  | 0.035 | 0.035 | 14.286 |
|  | 0.40 | 0.40 |  | 0.035 | 0.035 | 11.429 |

TABLE 1-continued

Combinations of Progestin and Estrogen

| Progestin | Dose (mg) | Norethindrone Equivalent Dose (mg) | Estrogen | Dose (mg) | EE Equivalent Dose (mg) | P/E Ratio |
|---|---|---|---|---|---|---|
| Norethindrone acetate | 2.50 | 2.50 | EE | 0.050 | 0.050 | 50.000 |
|  | 1.00 | 1.00 |  | 0.050 | 0.050 | 20.000 |
|  | 0.60 | 0.60 |  | 0.030 | 0.030 | 20.000 |
|  | 1.50 | 1.50 |  | 0.030 | 0.030 | 50.000 |
|  | 1.00 | 1.00 |  | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
|  | 1.00 | 1.00 |  | 0.035 | 0.035 | 28.571 |
| dl-Norgestrel | 0.50 | 0.75 | EE | 0.050 | 0.050 | 10.000 |
|  | 0.30 | 0.45 |  | 0.030 | 0.030 | 10.000 |
| Levonorgestrel | 0.10 | 0.35 | EE | 0.020 | 0.020 | 5.000 |
|  | 0.15 | 0.52 |  | 0.030 | 0.030 | 5.000 |

Equivalencies
50 mg Mestranol = approx. 35 mg Ethinyl estradiol (EE)
0.1 mg dl-Norgestrel = approx. 0.15 mg Norethindrone Each block in Table 1 describes a specific combination of progestin and estrogen, e.g., norethynodrel and mestranol, and within each block older combinations are listed first, with successively newer combinations following.

Suitable progestins for use in the present invention include, but are not limited to, natural and synthetic compounds having progestational activity, such as, for example, progesterone, chlormadinone acetate, norethindrone, cyproterone acetate, norethindrone acetate, desogestrel, levonorgestrel, drospirenone, trimegestone, norgestrel, norgestimate, norelgestromin, etonogestrel, gestodene, and other natural and/or synthetic gestagens. Prodrugs of suitable progestins can also be used in the bridged regimen or bridged extended cycle regimen of the present invention.

The expression "prodrug" denotes a derivative of a known direct acting drug, which derivative has enhanced delivery characteristics and therapeutic value as compared to the drug and is transformed into the active drug by an enzymatic or chemical process. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

Suitable estrogens in the present invention include, but are not limited to, natural and synthetic compounds having estrogenic activity, such as, for example, estradiol (17β-estradiol), 17α-estradiol, estriol, estrone, and their esters, such as the acetate, sulfate, valerate or benzoate esters of these compounds, including, for example, estradiol 17β-cypionate, estradiol 17-propionate, estradiol 3-benzoate, and piperazine estrone sulfate; ethinyl estradiol; conjugated estrogens (natural and synthetic); mestranol; agonistic anti-estrogens; and selective estrogen receptor modulators. Prodrugs of suitable estrogens can also be used in the extended cycle regimen of the present invention. Examples of estrogen prodrugs that can be used in the present invention include, but are not limited to, estradiol acetate (which is converted in vivo to 17β-estradiol) and mestranol (which is converted in vivo to ethinyl estradiol).

The antidepressant that is optionally combined with the bridged regimen can be a selective serotonin reuptake inhibitor (SSRI), a tricyclic antidepressant or anxiolytic, or any antidepressant known to one of skill in the art. Suitable antidepressants include, but are not limited to, alprazolam (XANAX®), clomipramine (ANAFRANIL®), fluoxetine (PROZAC®), paroxetine (PAXIL®), sertraline (ZOLOFT®), nefazodone (SERZONE®), fenfluramine (PONDIMIN®) and venlafaxine (EFFEXOR®).

The daily amount of antidepressant administered can vary, depending on the antidepressant used, from about 0.75 to about 2 mg, from about 10 to about 20 mg, or from about 50 to about 100 mg. For example, in some aspects of the invention, fluoxetine hydrochloride is administered in a daily amount of about 5 mg to about 120 mg.

In some aspects of the invention, the antidepressant is administered during the unopposed estrogen interval of the bridged regimen. In other aspects of the invention, the antidepressant is administered continuously throughout the regimen, intermittently, one time during each menstrual cycle, or once weekly. For example, in some aspects of the invention, fluoxetine hydrochloride is administered in a one-time or once-weekly dose of about 90 mg.

The estrogen and progestin are administered in the conventional manner by any route where they are active. For example, administration can be by, but is not limited to, parenteral, subcutaneous, intravenous, intramuscular, intraperitoneal, transdermal, buccal, or ocular routes, or intravaginally, by inhalation, by depot injections, or by hormone implants. Thus, modes of administration for the estrogen and progestin (either alone or in combination with other pharmaceuticals) can be, but are not limited to, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

Most estrogens and progestins are orally active and this route of administration can be used in the invention. Accordingly, administration forms can include, but are not limited to, tablets, dragees, capsules and pills, which contain the estrogen and the progestin and one or more suitable pharmaceutically acceptable carriers.

For oral administration, the estrogen and progestin can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the estrogen and progestin compositions can take the form of tablets or lozenges formulated in conventional manner.

For administration by inhalation, the estrogen and progestin for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The estrogen and progestin can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions of the estrogen and progestin also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

In the transdermal administration, the estrogen and progestin components, for example, can be applied to a plaster, or can be applied by transdermal, therapeutic systems that are consequently supplied to the organism.

The combination of estrogen and progestin can also be administered in combination with other active ingredients. For example, as described above, estrogen and progestin can be administered in combination with an antidepressant. Estrogen and progestin can also be administered with vitamin D and/or calcium in the bridged regimen as a method of maintaining or preventing loss of bone density. Alternatively, vitamin D and/or calcium can be administered in the bridged regimen during the unopposed estrogen interval following administration of estrogen and progestin. The form of vitamin D and of calcium used in the present invention would be well known to those of skill in the art, as would the amount. For example, calcium can be administered in the form of calcium carbonate, at a daily dosage level of 500 mg.

Thus, pharmaceutical formulations containing the estrogen and progestin and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of estrogen and progestin as taught in this invention. It is known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; and "Goodman & Gilman's The Pharmaceutical Basis of Therapeutics," $6^{th}$ Edition, MacMillan Publishing Co., New York 1980 can be consulted.

The preparations of the invention can be produced in the form of a kit or package, with the daily dosages arranged for proper sequential administration. For example, in some aspects of the invention, e.g., in the oral form of the formulation, the present invention provides a pharmaceutical package which contains combination-type contraceptives in multiple dosage units in a synchronized, fixed sequence, wherein the sequence or arrangement of the dosage units corresponds to the stages of daily administration.

Thus, for example, the pharmaceutical formulations useful in the invention can be provided in kit form containing at least about 20 tablets intended for ingestion on successive days, followed by about 2 to about 10 tablets, intended for ingestion on successive days. Administration is daily for at least 20 consecutive days using tablets containing the both the estrogen and the progestin, and is followed by administration that is daily for about 2 to about 10 consecutive days using tablets containing estrogen. For example, administration can be for 60-110 consecutive days, using tablets containing both estrogen and the progestin, followed by administration for at least 2-10 days with estrogen, using tablets containing estrogen. As another example, administration can be for 81-110 days, using tablets containing both estrogen and progestin, followed by administration for at least 2-10 days with estrogen, using tablets containing estrogen. As yet another example, administration can be for 21-26 days, using tablets containing both estrogen and progestin, followed by administration for at least 2-10 days with estrogen, using tablets containing estrogen.

In another example, the pharmaceutical formulations may be provided in kit form containing, for a 28-day regimen, 25 tablets, each tablet containing estrogen and progestin, intended for ingestion on successive days, followed by 3 tablets, each tablet containing estrogen, intended for ingestion on successive days. In other aspects of the invention, the pharmaceutical formulations may be provided in kit form containing 25 tablets, each tablet containing both the estrogen and the progestin, intended for ingestion on successive days, and 3 tablets, each tablet containing both estrogen and an antidepressant, e.g., fluoxetine hydrochloride, intended for ingestion on successive days.

All of the various aspects, embodiments and options described herein can be combined in any and all variations. The bridged regimen disclosed herein, including the bridged extended cycle regimen, can be administered to females of child-bearing age, peri-menopausal females, or menopausal females as needed for treatment of any of the conditions and disorders described above.

The following examples are illustrative, but not limiting, of the method and compositions of the present invention. Other suitable modifications and adaptations of the variety of conditions and parameters normally encountered and obvious to those skilled in the art are within the spirit and scope of the invention. Thus, the breadth and scope of the present invention should not be limited by any of the above-described exemplary embodiments, but should be defined only in accordance with the following claims and their equivalents.

Example 1

A group of women, each woman having one of the conditions described above, are administered a combined dosage form of estrogen and progestin monophasically for 21 to 26 consecutive days, followed by administration of low-dose estrogen for 2 to 10 days, in which the daily amounts of estrogen and progestin are equivalent to about 5 µg to about 50 µg of ethinyl estradiol and about 0.05 mg to about 1.5 mg of levonorgestrel, respectively.

For example, a group of women, each woman having one of the conditions described above, are administered monophasically a combination of estrogen and progestin for 25 days, followed by administration of estrogen for 3 days. Each woman is administered 25 oral contraceptive tablets on days 1 through 25 of the menstrual cycle, one tablet per day, each tablet containing 150 µg levonorgestrel and 30 µg ethinyl estradiol. On days 26 through 28 of the cycle, each woman is administered 3 tablets, one tablet per day, each tablet containing 30 µg ethinyl estradiol. The administration schedule is illustrated in Table 1. This 28-day regimen is repeated for each menstrual cycle and administered to the women for a period of about one year. Because there are about 13 menstrual cycles per year, there are about 13 treatments administered per year.

TABLE 1

Administration schedule for a 28-day regimen

| Days | Hormone | Antidepressant |
|---|---|---|
| 1-25 | 150 µg levonorgestrel and 30 µg ethinyl estradiol | none |
| 26-28 | 30 µg ethinyl estradiol | none |

The women are monitored for improvement at the conclusion of administration of the regimen.

Example 2

A group of women, each woman having one of the conditions discussed above, are administered a combined dosage form of estrogen and progestin, preferably monophasically, for 21 to 26 consecutive days, followed by administration of estrogen for 2 to 10 days, in combination with the antidepressant fluoxetine hydrochloride, in which the daily amounts of estrogen and progestin are equivalent to about 5 µg to about 50 µg of ethinyl estradiol and about 0.05 mg to about 1.5 mg of levonorgestrel, and the fluoxetine hydrochloride is in an amount of about 5 mg to about 120 mg. Oral contraceptives with initial doses of fluoxetine at either 5 mg or 10 mg/day can be started to avoid any activating side effects that may lead to noncompliance. The dose can then be increased as needed. Fluoxetine can also be given intermittently during the late luteal phase, which is typically 1-2 weeks before menses. In addition, a one-time or once-weekly dose of about 90 mg of fluoxetine can be administered.

For example, a group of women, each woman having one of the conditions described above, are administered monophasically a combination of estrogen and progestin for 25 days, followed by administration of estrogen and an antidepressant for 3 days. Each woman is administered 25 oral contraceptive tablets on days 1 through 25 of the menstrual cycle, one tablet per day, each tablet containing 150 µg levonorgestrel and 30 µg ethinyl estradiol. On days 26 through 28 of the cycle, each woman is administered 3 tablets, one tablet per day, each tablet containing 30 µg ethinyl estradiol and 20 mg fluoxetine hydrochloride and 30 µg ethinyl estradiol. This administration schedule is illustrated in Table 3. This 28-day regimen is repeated for each menstrual cycle and administered to the women for a period of about one year. Because there are about 13 menstrual cycles per year, there are about 13 treatments administered per year.

TABLE 3

Administration schedule for a 28-day regimen with an antidepressant

| Days | Hormone | Antidepressant |
|---|---|---|
| 1-25 | 150 µg levonorgestrel and 30 µg ethinyl estradiol | none |

TABLE 3-continued

Administration schedule for a 28-day regimen with an antidepressant

| Days | Hormone | Antidepressant |
|---|---|---|
| 26-28 | 30 μg ethinyl estradiol | 20 mg fluoxetine hydrochloride daily OR a one-time dose of 90 mg fluoxetine hydrochloride OR a once-weekly dose of 90 mg fluoxetine hydrochloride |

The women are monitored for improvement at the conclusion of administration of the regimen.

Example 3

Another aspect of the invention encompasses a bridged extended cycle regimen that allows a woman the option of limiting her menstrual periods to about four times per year. A group of women, each woman having one of the conditions discussed above, are administered a combined dosage form of estrogen and progestin monophasically for about 81 to 89 days, followed by administration of estrogen for 2 to 10 days, in which the daily amounts of estrogen and progestin are equivalent to about 5-50 μg of ethinyl estradiol and about 0.025 to 10 mg, preferably about 0.05 to 1.5 mg, of levonorgestrel, respectively.

For example, a group of women, each woman having one of the conditions described above, are administered 84 oral contraceptive tablets on days 1 through 84 of the menstrual cycle, one tablet per day, each tablet containing 150 μg levonorgestrel and 30 μg ethinyl estradiol. On days 85-91 of the cycle, each woman is administered 7 tablets, one tablet per day, each tablet containing 30 μg ethinyl estradiol. This administration schedule is illustrated in Table 4. This 91-day regimen is repeated for a total period of about one year, with four treatments administered per year.

TABLE 4

Administration schedule for a 91-day regimen

| Days | Hormone | Antidepressant |
|---|---|---|
| 1-84 | 150 μg levonorgestrel and 30 μg ethinyl estradiol | none |
| 85-91 | 30 μg ethinyl estradiol | none |

The women are monitored for improvement at the conclusion of administration of the regimen.

Example 4

A group of women, each woman having one of the conditions discussed above, are administered a combined dosage form of estrogen and progestin monophasically for about 81 to 89 days, followed by administration of low-dose estrogen and fluoxetine hydrochloride for 2 to 10 days, in which the daily amounts of estrogen and progestin are equivalent to about 5-50 μg of ethinyl estradiol and about 0.025 to 10 mg, preferably about 0.05 to 1.5 mg, of levonorgestrel, respectively, and the fluoxetine hydrochloride is in an amount of about 5-120 mg. Oral contraceptives with initial doses of fluoxetine at either 5 mg or 10 mg/day can be started to avoid any activating side effects that may lead to noncompliance. The dose can then be increased as needed. Fluoxetine can also be given intermittently during the late luteal phase, which is typically 1-2 weeks before menses. In addition, a one-time or once-weekly dose of about 90 mg of fluoxetine can be administered.

For example, a group of women, each woman having one of the conditions described above, are administered 84 oral contraceptive tablets on days 1 through 84 of the menstrual cycle, one tablet per day, each tablet containing 150 μg levonorgestrel and 30 μg ethinyl estradiol. On days 85-91 of the cycle, each woman is administered 7 tablets, one tablet per day, each tablet containing 30 μg ethinyl estradiol and 20 mg fluoxetine hydrochloride. This administration schedule is illustrated in Table 5. This 91-day regimen is repeated for a total period of about one year, with four treatments administered per year.

TABLE 5

Administration schedule for a 91-day regimen with an antidepressant

| Days | Hormone | Antidepressant |
|---|---|---|
| 1-84 | 150 μg levonorgestrel and 30 μg ethinyl estradiol | none |
| 85-91 | 30 μg ethinyl estradiol | 20 mg fluoxetine hydrochloride daily OR a one-time dose of 90 mg fluoxetine hydrochloride OR a once-weekly dose of 90 mg fluoxetine hydrochloride |

The women are monitored for improvement at the conclusion of administration of the regimen.

Example 5

Multicenter Randomized Phase III Clinical Trial to Evaluate Two Continuous Oral Contraceptive Regimens in Women Diagnosed with Premenstrual Syndrome (PMS) and Premenstrual Dysphoric Disorder (PMDD)

Clinical Design and Summary

In a multicenter, randomized, clinical trial the efficacy and safety of three combination oral contraceptives regimens in the prevention of pregnancy in sexually active women, ages 18 through 40 years, will be evaluated. Patients will be randomized in a 1:1:1 fashion to one of the following regimens:

Levonorgestrel 150 μg/ethinyl estradiol (EE) 30 μg administered once daily for 84 days as a combination oral tablet followed by ethinyl estradiol 30 μg administered once daily for 7 days (DP3-84/30);

Levonorgestrel 150 μg/ethinyl estradiol 30 μg administered once daily for 84 days as a combination oral tablet followed by ethinyl estradiol 10 μg administered once daily for 7 days (DP3-84/10); or Levonorgestrel 150 μg/ethinyl estradiol 30 μg administered once daily for 25 days as a combination oral tablet followed by ethinyl estradiol 30 μg administered once daily for 3 days (DP3-25/30).

Patients randomized to either DP3-84/30 or DP3-84/10 will receive 4 cycles of study drug. Patients randomized to DP3-25/30 will receive 13 cycles of study drug. All patients will receive approximately 1 year of therapy.

The study coordinator or designated personnel will register the patient. Patients will be randomly assigned to one of the treatment regimens. The treatment group assignment will not be revealed to the patient prior to signing of the informed consent.

All patients, regardless of randomization, will initiate study OC therapy on the first Sunday following the beginning of their menstrual period ("Sunday starters") and will remain as Sunday starters throughout the study. Each of the dose packs will be dispensed with an abbreviated patient information sheet and a more detailed patient package insert (PPI).

All patients will complete and download information entered into an electronic diary. Assessments will include study drug compliance, use of additional forms of contraception, bleeding patterns, weight, assessment of the incidence and severity of menstrual related symptoms and medication taken to relieve these symptoms. Information will be self-recorded on the electronic diary via a series of pre-programmed questions.

Two hundred (200) patients in each treatment arm are targeted to complete the study. Pregnancy rate will be calculated using data from those patients age 18 to 35. Patients age 36 through 40 will also be enrolled.

Patient Eligibility

Inclusion Criteria

Patients must meet the following criteria to be included in the study:

1. Sexually active adult females (age 18 through 40), of child bearing potential, in a heterosexual relationship, at risk for pregnancy, who are in good health and who have a history of OC use for an interval of at least three successive cycles with regular withdrawal bleeding (bleeding during the pill-free interval or during the first three days of the subsequent cycle) prior to enrollment (Continuous Users)

OR have no prior history OC use (Fresh-Starts)

OR have no history of OC use in the 6 months prior to enrollment (Prior Users)

2. Negative urine pregnancy test.
3. Signed informed consent.
4. Agree to use study oral contraceptive therapy as their primary birth control method (BCM).

Exclusion Criteria:

Patients will be excluded from the study if any of the following criteria are met:

1. History of hypersensitivity to estrogen or progestin components of OCs.
2. History of alcohol or drug abuse which, in the opinion of the investigator, makes the patient unfit for participation in the study.
3. Active smoker age>34 years.
4. Chronic use of any medication that may interfere with the efficacy of oral contraceptives.
5. History of being HIV or Hepatitis C positive.
6. History of persistent noncompliance with any chronic medication.
7. History of having received injectable hormone therapy (e.g., Depo-Provera® (Pharmacia and Upjohn)) within the 10 months prior to enrollment or having a progestin-releasing intrauterine device (IUD) in place within 3 months prior to enrollment or has had a contraceptive implant removed within one month prior to enrollment or has received any other form of hormonal contraception within 3 months prior to enrollment.
8. Routine concomitant use of additional forms of contraception (IUD, diaphragm, contraceptive sponge) with the exception of condoms.
9. Patients who have had recent surgical or medical abortion, miscarriage, or vaginal or cesarean delivery must have had at least two normal menstrual cycles prior to enrollment.
10. History of abnormal bleeding (breakthrough or withdrawal bleeding that lasts $\geq 10$ consecutive days or excessive spotting that lasts $\geq 10$ consecutive days) while on conventional oral contraceptives.
11. History of thromboembolic disorder, vascular disease, cerebral vascular or coronary artery disease.
12. Uncontrolled or untreated hypertension (systolic BP$\geq$140 mmHg and diastolic BP$\geq$90 mmHg on more than two occasions).
13. Known or suspected carcinoma of the breast, endometrial carcinoma or known or suspected estrogen dependent neoplasia.
14. Undiagnosed abnormal genital bleeding.
15. History of hepatic adenomas or carcinomas.
16. History of cholestatic jaundice of pregnancy or jaundice with prior OC use.
17. Known or suspected pregnancy or currently breastfeeding.
18. Hyperlipidemia requiring active treatment with antihyperlipidemic agents.
19. History of diabetes mellitus, glucose intolerance or gestational diabetes.
20. History of abnormal laboratory value at screening
21. Any clinically significant abnormal finding or condition on history, screening, physical exam, pelvic exam or any laboratory finding which contraindicates the use of oral contraceptives.
22. Has participated in any clinical investigation within the 30 days prior to enrollment.
23. Has donated or had a loss of more than 500 cc of blood within the 30 days prior to enrollment.

Treatment Regimen

Description of Study Medication

DP3-84/30

All tablets in the DP3-84/30 regimen; 84 tablets each containing 150 µg levonorgestrel/30 µg EE and 7 tablets each containing 30 µg of EE will be white unembossed tablets. One combination tablet will be taken each day for 84 days followed by 7 days of EE tablets in 91-day cycles repeated consecutively for approximately one year (4 cycles). Each DP3-84/30 dose kit will be packaged in a 3-part fold-out white blister card pack where each of the first two blister packs has 28 active tablets each and the third blister pack has 28 active tablets and 7 ethinyl estradiol tablets (35 tablets total) for each 91-day cycle.

Each blister card pack will be sealed into a foil pouch, which will be labeled with a patient-specific label. Each foil pouch will contain an oxygen absorber. At each clinic visit one foil pouch, a patient information sheet, a PPI and a child resistant pouch will be dispensed.

DP3-84/10

All tablets in the DP3-84/10 regimen; 84 tablets each containing 150 µg levonorgestrel/30-µg EE and 7 tablets each containing 10 µg of EE will be white unembossed tablets. One combination tablet will be taken each day for 84 days followed by 7 days of EE tablets in 91-day cycles repeated consecutively for approximately one year (4 cycles). Each DP3-84/10 dose kit will be packaged in a 3-part fold-out white blister card pack where each of the first two blister packs has 28 active tablets each and the third blister pack has 28 active tablets and 7 ethinyl estradiol tablets (35 tablets total) for each 91-day cycle.

Each blister card pack will be sealed into a foil pouch, which will be labeled with a patient-specific label. Each foil pouch will contain an oxygen absorber. At each clinic visit one foil pouch, a patient information sheet, a PPI and a child resistant pouch will be dispensed.

DP3-25/30

All tablets in the DP3-25/30 regimen; 25 tablets each containing 150 μg levonorgestrel/30 μg EE and 3 tablets each containing 30 μg of EE will be white unembossed tablets. One combination tablet will be taken each day for 25 days followed by 3 days of EE tablets in 28-day cycles repeated consecutively for approximately one year (13 cycles). Each DP3-25/30 blister card will have 25 active tablets followed by 3 ethinyl estradiol tablets (28 tablets total) for each 28-day cycle.

Each blister card will be sealed into a foil pouch, which will be labeled with a patient-specific label. Each foil pouch will contain an oxygen absorber. At clinic visits one through three, 3 foil pouches, a patient information sheet, a PPI and a child resistant pouch will be dispensed. At clinic visit four, 4 foil pouches, a patient information sheet, a PPI and a child resistant pouch will be dispensed.

All patients, regardless of randomization, will be instructed to initiate OC therapy on the first Sunday following the beginning of their menstrual period ("Sunday starters"). Patients will be instructed to take their study medication at the same time each day. Day 1 of the study will be defined as the first day of study medication.

Administration

Designated personnel will dispense all study drugs. All study medications must be kept in a secured area at temperature ranging from approximately 15-25° C. (59-77° F.). All patients will be instructed to take one tablet per day at approximately the same time each day. All patients will be "Sunday starters"; that is all patients will begin study drug therapy on the first Sunday following the start of their previous menstrual cycle or completion of prior oral contraceptive regimens. All patients enrolled in the study will maintain Sunday starts for each successive cycle.

The end-of-study evaluation will take place 1 week following completion of withdrawal menses following the last cycle of study OC therapy. At the clinic visit during which patients receive the final supply of study medication, they will be counseled to use an alternative method of birth control during the interval between when they have finished study medication until they have completed the final study visit.

Patients randomized to DP3-84/30 or DP3-84/10 will receive a 13-week supply (single cycle) of study drug at each clinic visit during Weeks 13, 26 and 39. Patients randomized to DP3-25/30 will receive a 12-week supply (three-cycles) of study drug at the initiation of the study and at clinic visits during Weeks 12 and 24. During the clinic visit at Week 36 patients randomized to DP3-25/30 will receive 16-week supply (four cycles) of study medication.

Examinations/Tests

TABLE 5

Study Schedule

| Parameter | Screening | Visit 1 | Visits 2-4[a] | Completion of Therapy |
|---|---|---|---|---|
| Informed consent | X | | | |
| Medical and contraceptive history | X | | | |
| Physical exam including pelvic exam | X | | | X |
| Weight, vital signs | X | X | X | X |
| Pap smear | X | | | X |
| Randomization | | X | | |
| Clinical laboratory tests[b] | X | | | X |
| Urine pregnancy test[c] | X | X | X | X |
| Study drug distribution[d] | | X | X | |
| Electronic diary distribution | | X | | |
| Study drug compliance measurement | | | X | X |
| Adverse event recording | | | X | X |

[a]Patients randomized to DP3-84/30 or DP3-84/10 will be seen at Weeks 13, 26 and 39. Patients randomized to DP3-25/30 will be seen at Weeks 12, 24, and 40.
[b]Clinical laboratory tests include CBC, serum chemistry, lipid profile, urinalysis
[c]Repeated on Visit 1 if the screening was completed more than 2 weeks prior to enrollment
[d]For patients randomized to DP3 25/30, three (3) cycle supply will be dispensed at Weeks 12 and 24; a four (4) cycle supply will be dispensed at Week 40.

Study Procedures by Visit

Screening and Enrollment

Patients will sign informed consent. Prior to enrollment, within four weeks prior to initiation of study therapy, all patients will undergo a screening evaluation that will include prior medical and contraceptive history, smoking history, physical examination including pelvic exam and Pap smear, vital signs and weight, and clinical laboratory tests including complete blood count (CBC), serum chemistry, lipid profile, urinalysis, and urine pregnancy test.

All clinical laboratory evaluations (blood and urine) will be tested by a central laboratory. All investigators will be provided with a laboratory manual that outlines sampling and shipping procedures.

If the screening evaluation is completed more than two weeks prior to the initiation of study therapy, the urine pregnancy test must be repeated at Visit 1. Patients with a report of an abnormality on Pap smear will be disqualified for enrollment unless investigator decides the results are not clinically significant and will not interfere with conduct of the study. Investigator's decision must be documented. Patients who have had a normal Pap smear within the three months prior to enrollment in the study will not be required to have the test repeated. A copy of the results must be available in the patient's medical record. Any patient with a report of insufficient cells must have the test repeated and documented as normal prior to enrollment. Patients will then be enrolled in the study.

Visit 1

Visit 1 will take place during the final week of the menstrual cycle prior to beginning study therapy (i.e., during menses for those patients not taking oral contraceptives or during Week 4 for those patients taking oral contraceptives). During Visit 1 patients will be randomized to one of the following treatment groups:

DP3-84/30; levonorgestrel 150 μg/EE 30 μg for 84 days+ EE 30 μg for 7 days

OR

DP3-84/10; levonorgestrel 150 μg/EE 30 μg for 84 days+ EE 10 μg for 7 days

OR

DP3-25/3; levonorgestrel 150 μg/EE 30 μg for 25 days+EE 30 μg for 3 days

The treatment regimen assignment will be ascertained by randomization via Interactive Voice Response System (IVRS). The treatment group assignment will not be revealed to the patient prior to signing of the informed consent.

A urine pregnancy test will be re-administered to those women who were screened more than two weeks prior to Visit 1. Study medication will be dispensed with patient instructions. An electronic diary will be given to each patient. Each patient will be trained regarding the use and care of the electronic diary. Patients will be instructed to take each dose of study medication and to complete all diary entries at approximately the same time each day.

Visits 2-4

All visits should take place within seven days prior to completion of study medication for that cycle. Any visit that takes place prior to the final week of the cycle will be recorded as a protocol deviation. Any visit that takes place following the final week of the cycle resulting in a lapse in study medication intake will be recorded as a protocol violation and will result in the patient being withdrawn from the study. Any visit that takes place following the final week of the cycle but does not result in a lapse in study medication (e.g., the patient received an emergency supply of study medication) will be recorded as a protocol deviation.

Patients randomized to either DP3-84/30 or DP3-84/10 will be seen at Weeks 13, 26 and 39. Patients randomized to DP3-25/30 will be seen at Weeks 12, 24 and 36. During these visits, patients will be queried regarding adverse events, concomitant medications, change in smoking history, and compliance. Vital signs and weight will be recorded. A urine pregnancy test will be conducted. Used study medication will be returned and counted by the study pharmacist or designated personnel.

Completion of Therapy

The end-of-study evaluation will take place 1 week following completion of last cycle of the study drug. Patients will be counseled to use birth control during the interval between when they have finished study medication until they have completed the final study visit. Patients will undergo physical exam, including pelvic exam and pap smear. Vital signs and weight will be recorded. Blood and urine samples for clinical laboratory tests including CBC, serum chemistry, lipid profile, urinalysis and urine pregnancy test will be obtained. Used study medication cards will be returned and counted by the study pharmacist or designated personnel. Patients will be queried regarding adverse events, concomitant medications, change in smoking history and compliance. The electronic diary will be returned.

Post-Study Visit

After study completion/withdrawal, patients will be followed via a phone call for occurrence of pregnancy and until the menstrual cycle returns to normal. The patient based on the cycle pattern prior to the study entry will determine return to normal menstrual cycle. The minimum period of follow up will be 3 months. Patients who decide to use a contraceptive method that regulates/alters menstrual cycle after study completion/withdrawal will be followed for 3 months via a phone call.

Only those patients who have an on-going serious adverse event that has not resolved or those who become pregnant during the course of the study will be followed via clinic visits after completion of the study. Patients with on-going serious adverse events will be followed until the event has been satisfactory managed or resolved. Patients who are pregnant will be followed for eight weeks following delivery or termination of the pregnancy. Infants' health assessment will be followed for eight weeks following delivery. This follow-up may be in the form of a written report from a family physician, obstetrician or pediatrician. All serious adverse events that occur in the three months following discontinuation of therapy will be reported. SAEs that occur at any time after study completion/discontinuation will be reported if investigator determines it is drug-related.

Early Termination

Any patient who withdraws or is withdrawn from the study must return the investigational medication and electronic diary and will be required to complete all procedures for the final visit. All patients will be followed via a phone call for 3 months for the occurrence of pregnancy and until the menstrual cycle return to normal. All patients will be followed via a phone call for three months for the occurrence of serious adverse events.

Examinations and Procedures

Physical Exam, Medical and Gynecologic History

A complete physical and gynecologic exam, including PAP smear, will be performed at screening and at the completion of therapy or upon early withdrawal from the study. Any patient with an abnormal Pap smear will be disqualified for enrollment unless investigator decides the results are not clinically significant and will not interfere with conduct of the study. The Investigator's decision must be documented. Patients who have had a Pap smear reported as within normal limits within the three months prior to enrollment in the study will not be required to have the test repeated. A copy of the results must be available in the patient's medical record. Any patient with a report of insufficient cells must have the test repeated and documented by the investigator as within normal limits prior to enrollment.

Laboratory Safety Tests

Clinical laboratory tests will be performed at screening and at the completion of therapy or upon early withdrawal. All clinical laboratory tests will be done at one central laboratory. Laboratory tests will include CBC, serum chemistry, lipid profile, urinalysis, and urine pregnancy test. In addition, urine pregnancy tests will be conducted at every clinic visit and at the completion of therapy or upon early withdrawal from the study. All urine pregnancy tests will be performed using the Sure Step® Pregnancy Test kit (Applied Biotech, Inc.).

Pregnancy

All patients will be followed for the occurrence of pregnancy for three months following completion of the study. This follow-up may be in the form of a telephone call. All pregnancies that occur during the course of the study or in the three months following completion of the study will be dated using ultrasound to establish the gestational age of the fetus. Patients who become pregnant during the course of the study due to method failure will be followed for eight weeks following delivery or termination of the pregnancy. Infants' health assessment will be followed for eight weeks following delivery. This follow-up may in the form of a documented telephone conversation with associated pediatrician or written report from the associated pediatrician.

Electronic Diaries

Patients will be asked to complete electronic diaries. The diary will be programmed to ask specific questions related to the study compliance, bleeding pattern and occurrence of symptoms that are commonly associated with the hormone fluctuation during the menstrual cycle. The questions will address dosage, compliance, bleeding pattern and hormone-related symptoms either on the scale from 0-3 or using 10 cm Visual Analogue Scale (VAS).

Hand-held data acquisition devices will be used to collect patient responses. The electronic diary will provide patients with a menu-driven, graphical interface to enter diary information (as well as objective data) using a hand-held stylus. Data entry will be electronic and key fields must be completed properly before allowing patient to finish the report. Each report will be downloaded by dial-up network connection.

The electronic diary will incorporate an alarm to remind the patient when to complete their reports. Alarm times will be set by the site and can be specific to the patient preference. The patient will be instructed to complete a diary on a daily basis. Retrospective data entry will not be allowed; reports cannot be completed for previous days. Once each question is completed the patient will confirm the response and will not be permitted to return to that question for modification.

Information on the hormone-related symptoms to be collected is from the Calendar of Premenstrual Experiences (COPE) and Diagnostic and Statistical Manual of Mental Disorders Forth Edition (DSM-IV).

The validity and reliability of the COPE instrument was assessed by Mortola, et al., Obstet. Gynecol. 89: 179-83 (1990), who administered it throughout two consecutive ovulatory cycles to 36 rigidly screened women with PMS and to 18 controls. The validity of the visual analogue scales applied to the psychological symptoms associated with the PMDD has been previously documented.

Treatment Modifications Based on Toxicity

No significant toxicity is expected from the study medication. However, if the patient develops any symptoms or any abnormal laboratory parameter attributed to the drug, which are considered by the patient and/or physician to be of unacceptable severity, then the study medication should be discontinued.

Concomitant Medications

Patients will be queried regarding concomitant medication use at monthly phone calls and quarterly clinic visits. All concomitant medication use (both prescription and over-the-counter (OTC), including herbal medications and nutritional supplements) must be reported during the study, and recorded on the patient's Case Report Form (CRF).

Patients who require the initiation of chronic therapy with drugs that are known to interact with OCs will be withdrawn from the study. Patients who require intermittent therapy with drugs known to interact with OCs (e.g. antibiotic therapy) will remain in the study and will receive counseling regarding the need for additional contraceptive protection during the entire cycle. Patients will be provided with the list of medications that are know to interact with OC and will be instructed to notify study coordinator as soon as medication is prescribed to receive proper counseling. Notification and counseling can be conducted via the phone and must be documented in the patient's CRF. Those cycles in which drugs known to interact with OC therapy are taken will not be used in the calculation of the pregnancy rate.

The use of emergency contraceptive pills ("morning after pills") is prohibited in the study. Data from any patient who utilizes contraceptive pills others than those provided for the study will not be included in the calculation of the pregnancy rate for that cycle.

Adverse Event Reporting

An Adverse Event (AE) is any reaction, side effect, or other undesirable event that occurs in conjunction with the use of a drug, biological product or diagnostic agent in humans, whether or not the event is considered drug related.

A serious adverse event (SAE) is one that meets any one of the following criteria:
 Fatal or life threatening
 Requires or prolongs inpatient hospitalization
 Results in persistent or significant disability/incapacity
 Congenital anomaly The term "life threatening" in the definition of "serious" refers to an event in which the patient was at risk of death at the time of the event; it does not refer to an event that hypothetically might have caused death if it were more severe. Medical and scientific judgment should be exercised in deciding whether an important medical event is serious. Although the event may not be immediately life threatening, fatal, or result in hospitalization, it should be considered serious when it jeopardizes the patient, or requires an intervention to prevent a serious outcome as defined above.

The AE reporting period for this study begins at the Enrollment Visit and ends at the final clinic visit. The SAE reporting period will continue for 3 month after the final clinic visit. All SAEs will be followed through resolution or until investigator assesses the SAE as chronic or stable.

A preexisting condition (i.e., a disorder present before the AE reporting period started and noted on the pretreatment medical history/physical form) should not be reported as an AE unless the condition worsens or episodes increase in frequency during the AE reporting period.

During the study AEs will be recorded through monthly phone calls and quarterly clinic visits. A call-in number will be provided to the patients who wish to report an adverse event between the scheduled phone calls and clinic visits.

Example 6

Multicenter Randomized Phase III Clinical Trial to Evaluate Two Continuous Oral Contraceptive Regimens in Combination with Fluoxetine Hydrochloride in Women Diagnosed with Premenstrual Syndrome (PMS) and Premenstrual Dysphoric Disorder (PMDD)

Overview of the Study Design

In a three-arm, parallel, randomized, multicenter, placebo-controlled, double-blinded study, the efficacy and safety of continuous oral contraceptive therapy as a ninety-one day regimen (84 days active combination therapy followed by low dose estrogen for 7 consecutive days (DP3-91)), or as a twenty-eight day regimen (21 day active combination therapy followed by low dose estrogen for 7 consecutive days (DP3-28)), in combination with fluoxetine hydrochloride administered for approximately 6 consecutive months to women diagnosed with PMS and/or PMDD who desire contraception, will be evaluated.

A cohort of approximate 40-100 patients enrolled in each of the study arms will undergo endometrial biopsy (to test incidence of hyperplasia and carcinoma) prior to the initiation of study drug therapy and at the conclusion of the study or withdrawal.

Efficacy of the 28-day and 91-day regimens on premenstrual symptomotology will be measured by psychometric scales that include self-administered Visual Analogue Scales (VAS) and a prospective daily symptoms chart to evaluate psychological and somatic symptoms. The VAS measures tension, irritability, dysphoria, sleeping and eating patterns, headache, bloating, pain and breast tenderness and weight gain symptoms. Total score of the psychological and somatic symptoms will be computed. The patient and blind observer will also complete the PMTS at each visit.

Study Population

Females ages 18 through 49 who are fluent in English and capable of giving informed consent, without contraindication to the use of oral contraceptives and selective serotonin reuptake inhibitors (SSRIs), and meet the criteria for PMS including PMDD as defined in the diagnostic and statistical manual of mental disorders (DSM-IV). All patients will be counseled at the beginning of the study and at each study visit to use an alternative form of contraception. All patients will be followed for the occurrence of pregnancy during the course of the study. Patients who become pregnant during the course of the study will be followed for eight weeks following delivery or termination of the pregnancy. Infants will be followed for eight weeks following delivery.

Dosage

Patients will be randomized to one of the following:
(1) Ninety-one day oral contraceptive therapy with ethinyl estradiol (DP3-91) and fluoxetine hydrochloride administered for two cycles where each cycle consists of: 150 μg levonorgestrel and 30 μg ethinyl estradiol (days 1-84 of the first cycle and days 92-175 of the second cycle, 30 μg ethinyl estradiol (days 85-91 of the first cycle and days 176-182 of the second cycle), 20 mg fluoxetine hydrochloride (days 1-182), and placebo to preserve blinding (days 183-196);
(2) Twenty-eight day oral contraceptive therapy with ethinyl estradiol (DP3-28) administered for 7 cycles where each cycle consists of: 150 μg levonorgestrel and 30 μg ethinyl estradiol (days 1-21 for seven cycles), 30 μg ethinyl estradiol (days 22-28 for seven cycles), and 20 mg fluoxetine hydrochloride (days 1-196); or
(3) Fluoxetine hydrochloride administered daily for 196 days: 20 mg fluoxetine hydrochloride per day (days 1-196) or placebo to preserve blinding (days 1-196).

Study Management

The study will utilize electronic case report forms and remote system management. Each investigator will be provided a programmed laptop computer dedicated to the study. This system allows the investigator to download and view patient diary data during clinic visits and also allows for rapid data queries by the study monitors. The system will also allow real-time on-line tracking of study site accrual rates, serious adverse events, pregnancies and study progress.

Outcomes Measurement Scales

The primary outcome will be defined as reduction in symptoms of PMS including PMDD as measured by the mean scores on Visual Analogue Scales (VAS) and the Premenstrual Tension Syndrome Scale (PMTS). The VAS will measure tension, irritability, dysphoria, sleeping and eating patterns, headache, bloating, pain and breast tenderness symptoms. Patients will be prompted to rate how they feel each day using 100 mm scales in which the descriptors range from "no symptoms" (0 mm) to "severe or extreme symptoms" (100 mm). The PMTS consists of a 36 item scale that will be completed by the patient and a 10-item scale completed by the blinded observer. Both scales rate premenstrual symptoms for a particular day; the total score can range from 0 (no symptoms) to 36 (all symptoms present and severe).

The secondary outcome will be defined as reduction in symptoms of PMS including PMDD as measured by the sub-score of somatic symptoms on VAS. The VAS will measure headache, bloating, pain and breast tenderness and weigh gain symptoms. Patients will be prompted to rate how they feel each day using 100 mm scales in which the descriptors range from "no symptoms" (0 mm) to "severe symptoms" (100 mm). In addition to information recorded in paper diaries, a standardized questionnaire will be used to determine whether the patient had any side effects.

Statistical Analysis

For the primary analysis, the mean of the VAS scales will be derived to obtain a single VAS score, which evaluates composite psychological and symptomatic outcomes. Mean percent reduction from baseline at the luteal phase will be compared using an analysis of covariance (ANCOVA) approach that evaluates the effects of the treatment group, center and treatment-by-center interaction, after adjusting for the effect of the baseline VAS score. All statistical tests will be two-sided at the 0.05 level of significance. Pairwise comparisons will be made for each active treatment to placebo. Secondary analyses will include a set of statistical tests for the PMTS and 10-item blinded observer-based measures.

Example 7

Two multicenter, randomized, Phase III clinical trial studies were conducted following a protocol similar to the protocol presented in Example 5. During both clinical studies, the number of days of bleeding (withdrawal menses and unscheduled bleeding) was monitored.

For the first clinical study, patients were randomized to one of the following oral contraceptive regimens:
  Levonorgestrel 150 μg/ethinyl estradiol (EE) 30 μg administered once daily for 84 days as a combination oral tablet followed by ethinyl estradiol 30 μg administered once daily for 7 days (DP3-84/30);
  Levonorgestrel 150 μg/ethinyl estradiol 30 μg administered once daily for 84 days as a combination oral tablet followed by ethinyl estradiol 10 μg administered once daily for 7 days (DP3-84/10); or
  Levonorgestrel 150 μg/ethinyl estradiol 30 μg administered once daily for 25 days as a combination oral tablet followed by ethinyl estradiol 30 μg administered once daily for 3 days (DP3-25/30).

For the second clinical study, patients were randomized to one of the following oral contraceptive regimens:
  Levonorgestrel 150 μg/ethinyl estradiol (EE) 30 μg administered once daily for 84 days as a combination oral tablet followed by ethinyl estradiol 30 μg administered once daily for 7 days (DP3-84/30);
  Levonorgestrel 150 μg/ethinyl estradiol 30 μg administered once daily for 84 days as a combination oral tablet followed by ethinyl estradiol 10 μg administered once daily for 7 days (DP3-84/10); or
  Levonorgestrel 150 μg/ethinyl estradiol 30 μg administered once daily for 25 days as a combination oral tablet followed by ethinyl estradiol 30 μg administered once daily for 3 days (DP3-25/30); or
  Levonorgestrel 150 μg/ethinyl estradiol (EE) 30 μg administered once daily for 21 days as a combination oral tablet followed by 7 days of placebo (conventional 28-day oral contraceptive regimen ("Nordette")).

Patients randomized to either the DP3-84/30 or DP3-84/10 regimens in both clinical studies received four 91-day cycles of therapy (the designated regimen). Patients randomized to the DP3-25/30 regimen for both clinical studies, or the conventional 28-day regimen in the second clinical study, received thirteen 28-day cycles of therapy. All patients received approximately 1 year of therapy.

Tables 7 and 8 summarize the average number of days of breakthrough bleeding (defined as unscheduled bleeding and/or spotting) per cycle by treatment group, for the first and second clinical studies. The median (per monthly cycle) values in each table represent the median number of days of breakthrough bleeding per 91-day cycle converted to a 28-day cycle (median $$*\frac{21}{84} \text{ or } \frac{21}{25},$$

depending on the number of days of combination therapy) for comparison with "Nordette" (conventional 28-day regimen in the second clinical study). Table 7 also presents data from a third Phase III clinical study (Anderson, F. D., et al., *Contraception* 68: 89-96 (2003)) that was conducted following a protocol similar to the protocol presented in Example 5, but in which the patients were randomized to one of the following four regimens:

Levonorgestrel 150 μg/ethinyl estradiol (EE) 30 μg administered once daily for 21 days as a combination oral tablet followed by 7 days of placebo ("Nordette"); or Levonorgestrel 100 μg/ethinyl estradiol 20 μg administered once daily for 21 days as a combination oral tablet followed by 7 days of placebo; or Levonorgestrel 150 μg/ethinyl estradiol 30 μg administered once daily for 84 days as a combination oral tablet followed by 7 days of placebo ("Seasonale"); or Levonorgestrel 100 μg/ethinyl estradiol (EE) 20 μg administered once daily for 84 days as a combination oral tablet followed by 7 days of placebo.

The Seasonale and Nordette data from this third clinical study are presented in Table 7. All data presented in Table 8 were from the second clinical study.

TABLE 7

Number of Days of Unscheduled Bleeding and/or Spotting Per Cycle, By Treatment Groups - Complete Cycles Only

| Regimen (Treatment Group)* | Cycle | N | Mean | SD | Min | Q1 | Median | Q3 | Max | Median Per Monthly Cycle |
|---|---|---|---|---|---|---|---|---|---|---|
| DP3-84/30 | 1 | 751 | 15.4 | 14.55 | 0 | 4 | 11 | 24 | 74 | 2.8 |
|  | 2 | 609 | 12.5 | 13.38 | 0 | 3 | 7 | 20 | 82 | 1.8 |
|  | 3 | 515 | 10.0 | 11.12 | 0 | 2 | 7 | 14 | 62 | 1.8 |
|  | 4 | 420 | 9.5 | 11.17 | 0 | 2 | 5 | 13 | 68 | 1.3 |
| DP3-84/10 | 1 | 769 | 14.3 | 13.52 | 0 | 3 | 11 | 21 | 73 | 2.8 |
|  | 2 | 625 | 9.5 | 10.51 | 0 | 2 | 5 | 14 | 63 | 1.3 |
|  | 3 | 531 | 7.3 | 9.12 | 0 | 1 | 4 | 10 | 50 | 1.0 |
|  | 4 | 443 | 7.5 | 9.33 | 0 | 1 | 4 | 10 | 58 | 1.0 |
| Seasonale | 1 | 385 | 16.4 | 15.0 | 0 | 3 | 14 | 25 | 84 | 3.5 |
|  | 2 | 331 | 12.3 | 13.0 | 0 | 2 | 7 | 19 | 66 | 1.8 |
|  | 3 | 296 | 10.8 | 12.4 | 0 | 1 | 6 | 15.5 | 62 | 1.5 |
|  | 4 | 262 | 9.1 | 11.0 | 0 | 1 | 4 | 15 | 55 | 1.0 |
| Nordette | 1 | 214 | 2.1 | 3.1 | 0 | 0 | 1 | 3 | 19 |  |
|  | 2 | 210 | 1.9 | 2.2 | 0 | 0 | 1 | 3 | 12 |  |
|  | 3 | 204 | 1.7 | 2.3 | 0 | 0 | 1 | 2 | 12 |  |
|  | 4 | 194 | 1.3 | 1.8 | 0 | 0 | 1 | 2 | 14 |  |
|  | 5 | 188 | 1.6 | 2.0 | 0 | 0 | 1 | 2 | 11 |  |
|  | 6 | 184 | 1.5 | 1.9 | 0 | 0 | 1 | 2 | 14 |  |
|  | 7 | 178 | 1.4 | 1.6 | 0 | 0 | 1 | 2 | 8 |  |
|  | 8 | 177 | 1.6 | 2.0 | 0 | 0 | 1 | 2 | 14 |  |
|  | 9 | 172 | 1.6 | 2.1 | 0 | 0 | 1 | 2 | 16 |  |
|  | 10 | 170 | 1.7 | 2.3 | 0 | 0 | 1 | 3 | 20 |  |
|  | 11 | 163 | 2.0 | 2.6 | 0 | 0 | 1 | 3 | 19 |  |
|  | 12 | 162 | 1.6 | 2.0 | 0 | 0 | 1 | 3 | 11 |  |
|  | 13 | 159 | 1.6 | 2.1 | 0 | 0 | 1 | 2 | 13 |  |

*Data for the treatment groups DP3-84/30 and DP3-84/10 are from the first clinical study. Data from a third clinical study in which the corresponding non-estrogen-bridged extendedcycle regimen ("Seasonale") and a non-estrogen-bridged conventional 28-day regimen ("Nordette") were administered are included for comparison.

TABLE 8

Number of Days of Unscheduled Bleeding and/or Spotting Per Cycle, By Treatment Groups - Complete Cycles Only (Second Clinical Study)

| Regimen (Treatment Group)* | Cycle | N | Mean | SD | Min | Q1 | Median | Q3 | Max | Median Per Monthly Cycle |
|---|---|---|---|---|---|---|---|---|---|---|
| DP3-84/30 | 1 | 70 | 18.7 | 17.17 | 0 | 6 | 14.5 | 27 | 76 | 3.6 |
|  | 2 | 54 | 10.4 | 8.36 | 0 | 4 | 8.5 | 16 | 38 | 2.1 |
|  | 3 | 45 | 8.8 | 9.57 | 0 | 2 | 6 | 14 | 48 | 1.5 |
|  | 4 | 36 | 9.2 | 8.54 | 0 | 2 | 6 | 14.5 | 28 | 1.5 |
| DP3-84/10 | 1 | 75 | 15.1 | 13.81 | 0 | 4 | 11 | 22 | 50 | 2.8 |
|  | 2 | 59 | 9.3 | 10.02 | 0 | 2 | 6 | 16 | 45 | 1.5 |
|  | 3 | 50 | 8.2 | 8.71 | 0 | 2 | 5 | 12 | 37 | 1.3 |
|  | 4 | 41 | 10.0 | 11.15 | 0 | 2 | 6 | 16 | 50 | 1.5 |
| DP3-25/30 | 1 | 82 | 2.6 | 3.37 | 0 | 0 | 2 | 4 | 14 | 1.7 |
|  | 2 | 78 | 6.4 | 6.06 | 0 | 1 | 5 | 10 | 25 | 4.2 |
|  | 3 | 68 | 7.7 | 6.58 | 0 | 2.5 | 6 | 13 | 25 | 5.0 |
|  | 4 | 66 | 5.8 | 5.57 | 0 | 2 | 5 | 8 | 24 | 4.2 |
|  | 5 | 65 | 4.8 | 5.33 | 0 | 0 | 3 | 6 | 22 | 2.5 |
|  | 6 | 59 | 4.9 | 5.14 | 0 | 1 | 4 | 7 | 25 | 3.4 |
|  | 7 | 54 | 4.9 | 4.47 | 0 | 2 | 4 | 7 | 22 | 3.4 |
|  | 8 | 51 | 4.8 | 4.96 | 0 | 1 | 4 | 7 | 20 | 3.4 |
|  | 9 | 46 | 4.4 | 4.44 | 0 | 1 | 3 | 7 | 19 | 2.5 |
|  | 10 | 42 | 5.7 | 5.36 | 0 | 1 | 4 | 8 | 20 | 3.4 |
|  | 11 | 41 | 3.7 | 3.59 | 0 | 1 | 3 | 6 | 14 | 2.5 |

TABLE 8-continued

Number of Days of Unscheduled Bleeding and/or Spotting Per Cycle,
By Treatment Groups - Complete Cycles Only (Second Clinical Study)

| Regimen (Treatment Group)* | Cycle | N | Mean | SD | Min | Q1 | Median | Q3 | Max | Median Per Monthly Cycle |
|---|---|---|---|---|---|---|---|---|---|---|
| | 12 | 39 | 4.1 | 5.22 | 0 | 0 | 3 | 6 | 20 | 2.5 |
| | 13 | 35 | 4.3 | 4.22 | 0 | 1 | 3 | 6 | 15 | 2.5 |
| Nordette | 1 | 85 | 2.5 | 3.46 | 0 | 0 | 1 | 3 | 18 | |
| | 2 | 80 | 1.9 | 2.27 | 0 | 0 | 1 | 3 | 13 | |
| | 3 | 72 | 1.8 | 2.11 | 0 | 0 | 1 | 3 | 8 | |
| | 4 | 69 | 1.4 | 1.65 | 0 | 0 | 1 | 2 | 8 | |
| | 5 | 67 | 1.4 | 1.93 | 0 | 0 | 1 | 2 | 10 | |
| | 6 | 61 | 1.5 | 1.97 | 0 | 0 | 1 | 2 | 8 | |
| | 7 | 59 | 1.6 | 2.42 | 0 | 0 | 1 | 2 | 11 | |
| | 8 | 57 | 1.6 | 2.70 | 0 | 0 | 1 | 2 | 14 | |
| | 9 | 53 | 1.9 | 2.80 | 0 | 0 | 1 | 2 | 13 | |
| | 10 | 52 | 1.9 | 2.47 | 0 | 0 | 1 | 3 | 9 | |
| | 11 | 49 | 1.2 | 1.43 | 0 | 0 | 1 | 2 | 6 | |
| | 12 | 47 | 1.0 | 1.93 | 0 | 0 | 0 | 1 | 10 | |
| | 13 | 45 | 2.6 | 2.98 | 0 | 1 | 2 | 4 | 14 | |

*Data for all treatment groups are from the second clinical study.

Tables 9 and 10 summarize the average number of days of withdrawal bleeding (defined as scheduled bleeding and/or spotting) per cycle by treatment group. Withdrawal bleeding includes any day for which the patient did not take a combination pill (days 85-91 for the DP3-84/30 and DP3-84/10 treatment groups, and days 26-28 for the DP3-25/30 treatment group). Table 11 summarizes the percentage of patients in the first and second clinical studies who experienced withdrawal bleeding during the withdrawal period.

TABLE 9

Number of Days of Scheduled Bleeding and/or Spotting Per Cycle,
By Treatment Groups - Complete Cycles Only

| Regimen (Treatment Group)* | Cycle | N | Mean | SD | Min | Q1 | Median | Q3 | Max |
|---|---|---|---|---|---|---|---|---|---|
| DP3-84/30 | 1 | 751 | 3.1 | 2.20 | 0 | 1 | 3 | 5 | 7 |
| | 2 | 609 | 2.8 | 2.15 | 0 | 1 | 3 | 4 | 7 |
| | 3 | 515 | 2.5 | 2.14 | 0 | 1 | 2 | 4 | 7 |
| | 4 | 420 | 2.5 | 2.22 | 0 | 0 | 2 | 4 | 7 |
| DP3-84/10 | 1 | 769 | 3.3 | 2.08 | 0 | 2 | 3 | 5 | 7 |
| | 2 | 625 | 3.1 | 2.05 | 0 | 1 | 3 | 5 | 7 |
| | 3 | 531 | 2.8 | 2.02 | 0 | 1 | 3 | 4 | 7 |
| | 4 | 443 | 2.7 | 2.03 | 0 | 1 | 3 | 4 | 7 |
| Seasonale | 1 | 385 | 4.0 | 2.1 | 0 | 3 | 4 | 6 | 7 |
| | 2 | 331 | 3.6 | 2.2 | 0 | 1 | 4 | 6 | 7 |
| | 3 | 296 | 3.4 | 2.2 | 0 | 2 | 4 | 5 | 7 |
| | 4 | 262 | 3.6 | 2.4 | 0 | 2 | 4 | 6 | 7 |
| Nordette | 1 | 214 | 3.4 | 1.5 | 0 | 3 | 3 | 4 | 7 |
| | 2 | 210 | 3.1 | 1.6 | 0 | 2 | 3 | 4 | 7 |
| | 3 | 204 | 3.1 | 1.6 | 0 | 2 | 3 | 4 | 7 |
| | 4 | 194 | 3.0 | 1.7 | 0 | 2 | 3 | 4 | 7 |
| | 5 | 188 | 3.0 | 1.7 | 0 | 2 | 3 | 4 | 7 |
| | 6 | 184 | 2.9 | 1.7 | 0 | 2 | 3 | 4 | 7 |
| | 7 | 178 | 2.8 | 1.5 | 0 | 2 | 3 | 4 | 6 |
| | 8 | 177 | 2.9 | 1.8 | 0 | 2 | 3 | 4 | 7 |
| | 9 | 172 | 2.9 | 1.6 | 0 | 2 | 3 | 4 | 6 |
| | 10 | 170 | 2.7 | 1.7 | 0 | 1 | 3 | 4 | 7 |
| | 11 | 163 | 2.7 | 1.7 | 0 | 2 | 3 | 4 | 6 |
| | 12 | 162 | 2.7 | 1.7 | 0 | 1 | 3 | 4 | 7 |
| | 13 | 159 | 3.3 | 1.9 | 0 | 2 | 3 | 5 | 7 |

*Data for the treatment groups DP3-84/30 and DP3-84/10 are from the first clinical study. Seasonale and Nordette data are from the third clinical study.

TABLE 10

Number of Days of Scheduled Bleeding and/or Spotting Per Cycle, By Treatment Groups - Complete Cycles Only (Second Clinical Study)

| Regimen (Treatment Group)* | Cycle | N | Mean | SD | Min | Q1 | Median | Q3 | Max |
|---|---|---|---|---|---|---|---|---|---|
| DP3-84/30 | 1 | 70 | 3.4 | 2.17 | 0 | 2 | 4 | 5 | 7 |
| | 2 | 54 | 2.4 | 2.03 | 0 | 0 | 2 | 4 | 6 |
| | 3 | 45 | 2.6 | 2.03 | 0 | 1 | 3 | 4 | 7 |
| | 4 | 36 | 2.8 | 2.07 | 0 | 1 | 2.5 | 4.5 | 7 |
| DP3-84/10 | 1 | 75 | 3.3 | 2.15 | 0 | 2 | 3 | 5 | 7 |
| | 2 | 59 | 2.7 | 2.39 | 0 | 0 | 3 | 5 | 7 |
| | 3 | 50 | 3.0 | 2.29 | 0 | 1 | 3 | 5 | 7 |
| | 4 | 41 | 3.0 | 2.47 | 0 | 1 | 2 | 5 | 7 |
| DP3-25/30 | 1 | 82 | 0.5 | 0.88 | 0 | 0 | 0 | 1 | 3 |
| | 2 | 78 | 0.7 | 1.13 | 0 | 0 | 0 | 1 | 3 |
| | 3 | 68 | 0.9 | 1.18 | 0 | 0 | 0 | 2 | 3 |
| | 4 | 66 | 0.6 | 1.05 | 0 | 0 | 0 | 1 | 3 |
| | 5 | 65 | 0.6 | 0.90 | 0 | 0 | 0 | 1 | 3 |
| | 6 | 59 | 0.8 | 1.09 | 0 | 0 | 0 | 2 | 3 |
| | 7 | 54 | 0.7 | 1.04 | 0 | 0 | 0 | 1 | 3 |
| | 8 | 51 | 0.6 | 0.87 | 0 | 0 | 0 | 1 | 3 |
| | 9 | 46 | 0.4 | 0.68 | 0 | 0 | 0 | 1 | 3 |
| | 10 | 42 | 0.7 | 1.12 | 0 | 0 | 0 | 1 | 3 |
| | 11 | 41 | 0.4 | 0.83 | 0 | 0 | 0 | 0 | 3 |
| | 12 | 39 | 0.4 | 0.74 | 0 | 0 | 0 | 1 | 3 |
| | 13 | 35 | 0.7 | 0.96 | 0 | 0 | 0 | 1 | 3 |
| Nordette | 1 | 85 | 3.2 | 1.76 | 0 | 2 | 3 | 4 | 7 |
| | 2 | 80 | 3.0 | 1.72 | 0 | 2 | 3 | 4 | 7 |
| | 3 | 72 | 2.9 | 1.68 | 0 | 2 | 3 | 4 | 7 |
| | 4 | 69 | 2.7 | 1.72 | 0 | 1 | 3 | 4 | 6 |
| | 5 | 67 | 2.5 | 1.63 | 0 | 1 | 2 | 4 | 5 |
| | 6 | 61 | 2.7 | 1.78 | 0 | 1 | 3 | 4 | 7 |
| | 7 | 59 | 2.7 | 2.01 | 0 | 1 | 3 | 4 | 7 |
| | 8 | 57 | 2.6 | 2.00 | 0 | 1 | 3 | 4 | 7 |
| | 9 | 53 | 2.8 | 1.69 | 0 | 2 | 3 | 4 | 6 |
| | 10 | 52 | 2.6 | 1.83 | 0 | 1 | 3 | 4 | 7 |
| | 11 | 49 | 2.7 | 1.73 | 0 | 2 | 3 | 4 | 7 |
| | 12 | 47 | 2.7 | 1.66 | 0 | 1 | 3 | 4 | 6 |
| | 13 | 45 | 2.9 | 2.01 | 0 | 1 | 3 | 4 | 7 |

*Data for all treatment groups are from the first clinical study.

TABLE 11

Percentage of Patients Reporting Bleeding and/or Spotting During the Scheduled Withdrawal Bleeding Period.

| Clinical Study | Regimen (Treatment Group) | Cycle | Number of Complete Cycles | N | (%) |
|---|---|---|---|---|---|
| | DP3-84/30 | 1 | 751 | 630 | (83.9) |
| | | 2 | 609 | 481 | (79.0) |
| | | 3 | 515 | 390 | (75.7) |
| | | 4 | 420 | 304 | (72.4) |
| | DP3-84/10 | 1 | 769 | 659 | (85.7) |
| | | 2 | 625 | 530 | (84.8) |
| | | 3 | 531 | 430 | (81.0) |
| | | 4 | 443 | 361 | (81.5) |
| Second | DP3-84/30 | 1 | 70 | 59 | (84.3) |
| | | 2 | 54 | 40 | (74.1) |
| | | 3 | 45 | 35 | (77.8) |
| | | 4 | 36 | 32 | (88.9) |
| | DP3-84/10 | 1 | 75 | 64 | (85.3) |
| | | 2 | 59 | 41 | (69.5) |
| | | 3 | 50 | 40 | (80.0) |
| | | 4 | 41 | 32 | (78.0) |
| | DP3-25/30 | 1 | 82 | 21 | (25.6) |
| | | 2 | 78 | 25 | (32.1) |
| | | 3 | 68 | 27 | (39.7) |
| | | 4 | 66 | 22 | (33.3) |
| | | 5 | 65 | 22 | (33.8) |
| | | 6 | 59 | 23 | (39.0) |
| | | 7 | 54 | 20 | (37.0) |
| | | 8 | 51 | 20 | (39.2) |
| | | 9 | 46 | 14 | (30.4) |
| | | 10 | 42 | 14 | (33.3) |
| | | 11 | 41 | 9 | (22.0) |
| | | 12 | 39 | 10 | (25.6) |
| | | 13 | 35 | 16 | (45.7) |
| | Nordette | 1 | 85 | 75 | (88.2) |
| | | 2 | 80 | 72 | (90.0) |
| | | 3 | 72 | 65 | (90.3) |
| | | 4 | 69 | 60 | (87.0) |
| | | 5 | 67 | 56 | (83.6) |
| | | 6 | 61 | 53 | (86.9) |
| | | 7 | 59 | 47 | (79.7) |
| | | 8 | 57 | 44 | (77.2) |
| | | 9 | 53 | 46 | (86.8) |
| | | 10 | 52 | 43 | (82.7) |
| | | 11 | 49 | 41 | (83.7) |
| | | 12 | 47 | 41 | (87.2) |
| | | 13 | 45 | 38 | (84.4) |

Table 12 presents the percentage of patients in each treatment group who reported no bleeding and/or spotting during the defined withdrawal bleeding period. Data from both the first and second clinical studies are presented. Table 13 presents the percentage of patients in each treatment group from the first clinical study who did not report any bleeding and/or spotting during the entire cycle. Table 13 also presents the percentage of patients in the Seasonale and Nordette treatment groups in the third clinical study who reported no bleeding and/or spotting during the entire cycle.

TABLE 12

Percentage of Patients Not Reporting Bleeding and/or Spotting During the Scheduled Withdrawal Bleeding Period.

| Clinical Study | Regimen (Treatment Group) | Cycle | Number of Complete Cycles | N | (%) |
|---|---|---|---|---|---|
| First | DP3-84/30 | 1 | 751 | 121 | (16.1) |
| | | 2 | 609 | 128 | (21.0) |
| | | 3 | 515 | 125 | (24.3) |
| | | 4 | 420 | 116 | (27.6) |
| | DP3-84/10 | 1 | 769 | 110 | (14.3) |
| | | 2 | 625 | 95 | (15.2) |
| | | 3 | 531 | 101 | (19.0) |
| | | 4 | 443 | 82 | (18.5) |
| Second | DP3-84/30 | 1 | 70 | 11 | (15.7) |
| | | 2 | 54 | 14 | (25.9) |
| | | 3 | 45 | 10 | (22.2) |
| | | 4 | 36 | 4 | (11.1) |
| | DP3-84/10 | 1 | 75 | 11 | (14.7) |
| | | 2 | 59 | 18 | (30.5) |
| | | 3 | 50 | 10 | (20.0) |
| | | 4 | 41 | 9 | (22.0) |
| | DP3-25/30 | 1 | 82 | 61 | (74.4) |
| | | 2 | 78 | 53 | (67.9) |
| | | 3 | 68 | 41 | (60.3) |
| | | 4 | 66 | 44 | (66.7) |
| | | 5 | 65 | 43 | (66.2) |
| | | 6 | 59 | 36 | (61.0) |
| | | 7 | 54 | 34 | (63.0) |
| | | 8 | 51 | 31 | (60.8) |
| | | 9 | 46 | 32 | (69.6) |
| | | 10 | 42 | 28 | (66.7) |
| | | 11 | 41 | 32 | (78.0) |
| | | 12 | 39 | 29 | (74.4) |
| | | 13 | 35 | 19 | (54.3) |
| | Nordette | 1 | 85 | 10 | (11.8) |
| | | 2 | 80 | 8 | (10.0) |
| | | 3 | 72 | 7 | (9.7) |
| | | 4 | 69 | 9 | (13.0) |
| | | 5 | 67 | 11 | (16.4) |
| | | 6 | 61 | 8 | (13.1) |
| | | 7 | 59 | 12 | (20.3) |
| | | 8 | 57 | 13 | (22.8) |
| | | 9 | 53 | 7 | (13.2) |
| | | 10 | 52 | 9 | (17.3) |
| | | 11 | 49 | 8 | (16.3) |
| | | 12 | 47 | 6 | (12.8) |
| | | 13 | 45 | 7 | (15.6) |

TABLE 13

Percentage of Patients Not Reporting Bleeding and/or Spotting During a Cycle.

| Clinical Study | Regimen (Treatment Group) | Cycle | Number of Complete Cycles | N | (%) |
|---|---|---|---|---|---|
| First | DP3-84/30 | 1 | 751 | 24 | (3.2) |
| | | 2 | 609 | 23 | (3.8) |
| | | 3 | 515 | 23 | (4.5) |
| | | 4 | 420 | 33 | (7.9) |
| | DP3-84/10 | 1 | 769 | 16 | (2.1) |
| | | 2 | 625 | 28 | (4.5) |
| | | 3 | 531 | 33 | (6.2) |
| | | 4 | 443 | 28 | (6.3) |
| Third | Seasonale | 1 | 385 | 4 | (1.0) |
| | | 2 | 331 | 6 | (1.8) |
| | | 3 | 296 | 11 | (3.7) |
| | | 4 | 262 | 9 | (3.4) |
| | Nordette | 1 | 214 | 6 | (2.8) |
| | | 2 | 210 | 5 | (2.3) |
| | | 3 | 204 | 13 | (6.4) |
| | | 4 | 194 | 11 | (5.7) |
| | | 5 | 188 | 8 | (543) |
| | | 6 | 184 | 7 | (3.8) |
| | | 7 | 178 | 10 | (5.6) |

TABLE 13-continued

Percentage of Patients Not Reporting Bleeding
and/or Spotting During a Cycle.

| Clinical Study | Regimen (Treatment Group) | Cycle | Number of Complete Cycles | N | (%) |
|---|---|---|---|---|---|
| | | 8 | 177 | 16 | (9.0) |
| | | 9 | 172 | 12 | (7.0) |
| | | 10 | 170 | 12 | (7.1) |
| | | 11 | 163 | 10 | (6.1) |
| | | 12 | 162 | 9 | (5.6) |
| | | 13 | 159 | 11 | (6.9) |

Figure 2:
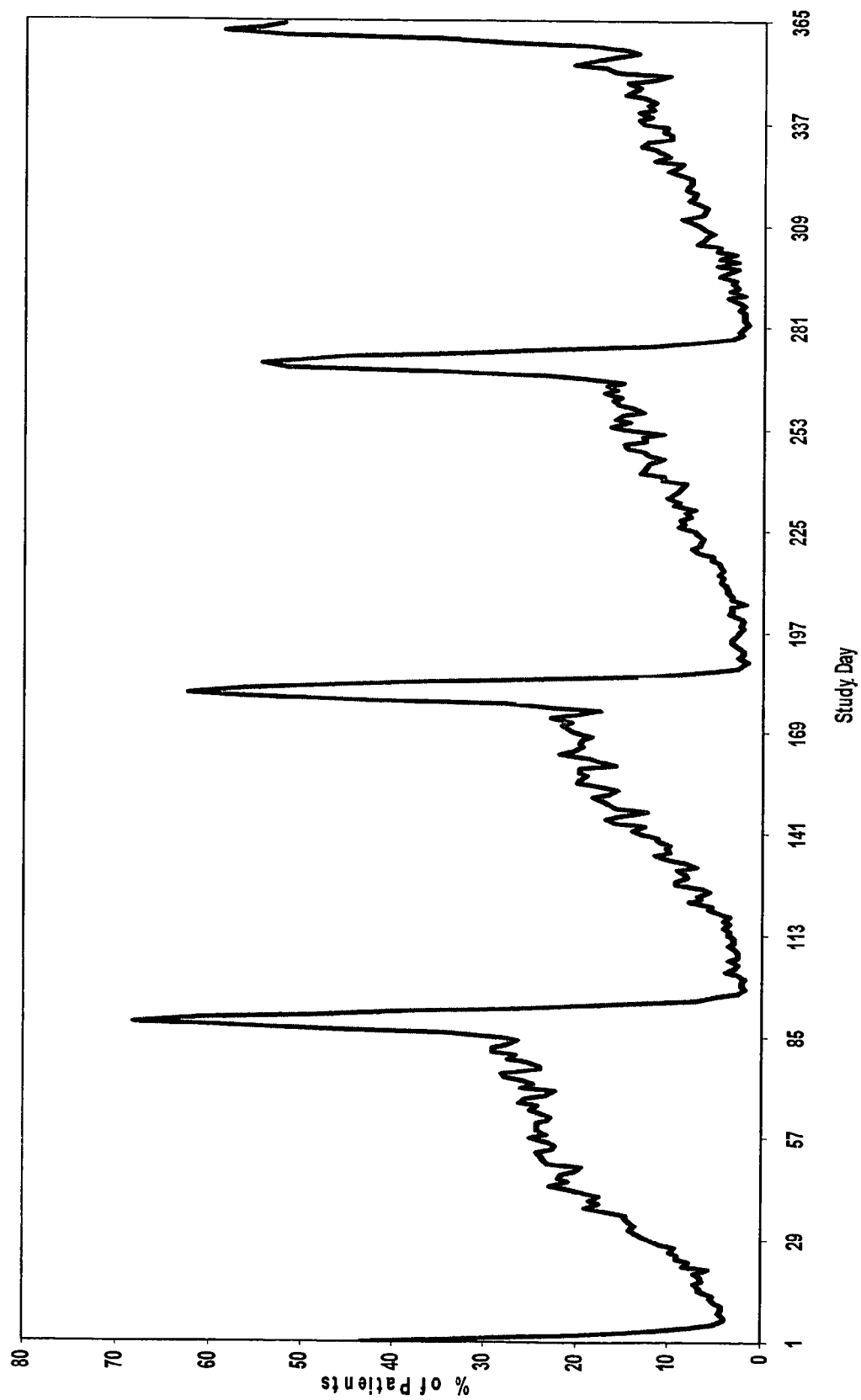
FIG. 2 shows the distribution of bleeding and spotting reported by patients administered the DP3-84/10 regimen during the first clinical study described in Example 7.
Figure 3:
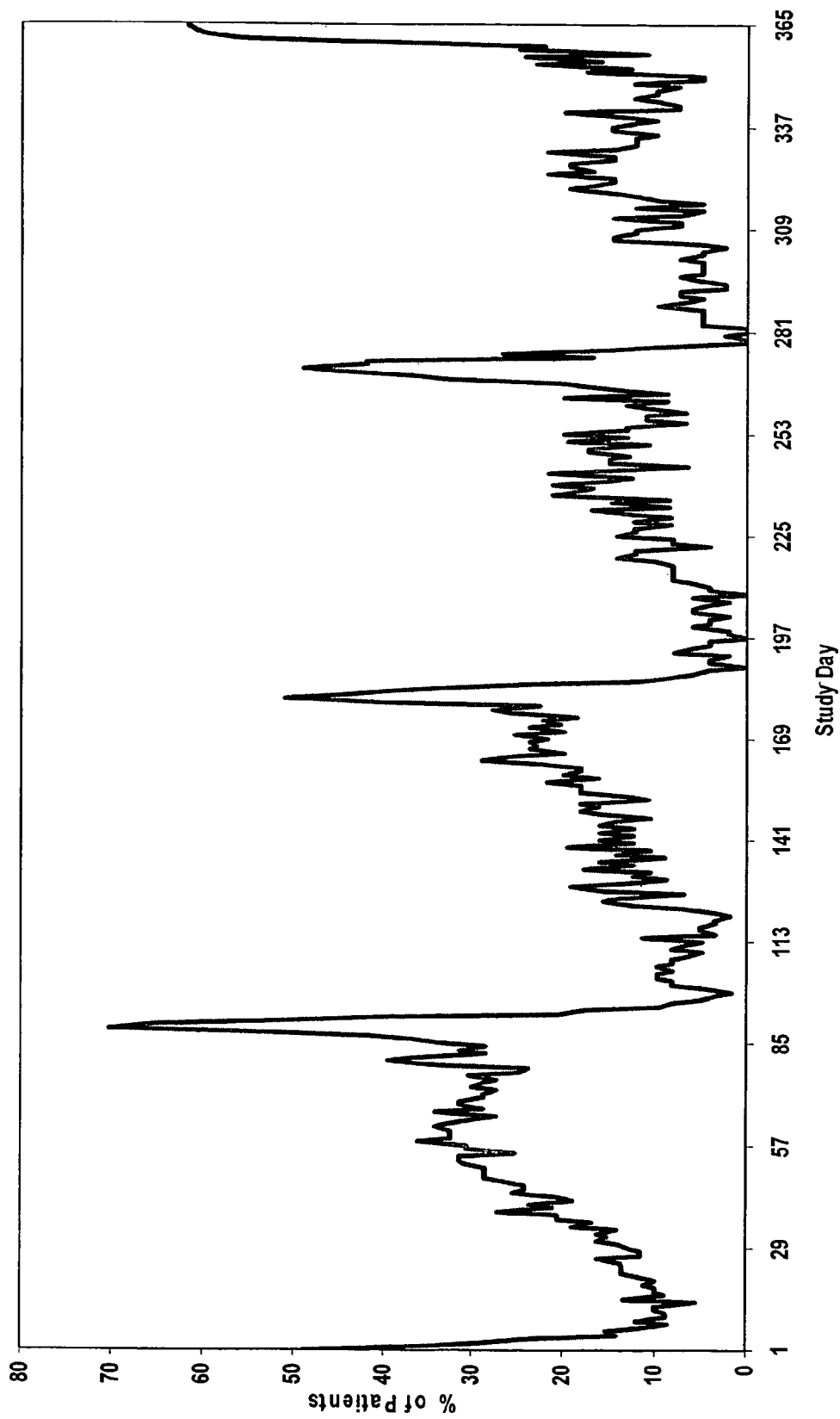
FIG. 3 shows the distribution of bleeding and spotting reported by patients administered the DP3-84/30 regimen during the second clinical study described in Example 7.
Figure 4:
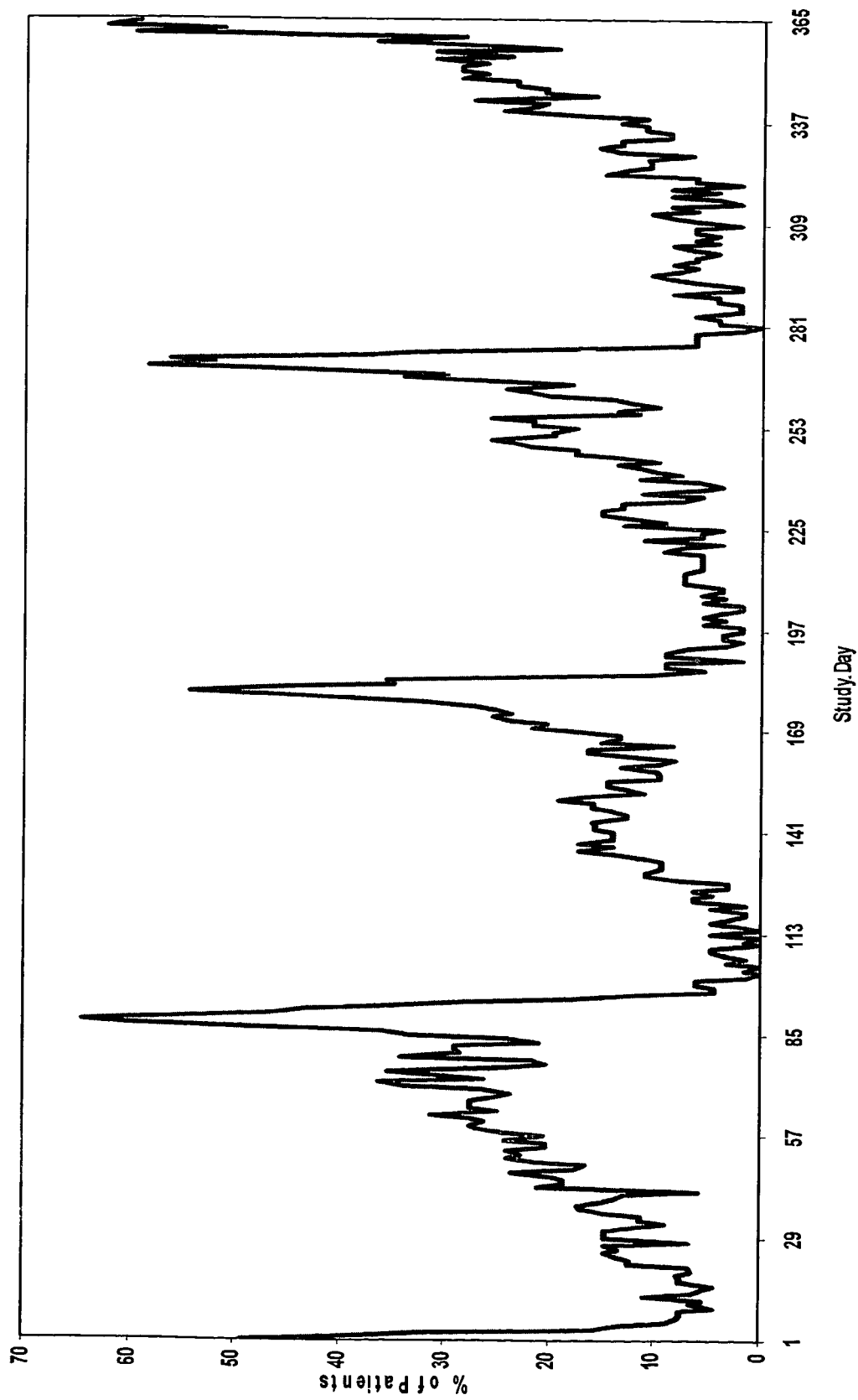
FIG. 4 shows the distribution of bleeding and spotting reported by patients administered the DP3-84/10 regimen during the second clinical study described in Example 7.
Figure 5:
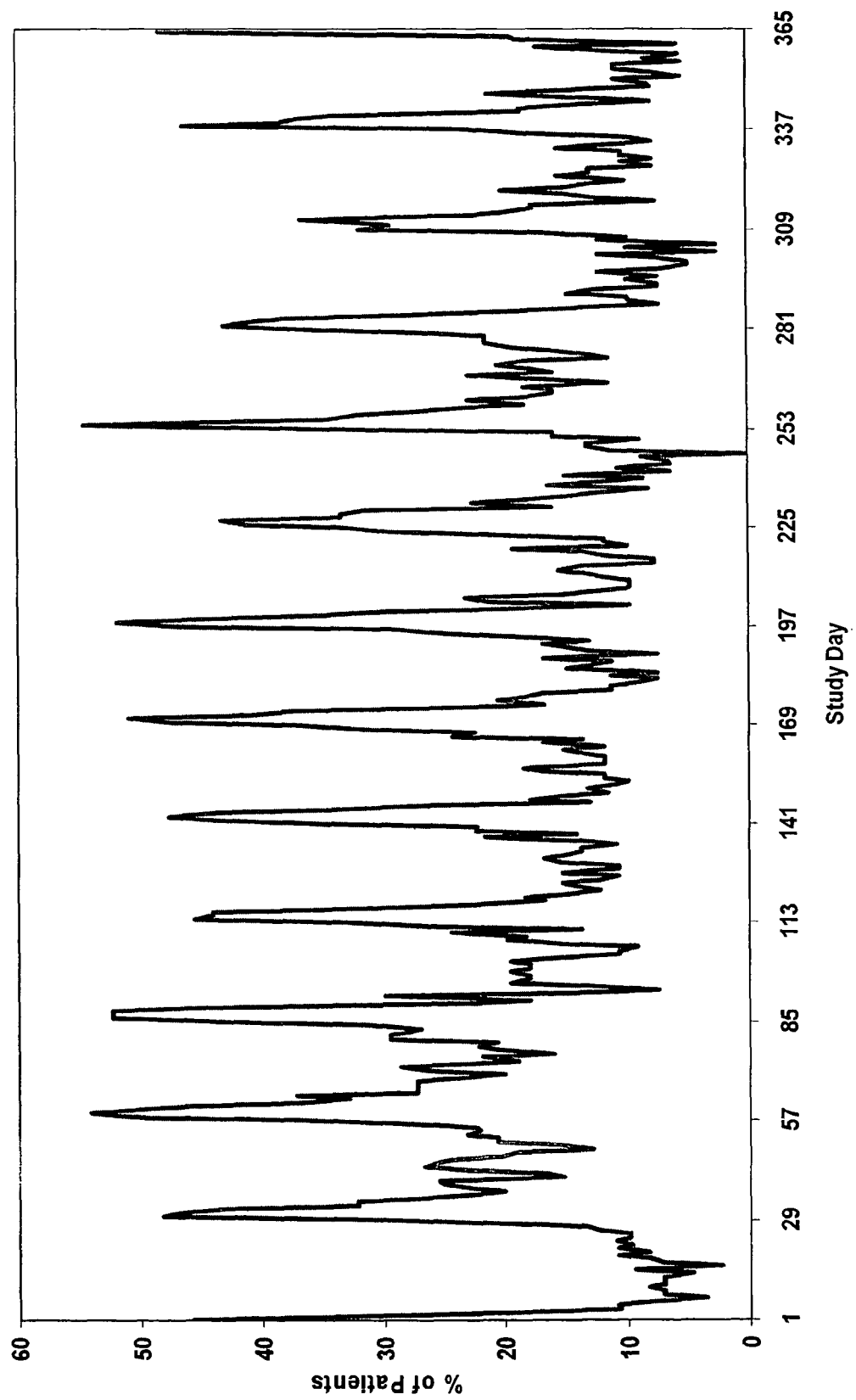
FIG. 5 shows the distribution of bleeding and spotting reported by patients administered the DP3-25/30 regimen during the second clinical study described in Example 7.
Figure 6:
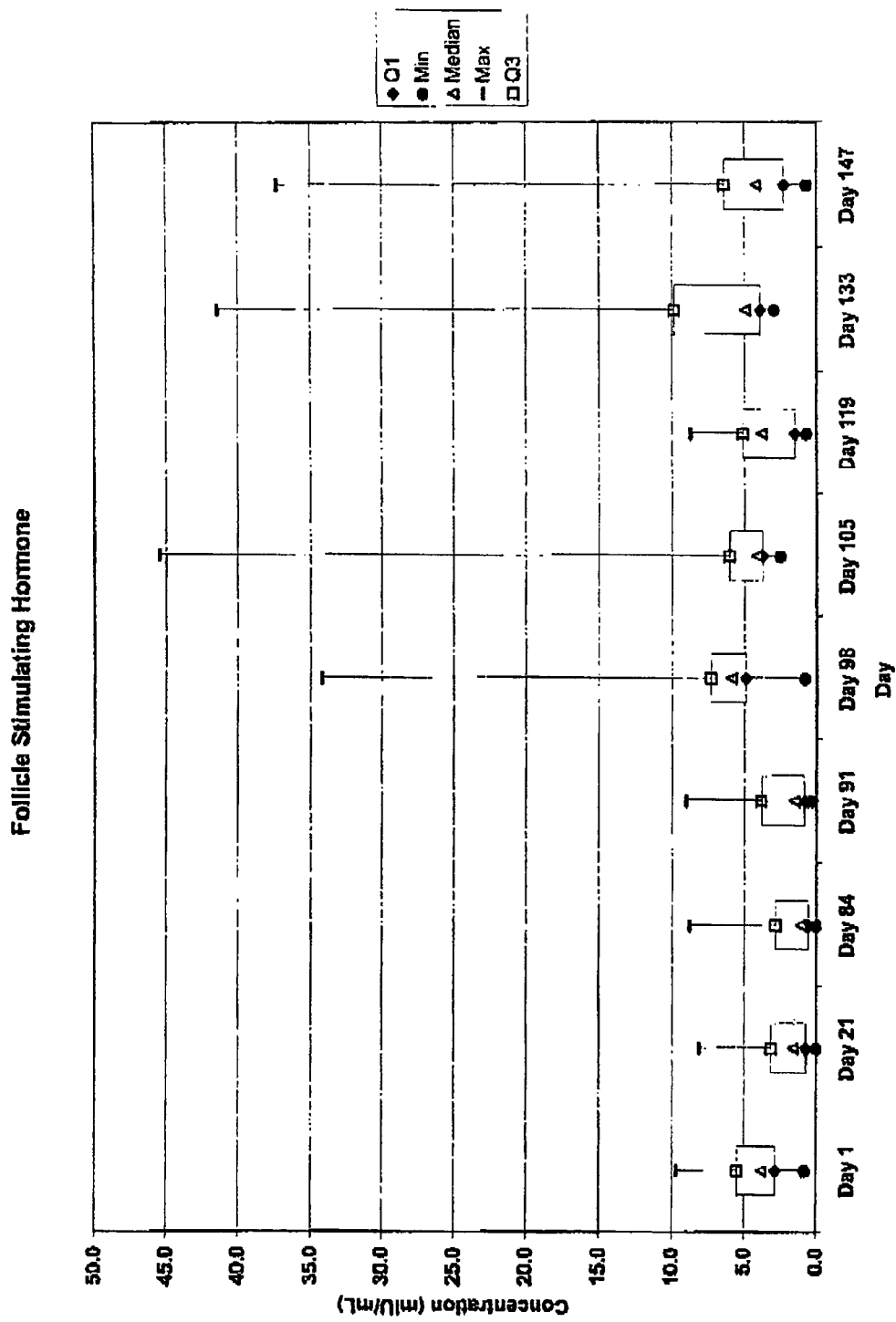
FIG. 6 shows the plasma concentration of Follicle Stimulating Hormone (FSH) in patients during daily administration of levonorgestrel (0.150 mg)/ethinyl estradiol (0.030 mg) tablets for 84 consecutive days, followed by daily administration of ethinyl estradiol (0.030 mg) tablets for 7 days, as described in Example 10.
Figure 7:
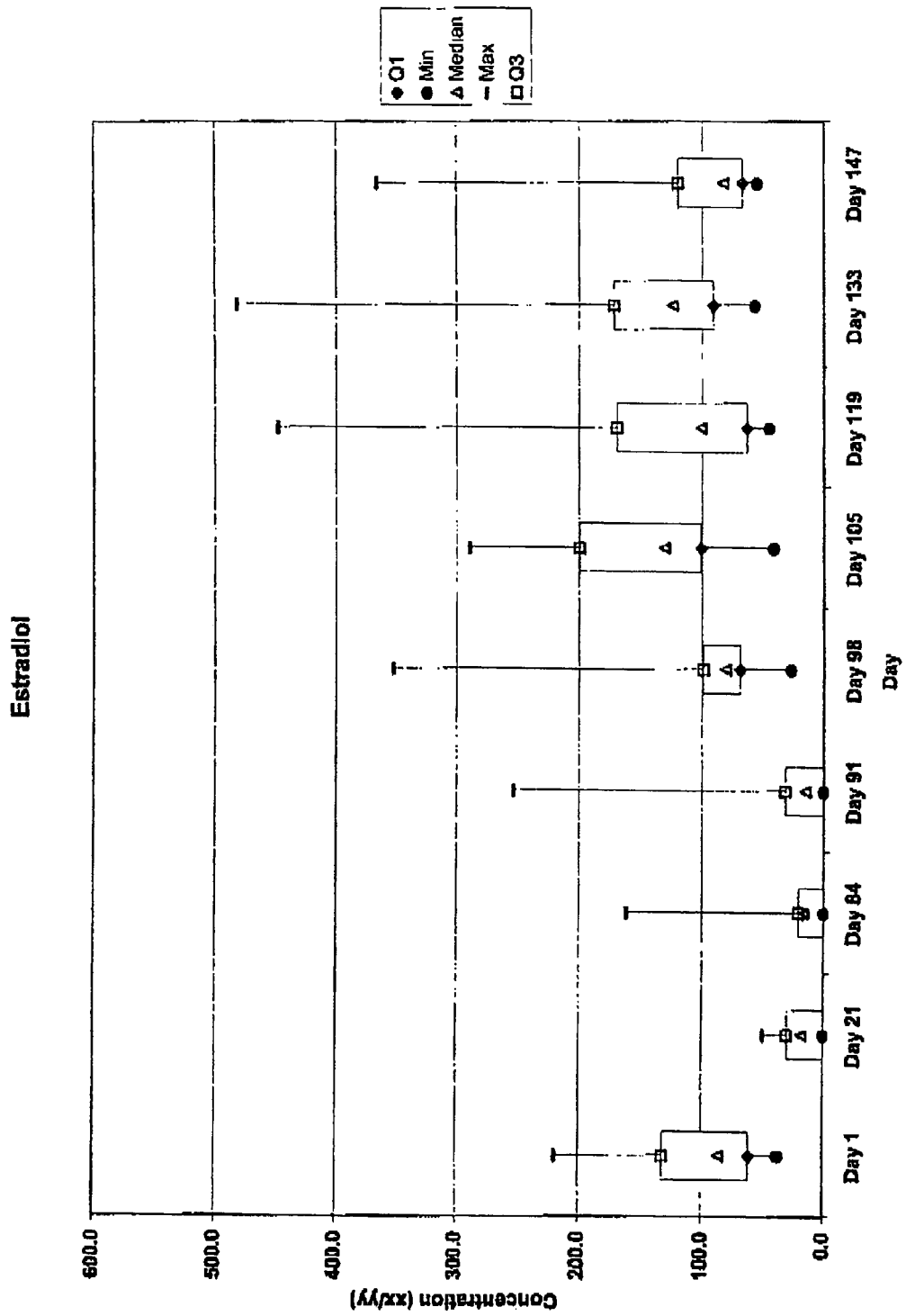
FIG. 7 shows the plasma concentration of estradiol in patients during daily administration of levonorgestrel (0.150 mg)/ethinyl estradiol (0.030 mg) tablets for 84 consecutive days, followed by daily administration of ethinyl estradiol (0.030 mg) tablets for 7 days, as described in Example 10.
Figure 8:
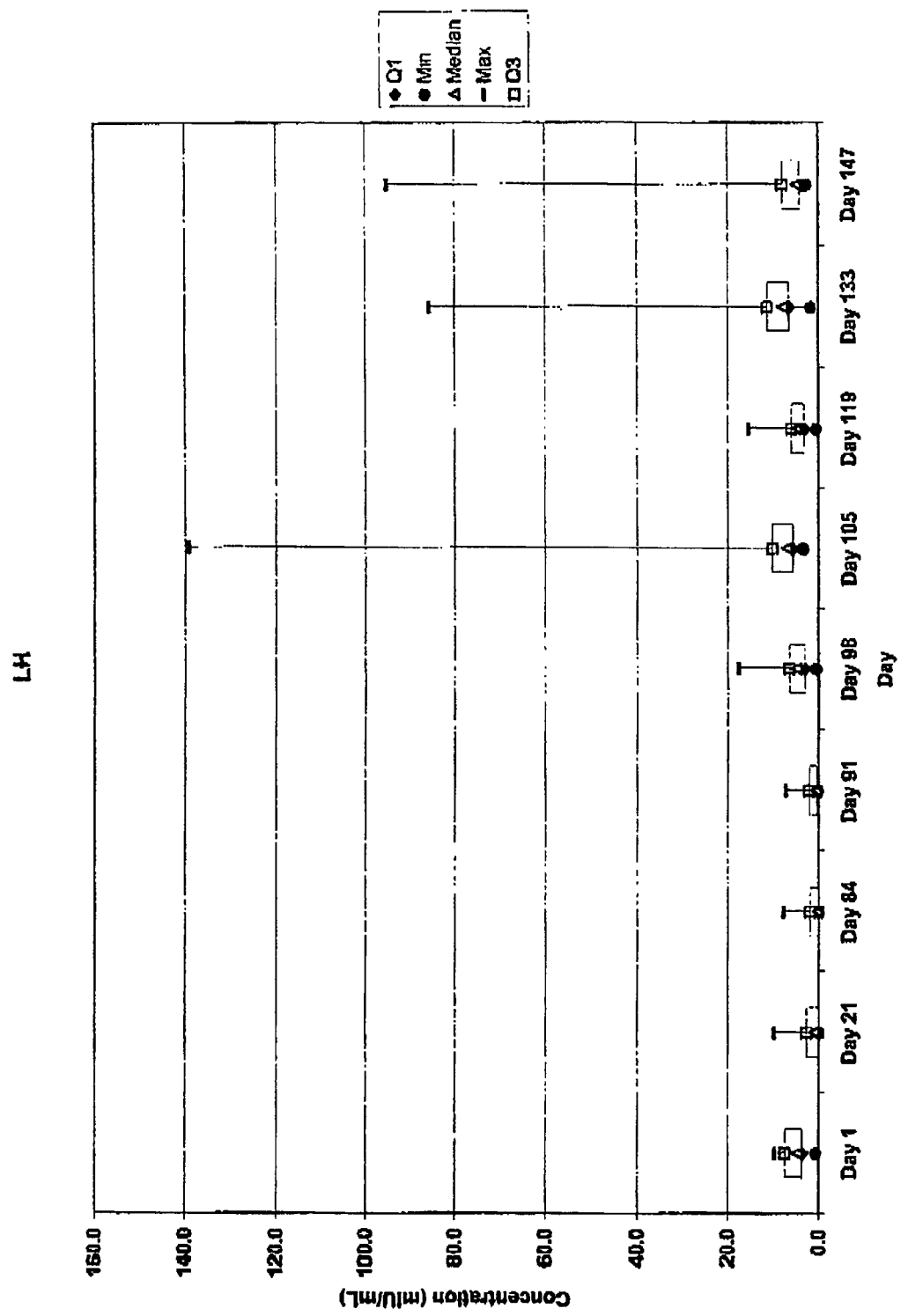
FIG. 8 shows the plasma concentration of Luteinizing Hormone (LH) in patients during daily administration of levonorgestrel (0.150 mg)/ethinyl estradiol (0.030 mg) tablets for 84 consecutive days, followed by daily administration of ethinyl estradiol (0.030 mg) tablets for 7 days, as described in Example 10.
Figure 9:
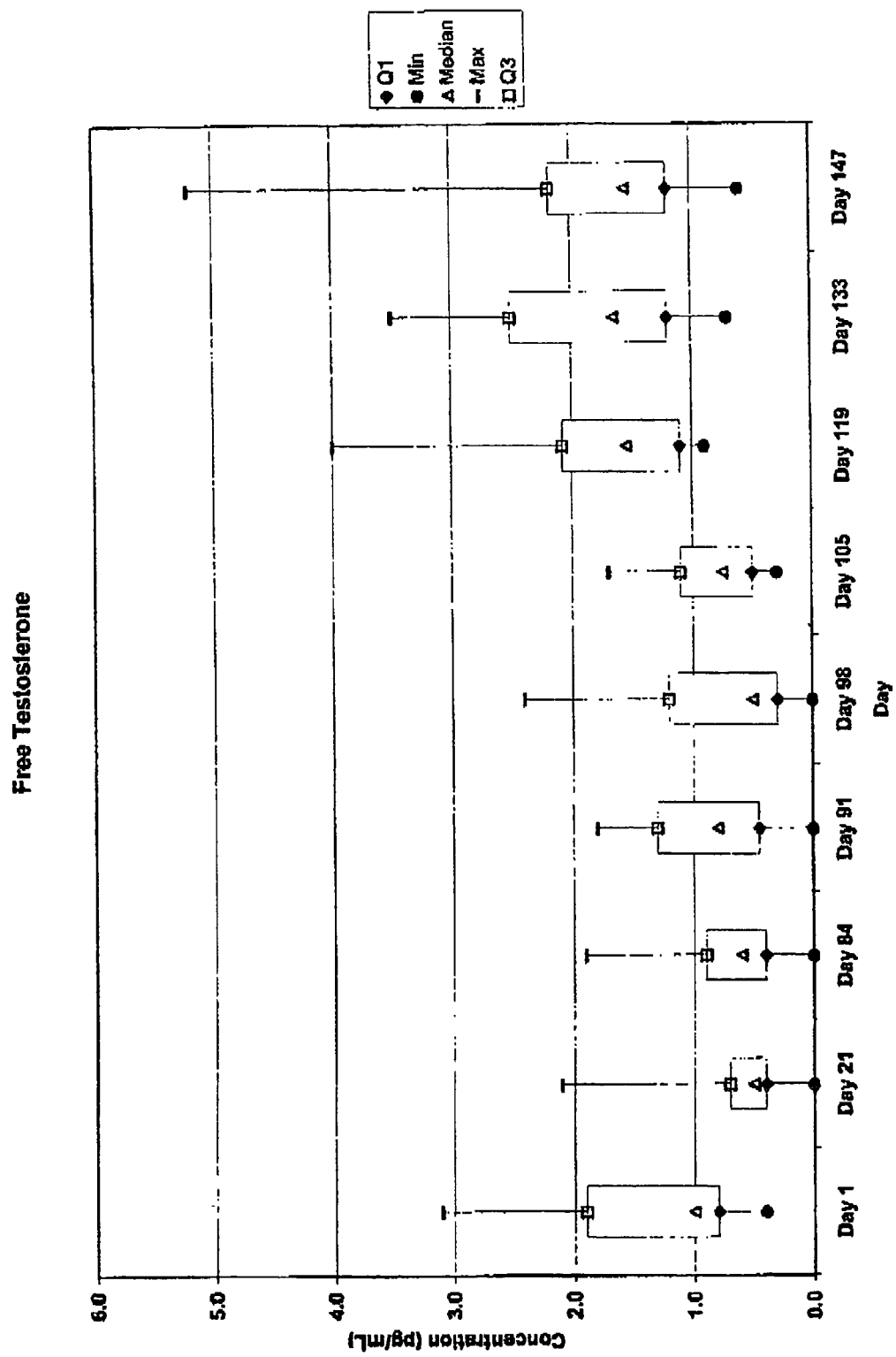
FIG. 9 shows the plasma concentration of free testosterone in patients during daily administration of levonorgestrel (0.150 mg)/ethinyl estradiol (0.030 mg) tablets for 84 consecutive days, followed by daily administration of ethinyl estradiol (0.030 mg) tablets for 7 days, as described in Example 10.

FIGS. 1 through 5 show the distribution of bleeding and spotting among patients in the various treatment groups from the first and second clinical studies. FIGS. 1 and 2 present data for patients from the DP3-84/30 and DP3-84/10 treatment groups, respectively, from the first clinical study. FIGS. 3, 4, and 5 present data for patients from the DP3-84/30, DP3-84/10, and DP3-25/30 treatment groups from the second clinical study.

Example 8

Adverse events reported by patients during the course of the clinical studies of Example 7 were recorded. An "adverse event" was defined as any reaction, side effect, or other undesirable event that occurred in conjunction with the use of the drug, biological product or diagnostic agent during the study, whether or not the event was considered to be related to the study drug (see the protocol in Example 5). The percentage of patients in the first and second clinical studies reporting certain adverse events are presented in Tables 14 through 20. Each table also includes similar data from the third clinical study.

Tables 14 and 15 present the percentage of patients in the first and second clinical studies who reported menorrhagia and dysmenorrhea as adverse events. Corresponding data from the third clinical study are also presented. The adverse event coding (MedDRA) may have varied between the first and third clinical studies, so that some of the adverse event reports in the first clinical study that could have been identified as menorrhagia may have been identified as intermenstrual bleeding.

TABLE 14

Incidence of Menorrhagia, by Treatment Group and Study

| Clinical Study | Regimen (Treatment Group) | N | (%) |
|---|---|---|---|
| First | DP3-84/30 | 80 | (8.90) |
| | DP3-84/10 | 61 | (6.79) |
| Third | Seasonale | 53 | (11.6) |
| | Nordette | 6 | (2.7) |
| Second | DP3-84/30 | 7 | (7.6) |
| | DP3-84/10 | 4 | (4.3) |
| | DP3-25/30 | 2 | (2.3) |
| | Nordette | 2 | (2.3) |

TABLE 15

Incidence of Dysmenorrhoea, by Treatment Group and Study

| Clinical Study | Regimen (Treatment Group) | N | (%) |
|---|---|---|---|
| First | DP3-84/30 | 40 | (4.5) |
| | DP3-84/10 | 37 | (4.1) |
| Third | Seasonale | 26 | (5.7) |
| | Nordette | 9 | (4.0) |
| Second | DP3-84/30 | 3 | (3.3) |
| | DP3-84/10 | 2 | (2.1) |
| | DP3-25/30 | 1 | (1.1) |
| | Nordette | 4 | (4.5) |

Table 16 presents the percentage of patients in the first and second clinical studies who reported acne as an adverse event. The data include all reports of "Acne NOS," "Acne Aggravated," or "Acne Cystic" as adverse events. ("NOS" refers to "no other symptom.") Corresponding data from the third clinical study are also included.

TABLE 16

Incidence of Acne, by Treatment Group and Study

| Clinical Study | Regimen (Treatment Group) | N | (%) |
|---|---|---|---|
| First | DP3-84/30 | 57 | (6.3) |
| | DP3-84/10 | 54 | (6.0) |
| Third | Seasonale | 21 | (4.6) |
| | Nordette | 10 | (4.4) |
| Second | DP3-84/30 | 3 | (3.3) |
| | DP3-84/10 | 9 | (9.6) |
| | DP3-25/30 | 2 | (2.3) |
| | Nordette | 2 | (2.3) |

Table 17 presents the percentage of patients in the first and second clinical studies who reported the following categories of infections as adverse events:

"Bladder Infection NOS"
"Nasopharyngitis" (including "Pharyngitis Streptococcal")
"Sinusitis NOS" (including "Sinusitis Acute NOS")
URI (including "Upper Respiratory Tract Infection NOS"; "Upper Respiratory Tract Infection Viral NOS"; and "Respiratory Tract Infection NOS")
UTI (including "Urinary Tract Infection NOS"; and "Urinary Tract Infection bacterial NOS)"
"Vaginitis NOS" (including "Vaginitis Bacterial NOS; and Vulvovaginitis NOS")
"Vaginosis Fungal NOS"

Corresponding data from the third clinical study are also included.

TABLE 17

Incidence of Infection, by Treatment Group and Study

| Infection | Study | Regimen (Treatment Group) | N | (%) |
|---|---|---|---|---|
| Bladder Infection | First | DP3-84/30 | 10 | (1.1) |
| | | DP3-84/10 | 10 | (1.1) |
| | Third | Seasonale | 6 | (1.3) |
| | | Nordette | 7 | (3.1) |
| | Second | DP3-84/30 | 0 | |

TABLE 17-continued

Incidence of Infection, by Treatment Group and Study

| Infection | Study | Regimen (Treatment Group) | N | (%) |
|---|---|---|---|---|
| | | DP3-84/10 | 0 | |
| | | DP3-25/30 | 0 | |
| | | Nordette | 1 | (1.1) |
| Nasopharyngitis | First | DP3-84/30 | 98 | (10.9) |
| | | DP3-84/10 | 103 | (11.5) |
| | Third | Seasonale | 106 | (23.2) |
| | | Nordette | 70 | (31.0) |
| | Second | DP3-84/30 | 17 | (18.5) |
| | | DP3-84/10 | 13 | (13.8) |
| | | DP3-25/30 | 14 | (16.1) |
| | | Nordette | 13 | (14.8) |
| Sinusitis | First | DP3-84/30 | 66 | (7.3) |
| | | DP3-84/10 | 65 | (7.2) |
| | Third | Seasonale | 46 | (10.1) |
| | | Nordette | 25 | (11.1) |
| | Second | DP3-84/30 | 1 | (1.1) |
| | | DP3-84/10 | 7 | (7.4) |
| | | DP3-25/30 | 4 | (4.6) |
| | | Nordette | 3 | (3.4) |
| URI | First | DP3-84/30 | 43 | (4.8) |
| | | DP3-84/10 | 54 | (6.0) |
| | Third | Seasonale | 29 | (6.4) |
| | | Nordette | 24 | (10.6) |
| | Second | DP3-84/30 | 1 | (1.1) |
| | | DP3-84/10 | 5 | (5.3) |
| | | DP3-25/30 | 3 | (3.4) |
| | | Nordette | 1 | (1.1) |
| UTI | First | DP3-84/30 | 36 | (4.0) |
| | | DP3-84/10 | 45 | (5.0) |
| | Third | Seasonale | 20 | (4.4) |
| | | Nordette | 14 | (6.2) |
| | Second | DP3-84/30 | 2 | (2.2) |
| | | DP3-84/10 | 5 | (5.3) |
| | | DP3-25/30 | 6 | (6.9) |
| | | Nordette | 7 | (8.0) |
| Vaginitis | First | DP3-84/30 | 16 | (1.8) |
| | | DP3-84/10 | 22 | (2.5) |
| | Third | Seasonale | 11 | (2.4) |
| | | Nordette | 5 | (2.2) |
| | Second | DP3-84/30 | 2 | (2.2) |
| | | DP3-84/10 | 5 | (5.3) |
| | | DP3-25/30 | 3 | (3.4) |
| | | Nordette | 4 | (4.5) |
| Vaginosis | First | DP3-84/30 | 25 | (2.8) |
| | | DP3-84/10 | 20 | (2.2) |
| | Third | Seasonale | 9 | (2.0) |
| | | Nordette | 4 | (1.8) |
| | Second | DP3-84/30 | 2 | (2.2) |
| | | DP3-84/10 | 1 | (1.1) |
| | | DP3-25/30 | 3 | (3.4) |
| | | Nordette | 1 | (1.1) |

Table 18 presents the percentage of patients in the first and second clinical studies who reported headache as an adverse event. The data include all reports of "Headache NOS," "Tension Headache," "Sinus Headache," and "Headache NOS Aggravated" as adverse events. Data from the third clinical study is also included.

TABLE 18

Incidence of Headache, by Treatment Group and Study

| Study | Regimen (Treatment Group) | N | (%) |
|---|---|---|---|
| First | DP3-84/30 | 63 | (7.0) |
| | DP3-84/10 | 58 | (6.5) |
| Third | Seasonale | 110 | (24.1) |
| | Nordette | 79 | (35.0) |

TABLE 18-continued

Incidence of Headache, by Treatment Group and Study

| Study | Regimen (Treatment Group) | N | (%) |
|---|---|---|---|
| Second | DP3-84/30 | 8 | (8.7) |
| | DP3-84/10 | 4 | (4.3) |
| | DP3-25/30 | 7 | (8.0) |
| | Nordette | 5 | (5.7) |

Table 19 presents the percentage of patients in the first and second clinical studies who reported nausea as an adverse event. The data include all reports of "Nausea" and Nausea Aggravated" as adverse events. Data from the third clinical study is also included.

TABLE 19

Incidence of Nausea, by Treatment Group and Study

| Study | Regimen (Treatment Group) | N | (%) |
|---|---|---|---|
| First | DP3-84/30 | 51 | (5.7) |
| | DP3-84/10 | 47 | (5.2) |
| Third | Seasonale | 34 | (7.5) |
| | Nordette | 21 | (9.3) |
| Second | DP3-84/30 | 5 | (5.4) |
| | DP3-84/10 | 3 | (3.2) |
| | DP3-25/30 | 2 | (2.3) |
| | Nordette | 6 | (6.8) |

Table 20 presents the percentage of patients in the first and second clinical studies who reported depression as an adverse event. The data include all reports of "Depression" and "Depression Aggravated" as adverse events. Data from the third clinical study is also included.

TABLE 20

Incidence of Depression, by Treatment Group and Study

| Study | Regimen (Treatment Group) | N | (%) |
|---|---|---|---|
| First | DP3-84/30 | 35 | (3.9) |
| | DP3-84/10 | 38 | (4.2) |
| Third | Seasonale | 10 | (2.2) |
| | Nordette | 14 | (6.2) |
| Second | DP3-84/30 | 4 | (4.3) |
| | DP3-84/10 | 4 | (4.3) |
| | DP3-25/30 | 2 | (2.3) |
| | Nordette | 1 | (1.1) |

Example 9

Preliminary calculations of the incidence of pregnancy were performed for patients participating in the first clinical study of Examples 7 and 8. The results are presented in Tables 21, 22 and 23.

Table 21 presents the number of patients weighing 70 kg or more, and those weighing less than 70 kg, who became pregnant during the course of administration of the DP3-84/30 or DP3-84/10 regimen in the first clinical study.

TABLE 21

Pearl Index Calculations of Treatment Failure Rates: For all Patients, by Weight and Treatment - Completed Cycles Only (First Clinical Study)

| Regimen (Treatment Group) | Weight Category | Number of Complete Cycles | Number of 28-Day Patient Months | Number of On-Drug Pregnancies | Pearl Index |
|---|---|---|---|---|---|
| DP3-84/30 | <70 kg | 1372 | 4459.0 | 13 | 3.79 |
|  | ≧70 kg | 918 | 2983.5 | 6 | 2.61 |
| DP3-84/10 | <70 kg | 1380 | 4485.0 | 5 | 1.45 |
|  | ≧70 kg | 986 | 3204.5 | 3 | 1.22 |

Patients in the first clinical study were also monitored after the end of the study for the occurrence of pregnancy. Tables 22 and 23 present the number of pregnancies that occurred for patients in the DP3-84/30 and DP3-84/10 treatment groups after the last dose administered at the end of the study, within two weeks of the last dose, and within one month of the last dose. The values in Tables 22 and 23 are preliminary pending confirmation of the last date of study medication and date of conception. The data is presented based on the last dose taken from the Pregnancy Information obtained during the study, or from the Case Report Form Pregnancy Information.

| Based on Last Dose from Pregnancy Information | | | | |
|---|---|---|---|---|
| Regimen (Treatment Group) | Total Number of Pregnancies | After Last Dose | Within 2 Weeks of Last Dose | Within 1 Month of Last Dose |
| DP3-84/30 | 36 | 19 (52.8%) | 5 (13.9%) | 11 (30.6%) |
| DP3-84/10 | 22 | 15 (68.2%) | 4 (18.2%) | 10 (45.5%) |

| Based on Last Dose from Case Report Form Pregnancy Information | | | | |
|---|---|---|---|---|
| Regimen (Treatment Group) | Total Number of Pregnancies | After Last Dose | Within 2 Weeks of Last Dose | Within 1 Month of Last Dose |
| DP3-84/30 | 36 | 19 (52.8%) | 4 (11.1%) | 11 (30.6%) |
| DP3-84/10 | 22 | 14 (63.6%) | 3 (13.6%) | 9 (40.9%) |

Example 10

A single-dose, open-label, one period pharmacokinetic study was conducted with 24 healthy, female, adult subjects to evaluate the single dose and steady-state pharmacokinetics of tablets containing 0.150 mg levonorgestrel and 0.030 mg ethinyl estradiol. Study participants were required to take one tablet (1×0.150 mg levonorestrel/0.030 mg ethinyl estradiol) once a day for 84 consecutive days followed by 7 days of one tablet of containing only 0.030 mg of ethinyl estradiol.

Following dosing on Day 1, serial blood samples were collected pre-dose and at intervals over 24 hours after dosing. On Study Day 18, 19 and 20, samples were collected prior to dosing. On Day 21, samples were collected pre-dose and at intervals over 24 hours post-dose. On Study Day 81, 82, and 83, samples were collected prior to dosing. On Day 84, samples were collected pre-dose and at intervals thereafter. The plasma concentrations of levonorgestrel and ethinyl estradiol were measured using fully validated analytical procedures. On Study Days 88, 89, 90, and 91, samples were collected prior to dosing with the ethinyl estradiol only tablets. On Study Day 91, samples were collected prior to dosing and for 96 hours post-dosing. Samples from the pre-dose sample on Day 91 and later were analyzed for plasma concentration of ethinyl estradiol only.

During the course of the study, blood samples were also collected and analyzed for Follicle Stimulating Hormone (FSH), estradiol, Luteinizing Hormone (LH), free testosterone, and total testosterone predose on Days 1, 21, 84, 91, and on Days 98, 105, 119, 133, and 147. Plasma concentrations of each hormone were measured using standard commercially available clinical assays.

FIGS. 6 through 10 present the minimum ("Min"), maximum ("Max"), and median plasma concentrations of FSH, estradiol, LH, free testosterone and total testosterone of the patients during the course of this study, during 84 days of administration of the levonorgestrel/ethinyl estradiol, followed by 7 days of administration of ethinyl estradiol. Plasma concentrations of the hormones are also shown up to about 56 days (to Day 147) after completion of administration, during which no hormones were administered to the patients. The plasma concentration of each hormone at Day 1 represents the plasma concentration measured before the beginning of administration of the levonorgestrel/ethinyl estradiol regimen, and thus represents baseline plasma concentrations.

Application of the compounds, compositions and methods of the present invention for the medical or pharmaceutical uses described can be accomplished by any clinical, medical, and pharmaceutical methods and techniques as are presently or prospectively known to those skilled in the art. It will therefore be appreciated that the various embodiments which have been described above are intended to illustrate the invention and various changes and modifications can be made in the inventive method without departing from the spirit and scope thereof.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A method of increasing contraceptive effectiveness in a higher weight female in need thereof, the method comprising administering to the female a dosage comprising a combination of estrogen and progestin for a period of more than 50 consecutive days, followed by administration of a dosage consisting essentially of estrogen for a period of 2 to 10 consecutive days, wherein the estrogen that is administered in combination with progestin for the period of more than 50 consecutive days is administered in a daily amount equivalent to about 10 µg to about 30 µg of ethinyl estradiol, the estrogen that is administered for the period of 2 to 10 consecutive days is administered in a daily amount equivalent to about 10 µg to about 30 µg of ethinyl estradiol, and the progestin that is administered for the period of more than 50 consecutive days is administered in a daily amount equivalent to about 0.02 mg to about 1.5 mg of levonorgestrel, and wherein the higher weight female weighs about 70 kg or more.

2. The method of claim 1, wherein the dosage comprising the combination of estrogen and progestin is administered for a period of 81 to 89 consecutive days.

3. The method of claim 2, wherein the dosage comprising the combination of estrogen and progestin is administered for 84 consecutive days.

4. The method of claim 1, wherein the dosage consisting essentially of estrogen is administered for a period of 5 to 8 consecutive days.

5. The method of claim 4, wherein the dosage consisting essentially of estrogen is administered for 7 consecutive days.

6. The method of claim 1, wherein the dosage comprising the combination of estrogen and progestin is administered for 84 consecutive days, and the dosage consisting essentially of estrogen is administered for 7 consecutive days.

7. The method of claim 1, wherein the estrogen that is administered for the period of more than 50 consecutive days is administered in a daily amount equivalent to about 20 μg of ethinyl estradiol.

8. The method of claim 1, wherein the estrogen that is administered for the period of more than 50 consecutive days is administered in a daily amount equivalent to about 30 μg of ethinyl estradiol.

9. The method of claim 1, wherein the estrogen that is administered for the period of 2 to 10 consecutive days is administered in a daily amount equivalent to about 10 μg of ethinyl estradiol.

10. The method of claim 1, wherein the estrogen that is administered for the period of 2 to 10 consecutive days is administered in a daily amount equivalent to about 30 μg of ethinyl estradiol.

11. The method of claim 1, wherein the estrogen is ethinyl estradiol.

12. The method of claim 1, wherein the progestin that is administered for the period of more than 50 consecutive days is administered in a daily amount equivalent to about 0.05 mg to about 0.20 mg of levonorgestrel.

13. The method of claim 1, wherein the progestin that is administered for the period of more than 50 consecutive days is administered in a daily amount equivalent to about 0.15 mg of levonorgestrel.

14. The method of claim 1, wherein the progestin that is administered for the period of more than 50 consecutive days is administered in a daily amount equivalent to about 0.10 mg of levonorgestrel.

15. The method of claim 1, wherein the progestin that is administered for the period of more than 50 consecutive days is levonorgestrel.

16. The method of claim 1, wherein the progestin that is administered for the period of more than 50 consecutive days is desogestrel.

17. The method of claim 1, wherein an antidepressant is administered (i) in combination with the dosage consisting essentially of estrogen for the period of 2 to 10 consecutive days, (ii) intermittently, (iii) one time, or (iv) once weekly.

18. The method of claim 1, wherein the dosage comprising the combination of estrogen and progestin that is administered for the period of more than 50 consecutive days, and the dosage consisting essentially of estrogen that is administered for the period of 2 to 10 consecutive days, are administered orally.

19. The method of claim 1, wherein the dosage comprising the combination of estrogen and progestin that is administered for the period of more than 50 consecutive days, and the dosage consisting essentially of estrogen that is administered for the period of 2 to 10 consecutive days, are administered transdermally.

20. The method of claim 1, wherein the dosage comprising the combination of estrogen and progestin that is administered for the period of more than 50 consecutive days, and the dosage consisting essentially of estrogen that is administered for the period of 2 to 10 consecutive days, are administered monophasically.

21. The method of claim 1, wherein the higher weight female weighs about 80 kg or more.

22. The method of claim 1, wherein the higher weight female weighs about 90 kg or more.

23. The method of claim 1, wherein the higher weight female has a body mass index of greater than about 25.

24. The method of claim 1, wherein the higher weight female has a body mass index of greater than about 30.

25. The method of claim 1, wherein the higher weight female has a body mass index of greater than about 35.

26. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days,
    wherein the estrogen that is administered in combination with progestin for the period of 84 consecutive days is administered in a daily amount of about 10 μg to about 30 μg of ethinyl estradiol,
    the estrogen that is administered for the period of 7 consecutive days is administered in a daily amount of about 10 μg of ethinyl estradiol, and
    the progestin that is administered in combination with estrogen for the period of 84 consecutive days is administered in a daily amount of about 0.05 mg to about 0.15 mg of levonorgestrel,
    wherein the higher weight female weighs about 70 kg or more.

27. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days,
    wherein the estrogen that is administered in combination with progestin for the period of 84 consecutive days is administered in a daily amount of about 30 μg of ethinyl estradiol,
    the estrogen that is administered for the period of 7 consecutive days is administered in a daily amount of about 10 μg of ethinyl estradiol, and
    the progestin that is administered in combination with estrogen for the period of 84 consecutive days is administered in a daily amount of about 0.15 mg of levonorgestrel,
    wherein the higher weight female weighs about 70 kg or more.

28. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days,
    wherein the estrogen that is administered in combination with progestin for the period of 84 consecutive days is orally administered monophasically in a daily amount of about 30 μg of ethinyl estradiol,
    the estrogen that is administered for the period of 7 consecutive days is orally administered monophasically in a daily amount of about 10 μg of ethinyl estradiol, and the progestin that is administered in combination with estrogen for the period of 84 consecutive days is orally administered monophasically in a daily amount of about 0.15 mg of levonorgestrel, wherein the higher weight female weighs about 70 kg or more.

29. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days, wherein the estrogen that is administered in combination with progestin for the period of 84 consecutive days is administered in a daily amount of about 20 μg of ethinyl estradiol, the estrogen that is administered for the period of 7 consecutive days is administered in a daily amount of about 10 μg of ethinyl estradiol, and the progestin that is administered in combination with estrogen for the period of 84 consecutive days is administered in a daily amount of about 0.10 mg of levonorgestrel, wherein the higher weight female weighs about 70 kg or more.

30. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days, wherein the estrogen that is administered in combination with progestin for the period of 84 consecutive days is orally administered monophasically in a daily amount of about 20 μg of ethinyl estradiol, the estrogen that is administered for the period of 7 consecutive days is orally administered monophasically in a daily amount of about 10 μg of ethinyl estradiol, and the progestin that is administered in combination with estrogen for the period of 84 consecutive days is orally administered monophasically in a daily amount of about 0.10 mg of levonorgestrel, wherein the higher weight female weighs about 70 kg or more.

31. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days, wherein the estrogen that is administered in combination with progestin for the period of 84 consecutive days is administered in a daily amount of about 30 μg of ethinyl estradiol, the estrogen that is administered for the period of 7 consecutive days is administered in a daily amount of about 30 μg of ethinyl estradiol, and the progestin that is administered in combination with estrogen for the period of 84 consecutive days is administered in a daily amount of about 0.15 mg of levonorgestrel, wherein the higher weight female weighs about 70 kg or more.

32. A method of increasing contraceptive effectiveness in a higher weight female in need thereof, the method comprising administering to the female a dosage comprising a combination of estrogen and progestin for a period of 84 consecutive days, followed by administration of a dosage consisting essentially of estrogen for a period of 7 consecutive days, wherein the estrogen that is administered in combination with progestin for the period of 84 consecutive days is orally administered monophasically in a daily amount of about 30 μg of ethinyl estradiol, the estrogen that is administered for the period of 7 consecutive days is orally administered monophasically in a daily amount of about 30 μg of ethinyl estradiol, and the progestin that is administered in combination with estrogen for the period of 84 consecutive days is orally administered monophasically in a daily amount of about 0.15 mg of levonorgestrel, wherein the higher weight female weighs about 70 kg or more.

33. A method of increasing contraceptive effectiveness in a higher weight female in need thereof, the method comprising administering to the female a dosage comprising a combination of estrogen and progestin for a period of 21 consecutive days, followed by administration of a dosage consisting essentially of estrogen for a period of 7 consecutive days, wherein the estrogen that is administered in combination with progestin for the period of 21 consecutive days is administered in a daily amount of about 20 μg of ethinyl estradiol, the estrogen that is administered for the period of 7 consecutive days is administered in a daily amount of about 10 μg of ethinyl estradiol, and the progestin that is administered for the period of 21 consecutive days is administered in a daily amount of about 0.15 mg of desogestrel, and wherein the higher weight female weighs about 70 kg or more.

34. The method of claim 33, wherein an antidepressant is administered (i) in combination with the dosage consisting essentially of estrogen for the period of 7 consecutive days, (ii) intermittently, (iii) one time, or (iv) once weekly.

35. The method of claim 33, wherein the dosage comprising the combination of estrogen and progestin that is administered for the period of 21 consecutive days, and the dosage consisting essentially of estrogen that is administered for the period of 7 consecutive days, are administered orally.

36. The method of claim 33, wherein the dosage comprising the combination of estrogen and progestin that is administered for the period of 21 consecutive days, and the dosage consisting essentially of estrogen that is administered for the period of 7 consecutive days, are administered transdermally.

37. The method of claim 33, wherein the dosage comprising the combination of estrogen and progestin that is administered for the period of 21 consecutive days, and the dosage consisting essentially of estrogen that is administered for the period of 7 consecutive days, are administered monophasically.

38. The method of claim 33, wherein the higher weight female weighs about 80 kg or more.

39. The method of claim 33, wherein the higher weight female weighs about 90 kg or more.

40. The method of claim 33, wherein the higher weight female has a body mass index of greater than about 25.

41. The method of claim 33, wherein the higher weight female has a body mass index of greater than about 30.

42. The method of claim 33, wherein the higher weight female has a body mass index of greater than about 35.

* * * * *